United States Patent

Lin et al.

[11] Patent Number: 6,091,846
[45] Date of Patent: Jul. 18, 2000

[54] METHOD AND SYSTEM FOR ANOMALY DETECTION

[75] Inventors: YouLing Lin, Plano; A. Kathleen Hennessey, Lubbock; Ramakrishna Pattikonda, Dallas; Veera S. Khaja, Dallas; Rajasekar Reddy, Dallas, all of Tex.

[73] Assignee: Texas Instruments Incorporated, Dallas, Tex.

[21] Appl. No.: 08/867,156

[22] Filed: May 30, 1997

[51] Int. Cl.[7] .............................. G06K 9/00; G06K 9/52; G06T 7/00; G06T 7/60

[52] U.S. Cl. .......................... 382/145; 382/149; 382/151; 382/168

[58] Field of Search ................................ 348/86, 87, 126, 348/94, 95, 125; 382/141–152, 168; 364/490, 491, 559

[56] References Cited

U.S. PATENT DOCUMENTS

| | | |
|---|---|---|
| 4,233,625 | 11/1980 | Atman . |
| 4,353,087 | 10/1982 | Berry et al. . |
| 4,509,075 | 4/1985 | Simms et al. . |
| 4,550,374 | 10/1985 | Meshman et al. . |
| 4,579,455 | 4/1986 | Levy et al. ............................... 356/394 |
| 4,641,257 | 2/1987 | Ayata ....................................... 364/559 |
| 4,791,586 | 12/1988 | Maeda et al. ........................... 364/491 |
| 4,794,648 | 12/1988 | Ayata et al. . |
| 4,907,285 | 3/1990 | Nakano et al. . |
| 4,955,062 | 9/1990 | Terui . |
| 5,048,100 | 9/1991 | Kuperstein . |
| 5,086,477 | 2/1992 | Yu et al. ................................. 382/243 |
| 5,109,430 | 4/1992 | Nishihara et al. ......................... 382/8 |
| 5,144,683 | 9/1992 | Suzuki et al. ............................. 382/16 |
| 5,220,621 | 6/1993 | Saitoh ...................................... 382/22 |
| 5,321,770 | 6/1994 | Huttenlocher et al. .................. 382/22 |
| 5,375,194 | 12/1994 | Hori et al. ............................... 395/133 |
| 5,436,979 | 7/1995 | Gray et al. .............................. 388/141 |
| 5,513,275 | 4/1996 | Khalaj et al. ........................... 382/149 |
| 5,515,453 | 5/1996 | Hennessey et al. ..................... 382/141 |
| 5,544,256 | 8/1996 | Brecher et al. ......................... 382/149 |

OTHER PUBLICATIONS

"Investigation of a Fuzzy Grammar for Automated Visual Inspection," by Hahn Kwang–Soo, Dissertation in Interdisciplinary Engineering, Graduate Faculty, Texas Tech University, Aug. 1989.

"Picture Interpretation A Symbolic Approach," by Sandy Dance, Terry Caelli and Zhi–Qiang Liu, Series in Machine Perception and Artificial Intelligence—vol. 20, World Scientific, Apr. 1995.

"Symbolic Image Interpretation by Parsing, Interpreting, and Pruning," by Staffan Truvé, A Dissertation for the Ph.D. Degree in Computing Science at Chalmers University of Technology, Department of Computer Sciences, dated Jun. 4, 1992.

(List continued on next page.)

*Primary Examiner*—Scott Rogers
*Attorney, Agent, or Firm*—Robert L. Troike; Richard L. Donaldson

[57] ABSTRACT

A system and method for detecting anomalies on a manufactured device includes or utilizes a moveable stage for holding and positioning the device, a camera for capturing an image of the device on the stage, a digitizer coupled to the camera for producing a digital-pixel-based representation of the image, and a computer having a processor and memory. The computer is coupled to the digitizer for receiving the digital-pixel-based representation from the digitizer and coupled to the stage for selectively moving the stage to align the device. The computer is programmed to be operable to symbolically decompose a digital-pixel-based representation of an image to create a primitive-based representation of the image. The image may be aligned by the computer with respect to the rotation of geometric objects in the image by developing a histogram of angles and lengths and matching them to determine a rotational shift.

14 Claims, 34 Drawing Sheets

OTHER PUBLICATIONS

"Symbolic Reasoning Among 3–D Models and 2–D Images," A Dissertation Submitted to the Department of Computer Science and the Committee on Graduate Studies of Stanford University in Partial Fulfillment of the Requirements for the Degree of Doctor of Philosophy, by Rodney Allen Brooks, dated Jun. 1981.

"Symbolic Pixel Labeling for Curvilinear Feature Detection," Computer Vision Laboratory, Center for Automation Research, University of Maryland, by John Canning, J. John Kim, and Azriel Rosenfeld, dated Jan. 1987.

"Symbolic Learning and Interpretation of 2–D Electrophoresis Gels," University Libraries, Carnegie Mellon University, by Pierre Nugues, Robert Whalen and Jean–Paul Haton, dated Apr. 11, 1991.

"Techniques for Syntactic Analysis of Images with Application for Automatic Visual Inspection," Dissertation in Interdisciplinary Engineering, Graduate Faculty, Texas Tech University, by Youling Lin, Dec. 1990.

"Segmentation Through Symbolic Surface Descriptions," Computer Vision Laboratory, Electrical Engineering and Computer Science Dept., The University of Michigan, by Paul Besl and Ramesh Jain, dated Feb. 1986.

"Zero–Crossing Symbolic Vision Primitives Emulating Physiologic Encoding Schemes," Thesis Submitted to the Faculty of the Oregon Graduate Center in Partial Fulfillment of the Requirements for the Degree Master of Science in Computer Science & Engineering, by Daniel P. Lulich, dated Dec. 1985.

"Code Converter Designs Using Optical Symbolic Substitution Logic," Thesis Submitted to Graduate Engineering & Research, School of Engineering, University of Dayton, In Partial Fulfillment of the Requirements for The Degree Master of Science in Electrical Engineering, by Constantinos C. Agrotis, dated Jul. 1989.

"Symbolic Inverse of Discrete Gaussian Blur," Computer Vision and Robotics Laboratory, Department of Electrical Engineering, McGill University, by B. Kimia and S.W. Zucker, dated Jun. 1985.

"The Symbolic Representation, Analysis, and Manipulation of Morphological Algorithms," A Thesis Presented to The Academic Faculty, in Partial Fulfillment of the Requirements for the Degree of Doctor of Philosophy in Electrical Engineering, Georgia Institute of Technology, by Craig Howard Richardson, dated Dec. 1991.

"Fundamentals of Electronic Image Processing," by Arthur R. Weeks, Jr., SPIE/IEEE on Imaging Science & Engineering, not dated.

"Symbolic Projection for Image Information and Retrieval and Spatial Reasoning," by Shi–Kuo Chang and Erland Jungert, Academic Press, not dated.

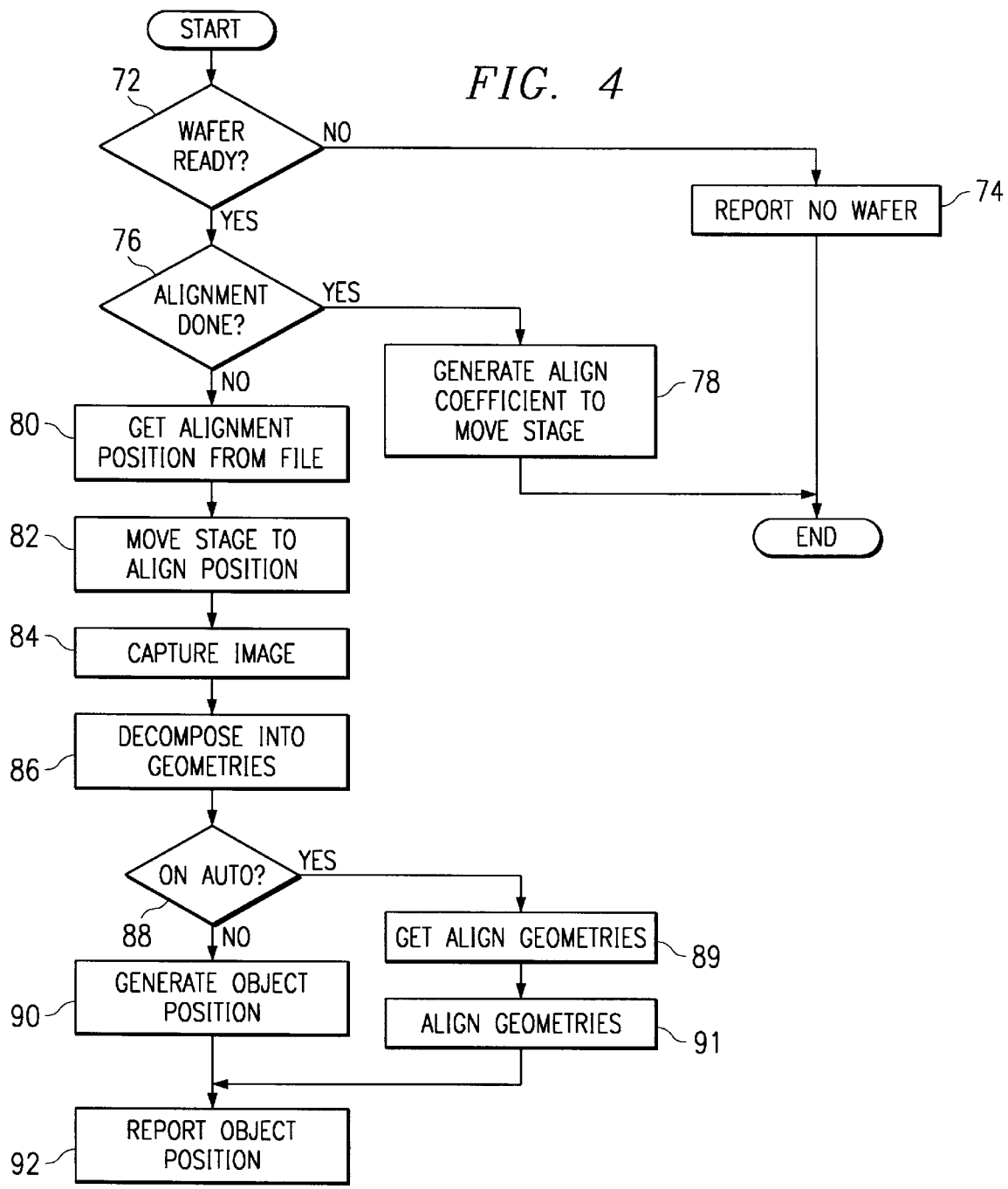

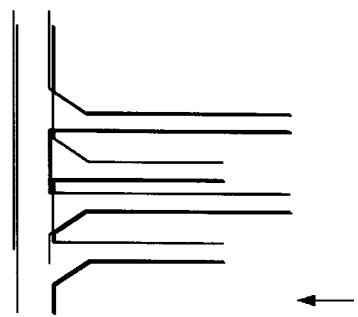
FIG. 10e
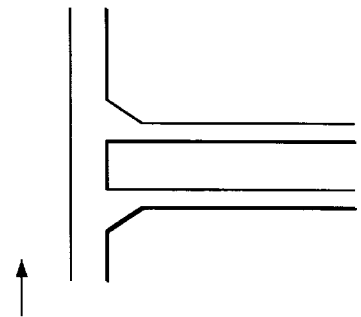
FIG. 10f
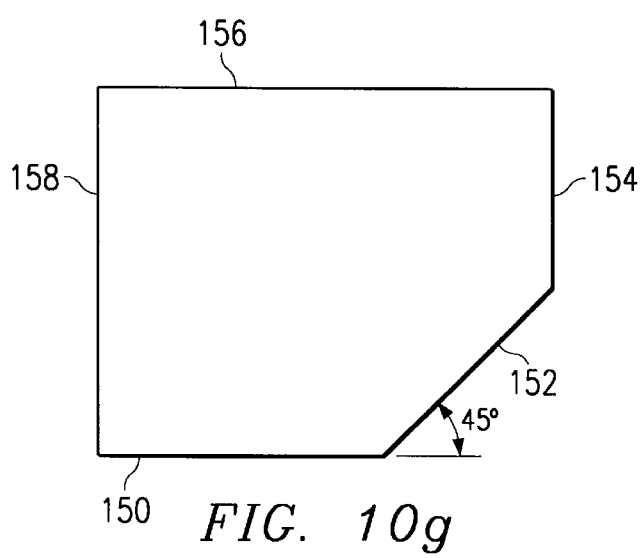
FIG. 10g
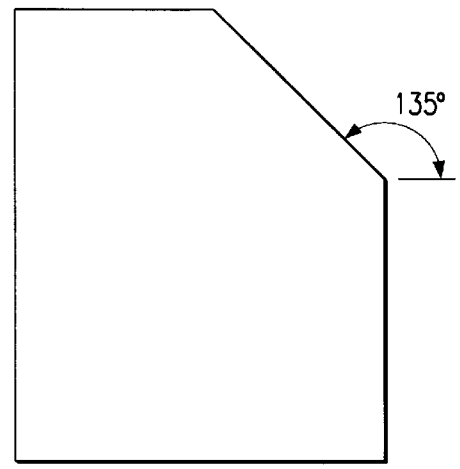
FIG. 10h
FIG. 10i
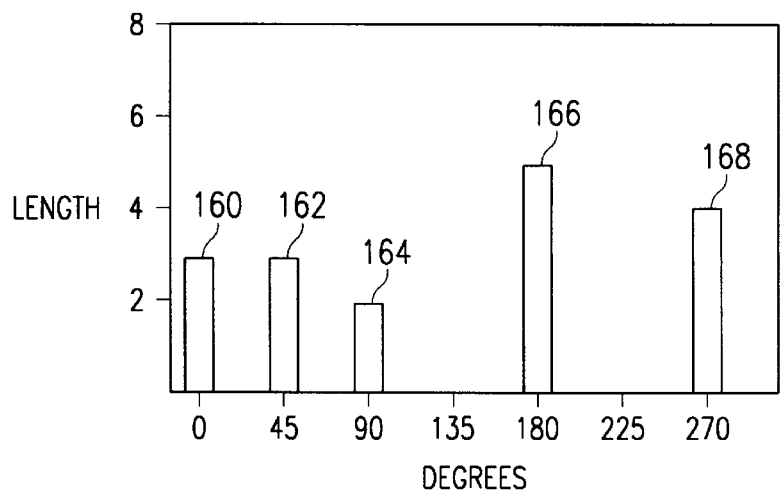

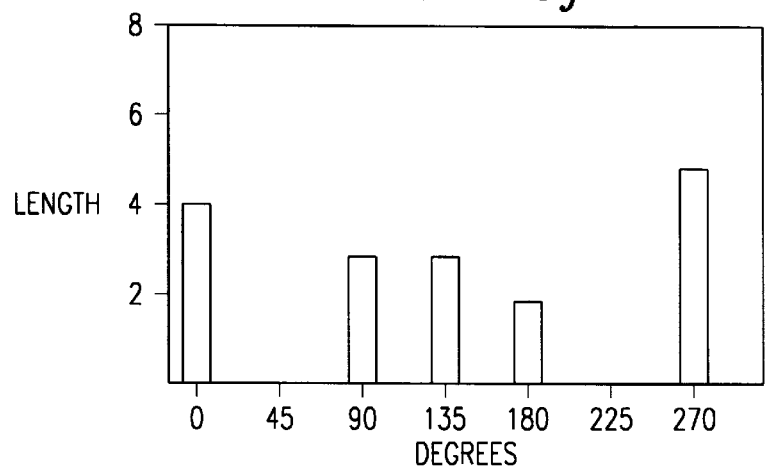
FIG. 10j
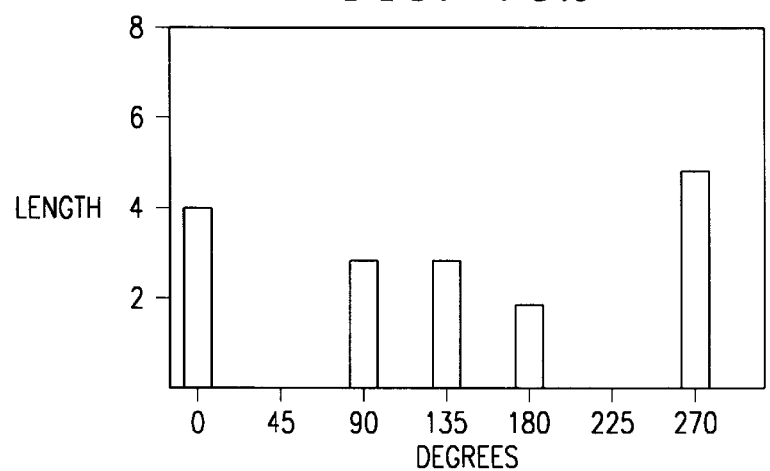
FIG. 10k
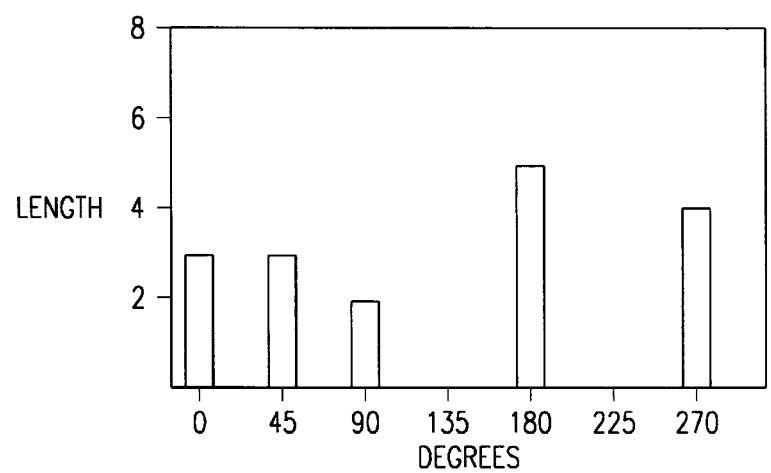

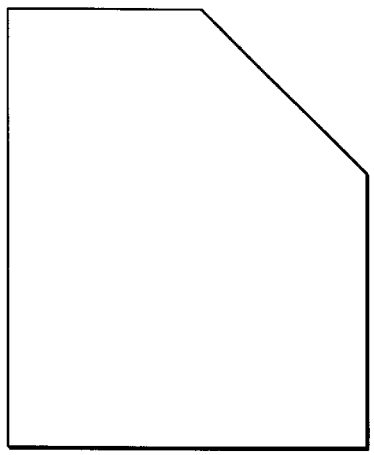
FIG. 10m
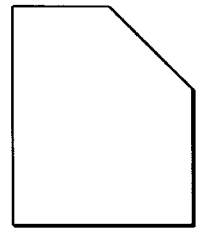
FIG. 10n
FIG. 10o
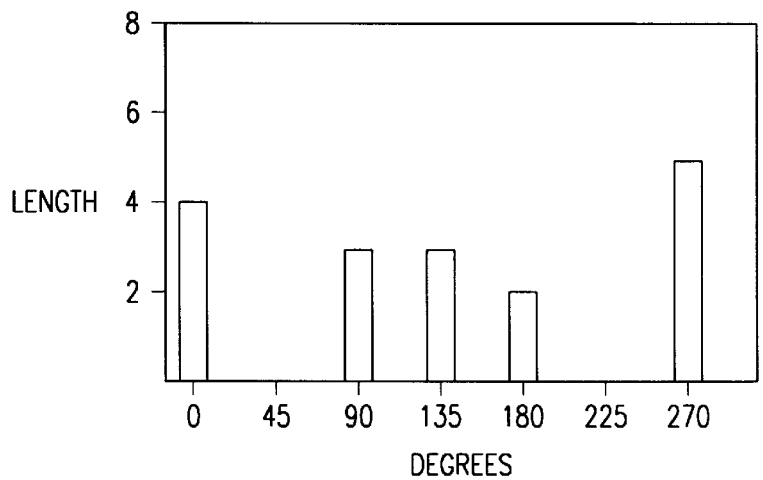
FIG. 10p
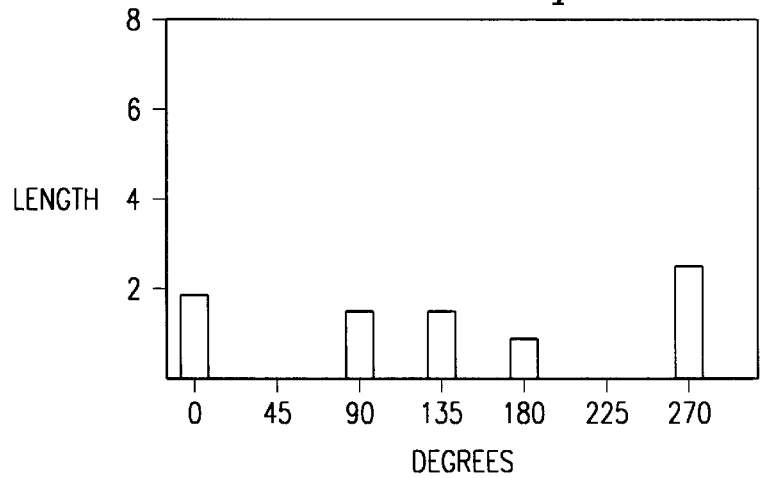

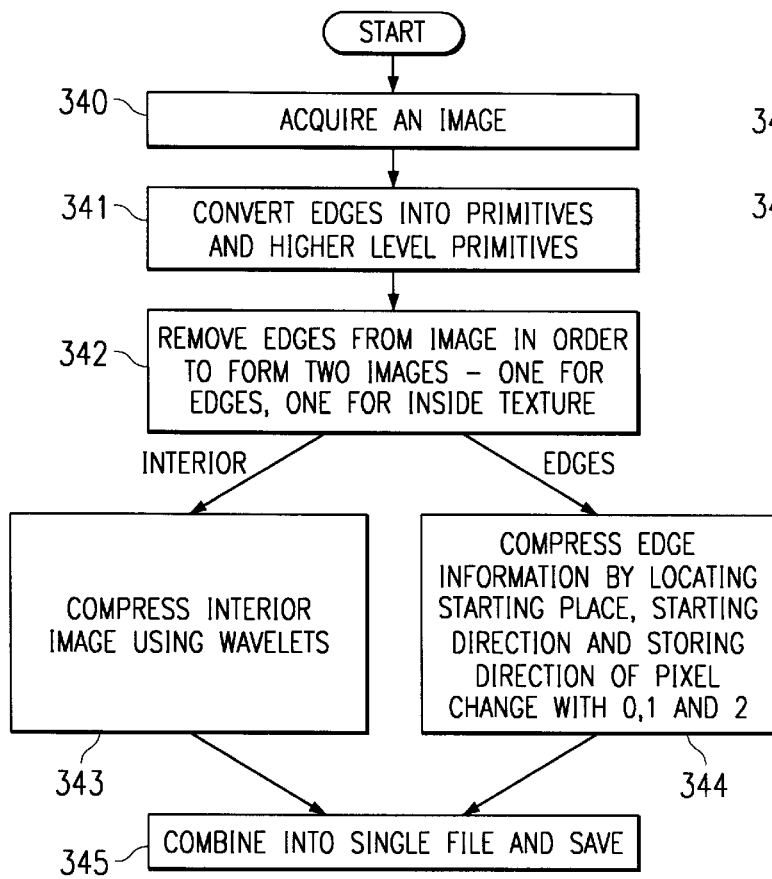
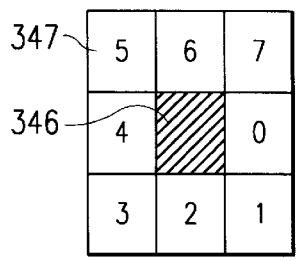
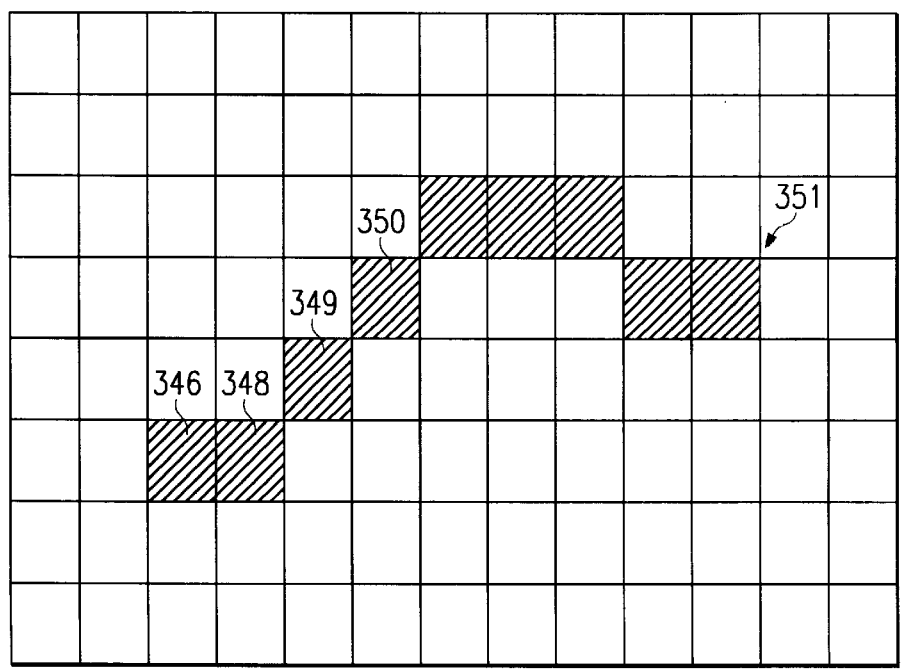
FIG. 20a
FIG. 20c
FIG. 20b

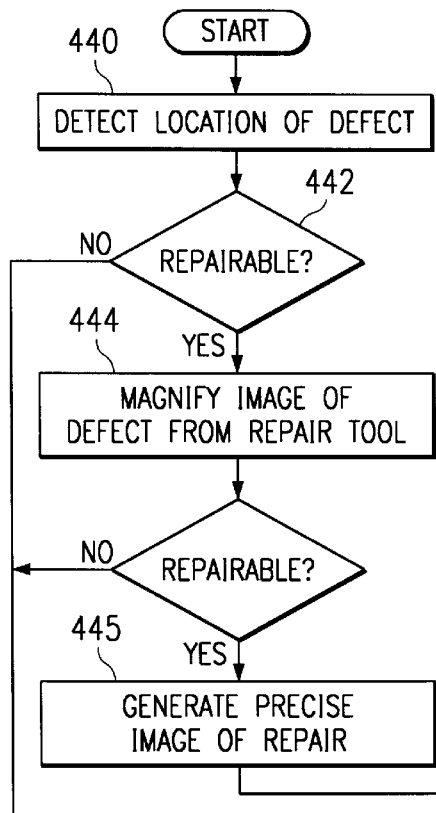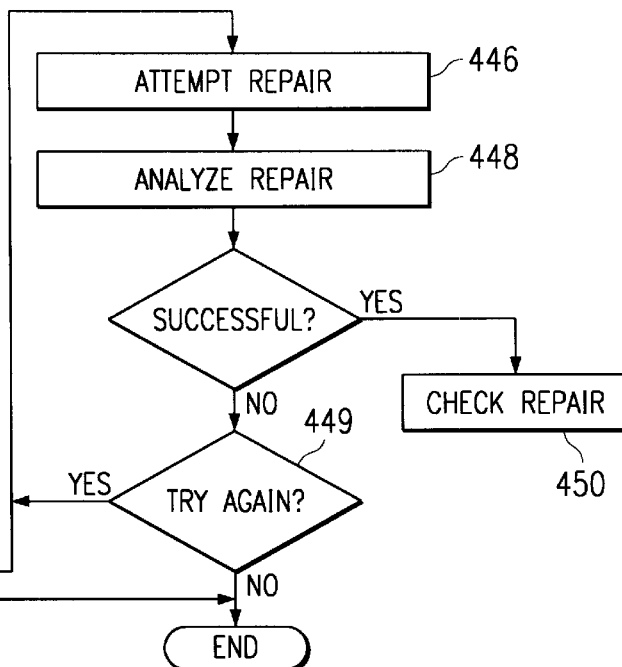
FIG. 26
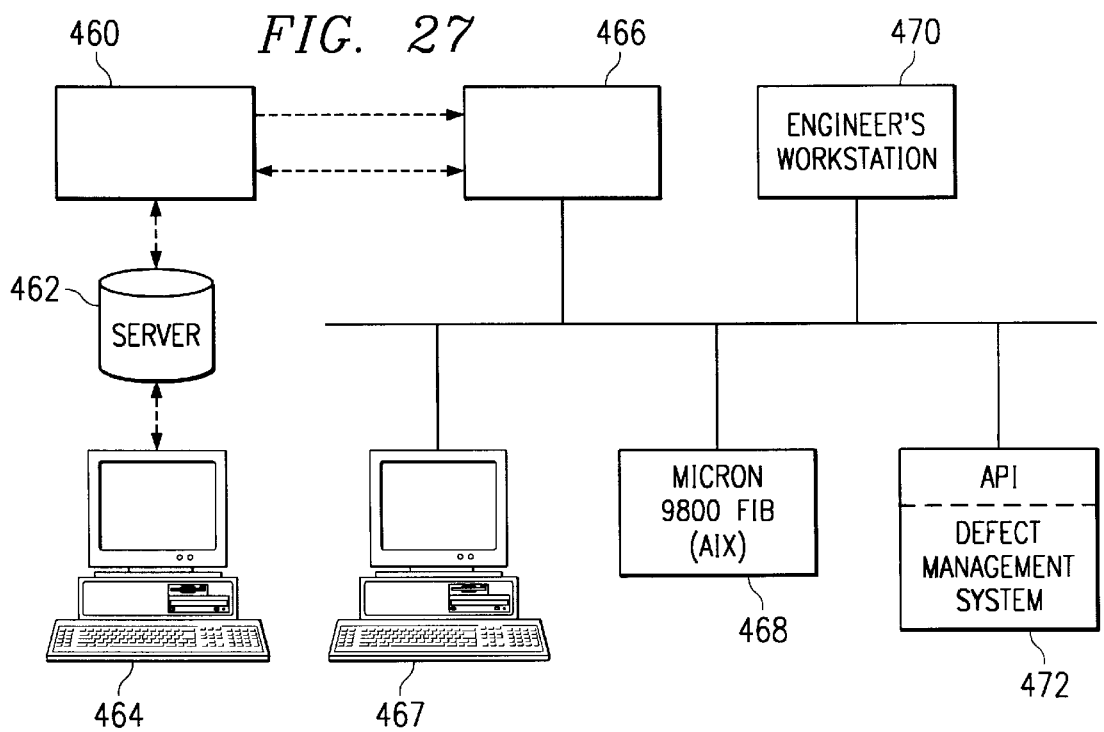
FIG. 27

480

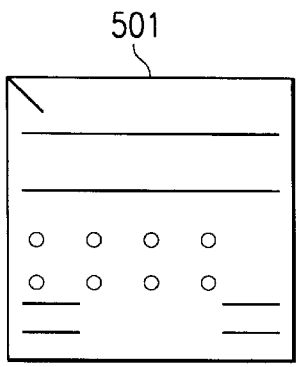
501
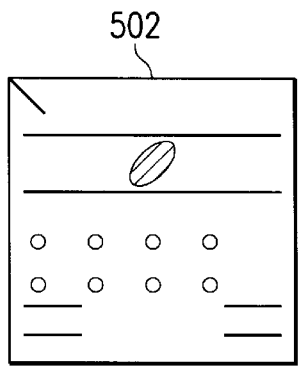
502
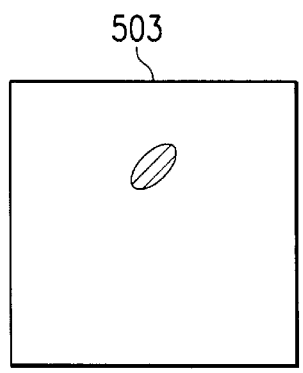
503
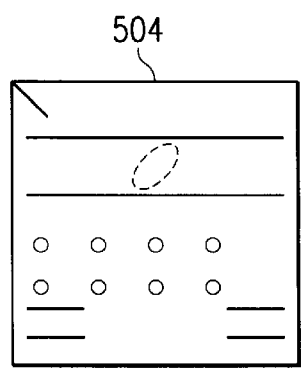
504
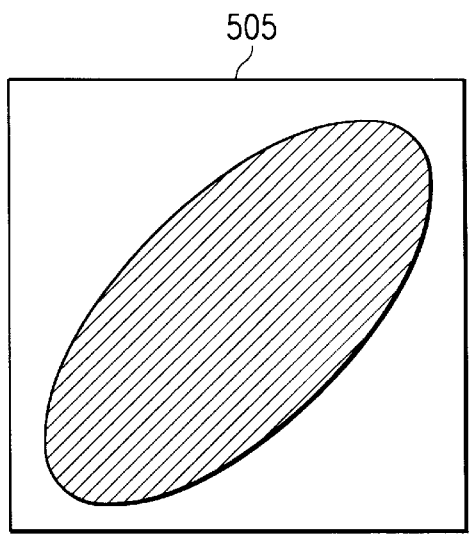
505
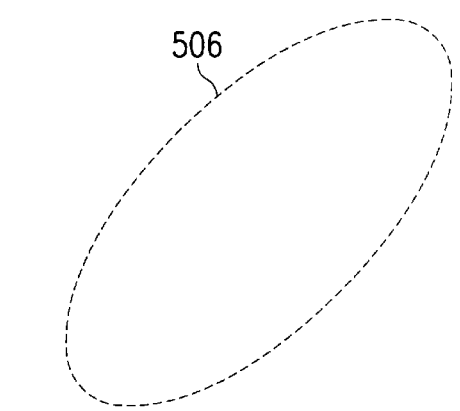
506
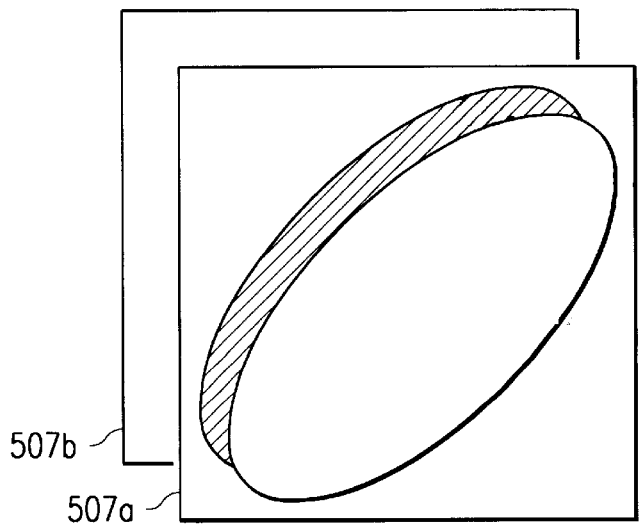
507b
507a
FIG. 30a

METHOD AND SYSTEM FOR ANOMALY DETECTION

RELATED APPLICATIONS

This application claims the benefit of the following provisional applications: Ser. No. 06/018,807, entitled Automated Circuit Repair, filed May 31, 1996; Ser. No. 06/018,836, entitled Method And System For Defect Characterization And/or Diagnosis, filed May 31, 1996; Ser. No. 06/018,815, entitled Method and System For Semiconductor Anomaly Detection, filed May 31, 1996; and Ser. No. 06/018,804, entitled Knowledge Base Management, filed May 31, 1996.

This application is related to the following applications: U.S. patent application Ser. No. 08/666,553, entitled System and Method for Circuit Repair, filed May 30, 1997 (Attorney's Docket TI-18924); U.S. patent application Ser. No. 08/867,154, entitled System and Method for Defect Characterization and/or Diagnosis, filed May 30, 1997 (Attorney's Docket TI-21171); U.S. patent application Ser. No. 08/867,771, entitled System and Method for Knowledgebase Generation and Management, filed May 30, 1997 (Attorney's Docket TI-23478). Reference is also made to and the benefit claimed for the following pending applications, each of which is incorporated herein by reference: U.S. patent application Ser. No. 08/186,691, entitled Apparatus and Method for Aligning and Measuring Misregistration, filed Jan. 24, 1994; U.S. patent application Ser. No. 08/603,026, entitled Apparatus and Method for Aligning and Measuring Misregistration, filed Feb. 16, 1996; U.S. patent application Ser. No. 08/602,998, entitled System and Method for Recognizing Visual Indicia, filed Feb. 16, 1996; U.S. patent application Ser. No. 08/347,020, entitled Apparatus and Method for Automatic Knowledge-based Object Identification, filed Nov. 30, 1994.

TECHNICAL FIELD OF THE INVENTION

This invention relates to defect classification and diagnosis of manufacturing defects.

BACKGROUND OF THE INVENTION

In most manufacturing processes, management of through-put and yield are of concern. The ability to locate potential problems, identify problems, and take corrective action to obviate the source of the defect, and if possible, to repair the defect, can make a significant difference in the performance of manufacturing process. Therefore, it is desirable to have the best systems possible for identifying possible problems or anomalies, identifying an anomaly as a particular type of defect, identifying the source of the defect, and repairing the manufactured object to correct the defect if possible. This is particularly true in the semiconductor industry.

In the semiconductor manufacturing industry, a challenge remains to improve yields as the designs get smaller and smaller. Particles and process defects can limit yields in manufacturing semiconductor devices. Therefore, systems that perform the general functions described above can become extremely important. Conventional techniques have shortcomings including less than desirable speed and accuracy. With respect to identifying defects in the manufacturing process, manual classification has been required of anomalies and manual diagnosing of the cause of defects. Such manual inputs may have resulted in inconsistent results and consumption of considerable operator time.

SUMMARY OF THE INVENTION

According to an aspect of the present invention, a system for detecting anomalies on a manufactured device is provided that includes a moveable stage for holding and positioning the device; a camera for capturing an image of the device on the stage; a digitizer coupled to the camera for producing a digital-pixel-based representation of the image; and a computer having a processor and memory, the computer coupled to the digitizer for receiving the digital-pixel-based representation from the digitizer and coupled to the stage for selectively moving the stage to align the device, with the computer the computer is programmed to be operable to: symbolically decompose a digital-pixel-based representation of an image to create a primitive-based representation of the image and to locate an anomaly in the primitive-based representation of the image. According to another aspect of the present invention, the computer is operable to decompose the digital-pixel-based representation of an image by aligning geometric objects in the pixel-based representation of the image and is operable to align the geometric objects with respect to rotation by developing a histogram of angles and lengths and matching them to determine a rotational shift.

According to another aspect of the present invention, the computer of an anomaly detecting system may locate defects in a primitive-based image by analyzing the primitive-based representation of the image for irregular breaks in lines or irregular angles to locate anomalies, by dividing the primitive-based representation of the image into segments, comparing segments to locate repetitive patterns, and then deleting the repetitive patterns from each segment to identify anomalies, by comparing the primitive-based representation of the image with a stored, predetermined reference image, or by subtracting a stored, predetermined reference image from the primitive-based representation of the image and subtracting a second captured reference image.

According to another aspect of the present invention, a method for detecting anomalies on a manufactured device includes the steps placing the manufactured device on a moveable stage; capturing and preparing a digital-pixel-based representation of the image; symbolically decomposing the digital-pixel-based representation of an image to create a primitive-based representation of the image; analyzing the primitive-based representation of the image to detect and locate any anomalies; and wherein the step of decomposing the digital-pixel-based representation of an image includes aligning geometric objects in the pixel-based representation of the image with respect to rotation by developing a histogram of angles and lengths and matching them to determine a rotational shift.

BRIEF DESCRIPTION OF THE DRAWINGS

For a more complete understanding of the present invention, and the advantages thereof, reference is now made to the following descriptions taken in conjunction with the accompanying drawings, in which:

FIG. 4 is a flowchart of the wafer alignment in the computer;

FIG. 10 illustrates methods of vertical, horizontal, rotational and magnification alignment using histograms wherein FIG. 10e illustrates the horizontal alignment of the primitives; FIG. 10f illustrates vertical alignment of primitives; FIG. 10g illustrates the primitives of an image; FIG. 10h illustrates the primitives of the first image rotated; FIG. 10i illustrates histogram of the first image primitives; FIG. 10j illustrates histogram of the second image primitives; FIG. 10k illustrates alignment of histogram primitives; FIG. 10m illustrates the primitives of a first image; FIG. 10n illustrates the primitives of a second image; FIG. 10o illustrates the histogram of first image; FIG. 10p illustrates histogram of second image primitives.

FIG. 16 illustrates a defect determined by Method 4 where

FIG. 20a is a flowchart outlining an image compression method; FIG. 20b illustrates edge encoding; and 20c is a pixel by pixel representation of the primative of an edge;

FIG. 26 is a block diagram of the circuit repair system according to the present invention;

FIG. 27 is a detailed block diagram of the circuit repair system;

FIG. 29a illustrates an image of a defect found at a location provided by gross inspection tool and FIG. 29b illustrates the symbolic representation of FIG. 29a;

FIG. 30a illustrates image subtraction to outline defect and FIG. 30b illustrates the defects outlined;

FIG. 41 illustrates use of subdirectories to store and retrieve defect records and image wherein

DETAILED DESCRIPTION OF THE INVENTION

The preferred embodiments of the present invention and its advantages are best understood by referring to FIGS. 1–42 of the drawings, like numerals being used for like and corresponding parts of the various drawings.

I. SYSTEM OVERVIEW

A. Introduction

Figure 1:
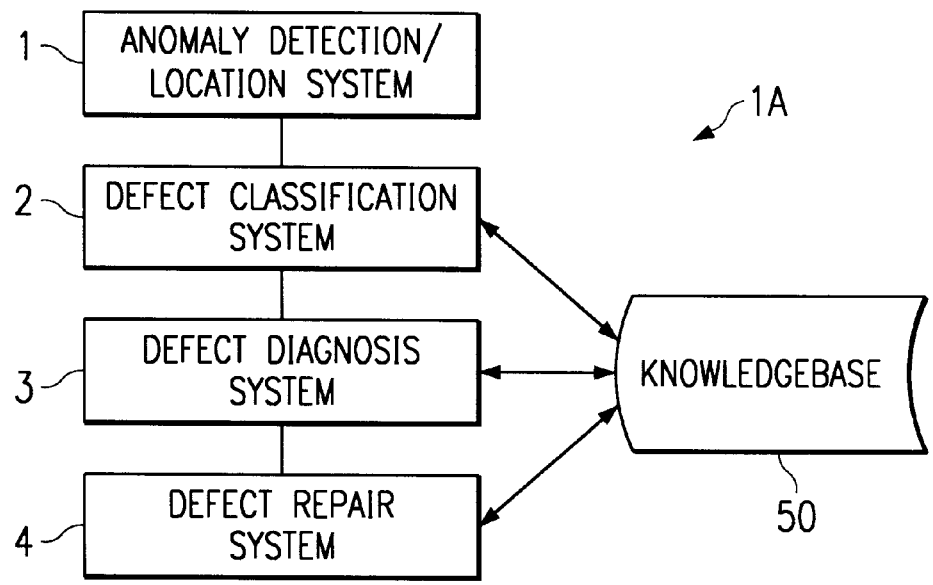
FIG. 1 is a block diagram of an integrated defect detection, classification, diagnosis and repair system.

Referring to FIG. 1, there is illustrated a block diagram of the integrated defect detection, classification, diagnosis and repair system (IDDCDR System). In System 1A, wafer and/or manufacturing anomalies are detected and located by an anomaly detecting-and-locating system 1; defects are identified, precisely located and classified by a defect classification system 2; and, after having been stored in a defect knowledgebase 50, the defects are diagnosed to determine their cause by a defect diagnosis system 3 and whose repair is determined and directed by a defect repair system 4. Compression of information may be used throughout system 1A to facilitate and enhance its operation. The Integrated Defect Detection/Classification/Diagnosis/Repair System may include a UNIX, DOS, Windows or other operating system and special purpose image generation, capture and server network modules installed in and/or controlled by a computer.

B. Introduction to the Manufacturing Anomaly Detecting-and-Locating System

Figure 2:
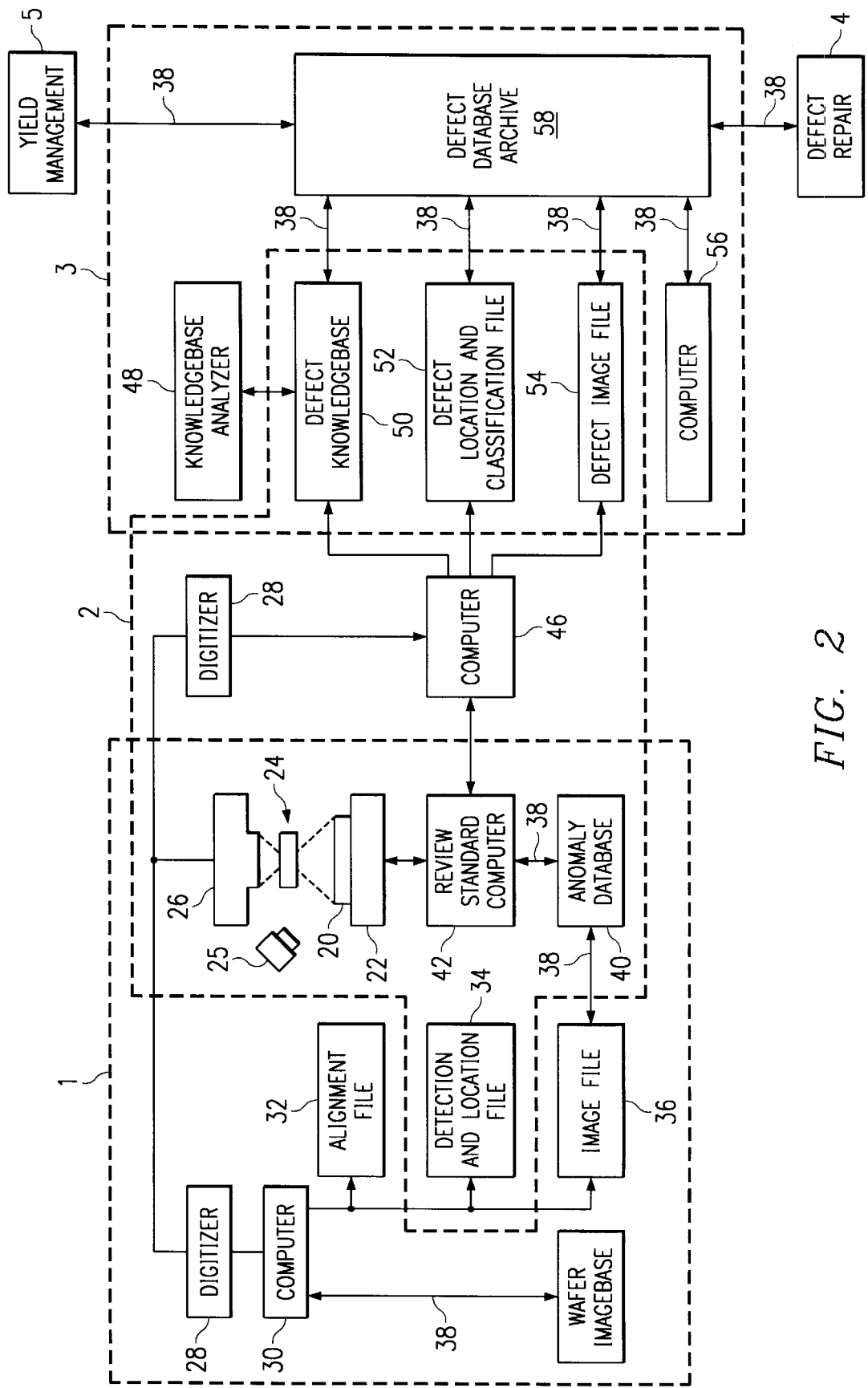
FIG. 2 is a block diagram of an integrated defect detection, classification, diagnosis and repair system according to an aspect of the present invention.

Referring to FIG. 2, an embodiment of the manufacturing anomaly detecting-and-locating system 1 is shown. While the anomaly detecting-and-locating system may be used in numerous applications, it is presented here in the context of semiconductor wafers. The system 1 locates anomalies on semiconductor wafers.

A semiconductor wafer 20 is placed on an xy stage 22 so that an area of the wafer 20 is illuminated by an energy source 25 that produces energy such as white light, darkfield light, polarized light, laser refraction, scanning electrons, focused ion beams or X-ray such that anomalies on the wafer can be detected using a microscope 24 or other sensor device. A camera 26 or other image capturing device captures the microscope's 24 image while a digitizer 28, such as a frame grabber or other means of converting the image generated by the sensor from analog to digital form, supplies a digitized rendering of the image to an anomaly detecting-and-locating computer 30. Alternatively, an image stored in memory can be provided to anomaly detecting-and-locating computer 30. This produces, under program control, information about the anomaly, such as its approximate size and location. For an anomaly that is digitally represented with greater than 10 pixels, the anomaly is classified using the defect knowledge base. Anomalies in close proximity to another are added to a group of anomalies to be classified as a defect cluster. This information is stored in an anomaly location file 34, in an alignment file 32, and an image of the anomaly may also be stored in an anomaly image file 36. These files are transmitted via a network 38 or other means to an anomaly database 40 where the files may be retrieved by other stations and systems connected to network 38 such as by review station computer 42.

C. Introduction to the Defect Classification System

The defect classification system precisely locates an anomaly or defect and in its normal operation will classify the type of defect that it is. The defect classification system may be used to classify anomalies in numerous applications, but is presented here with reference to anomalies on semiconductor wafers. System 2 is provided as such an example in FIG. 2.

Referring to FIG. 2 and using, for this example, the same camera 26, microscope 24, stage 22 and digitizer 28 as in the location system 1, a review station computer 42 obtains the anomaly location file 34 for a selected wafer from the anomaly database server 40 on the network 38. The review station computer 42 aligns the wafer 20 or other manufactured object by moving its xy stage 22 under the microscope 24 in order to obtain an image of the area containing the anomaly, using an energy source 25 which provides illumination of one of the small areas indicated in the anomaly location file 34. The review station may have its own camera, microscope, and stage. To classify smaller defects, such as semiconductor defects under five microns in size, the camera typically will have a finer area or line scan camera and the microscope a higher resolution microscope than for the detecting-and-locating system. The review station computer 42 focuses the microscope 24 to sharpen the image of the anomaly area. The image is acquired by camera 26 and sent to digitizer 28 or other such image capture device so that the analog signal from the camera is converted to a digital signal. The digital signal is transferred directly to the defect classification computer 46. There the focus of microscope 24 and its energy source 25 are verified from the image captured by the digitizer 28 using a primitive-based wafer alignment system, registration check, and zero crossing noise cancellation system. In this regard, reference is made to U.S. Pat. Nos. 5,515,453 and 5,553,168, which are incorporated herein by reference for all purposes.

The defect classification system 2 operates in two modes: a learning mode and an operating mode. When operating in learning mode, the defect classification computer 46, under program control, examines the image, determines whether a defect exists, precisely locates and outlines the defect, produces a set of defect image descriptors and adds the descriptors of the defect to the defect knowledgebase if in learning mode. In operating mode, defect classification computer 46 matches the descriptors of the defect to those already in the defect knowledgebase and produces a defect classification. This classification is added to the information obtained from the anomaly location file 34, and the information is written to a record in a defect location/classification file 52 and an image of the defect is stored in a defect image file 54. The production and comparison of sets of descriptor is discussed in detail in the cited applications. One set of such defect classifications may be repairable defects and non-repairable defects. In addition, such defect classifications may include misaligned components, scratches, stains, particles, metal missing, excess metal, and/or nitride residue. Also, a diagnosis may be made including scumming, low furnace temperature, contamination of developer, sputter removal, etc. The contents of defect knowledgebase 50 are monitored and maintained, either by an operator using a display and a keyboard referring to a report generator (not pictured), or automatically by a knowledgebase analyzer 48.

At regular intervals the contents of the defect knowledgebase 50, the defect location/classification file 52 and the defect image file 54 are transmitted along the network 38 to the defect database archive 58 for use by the defect diagnosis system 3, including a defect diagnosis computer 56. The defect image file 54 may be compressed by any one of a number of compression methods including such standard compression methods as JPEG compression; by the image compression method described in the preceding invention "Apparatus and Method for Automatic Knowledge based Object Identification" in application Ser. No. 08/347,020, filed Nov. 30, 1994, by Hennessey, et al., which is incorporated herein by reference for all purposes; by an image compression method in the public domain usually referred to as "Wavelets"; or by an approach using both symbolic decomposition and wavelet complication.

D. Introduction to the Defect Diagnosis System

The defect diagnosis system 3, in conjunction with the automated yield management system 5, retrieves and reviews defect information and images stored in defect database archive 58 based on any one or more of its characteristics, such as lot number, wafer number, date, process level, or location for production of displays and reports containing graphs, histograms, statistical tables, wafer maps, and defect images to enable the operator to obtain an overall view of defect patterns and trends, or to diagnose specific defects. As is the case of defect classification when in the learning mode the operator enters a specific diagnosis into the defect knowledgebase 50. When in operation mode, the defect diagnosis is determined automatically from the knowledgebase 50 and added to the defect record stored in defect database archive 58.

Beyond doing reports, defect diagnosis system 3 can also be used to identify defects which can be repaired with a repair facility such as a Micron 9800, and by passing the location of each repairable defect to a repair record in the defect database archive 58.

E. Introduction to the Defect Repair System

If the defect classification has classified an anomaly or defect as one that can be repaired, defect repair system 4 may be used to do so. Continuing the semiconductor example of FIG. 2, a repair may be made by using a repair tool to remove "deposit layers" or add "missing metal." Locations and images of defects classified as repairable are retrieved from defect database archive 58 and passed to a repair tool such as a Micron 9800 which captures a more precise image of the defect, from which the defect repair system 4 generates the type of repair, e.g., remove or deposit metal, and a precise outline of the actual repair for the repair tool and inspects the repair to determine whether it has been correctly done. This information is transmitted in a defect repair record to defect database/archive 58 which may be consulted later to determine whether to "bin" or designate a specific die as defective, to "scrap" or discard an entire wafer, as well as to evaluate the repair process or to make other changes to manage yields.

F. Introduction to the Yield Management System

Patterns and other information developed by analyzing defects detected may allow improved performance of the manufacturing process. For example, continuing the semiconductor example, a yield management system may analyze information to get at a source problem. Referring to FIG. 2, the yield management system 5 retrieves and analyzes information from the defect database/archive 58 and other information resources available on the network 38 and from other sources such CAD Computer-Aided Designs, results of electrical tests carried out on wafers, wafer inspection reports and images, histories of defects, process models, wafer process histories, and packaged die failure reports. The yield management system 5 models and evaluates strategies for intervention in fabrication and other processes so as to improve the number of die on each wafer that pass acceptance tests when packaged and do not subsequently fail when installed in an application device or system. The yield management system 5 indexes and retrieves information about defects using the same set and format of descriptors in the automated defect classification system 2 and automated defect diagnosis systems 3, thereby reducing the amount of processing needed to translate indexes from one format to another and greatly reducing the amount of storage needed for such indexes.

G. Introduction to the knowledgebase Creation and Management

Knowledgebase or database creation involves the determination of rules based on a plurality of descriptors which can catagorize an anomaly. Since a given defect may not fit exactly into a given set of rules, confidence levels are determined for a set of descriptors. In one embodiment the confidence levels are set at 60 percent. Typically, the value of the confidence levels are stored apart from the descriptors, in a separate file. As the size of the confidence level increases, the chance that an anomaly will be classified increases. The likelihood of misclassification, however, increases because the confidence levels for sets of descriptors get large enough and begin to overlap. To avoid misclassification and to increase the accuracy of classification, certain descriptors can be emphasized more than others by mathematically weighting those descriptors. Descriptors which are determined to be a good discriminant—that is, good at distinguishing one class from another—can be given greater weight then less important descriptors. Weights are typically stored apart from the descriptors so that they can be applied on the fly.

The performance of the defect knowledgebase 50 can be improved by the use of knowledge base analyzer 48. Knowledgebase analyzer 48 improves the performance of the defect knowledgebase 50 by allowing the contents to be edited, setting new weights for descriptors and providing a measure of the mean and standard deviation for the descriptors.

Defect knowledge base 50 is preferably stored as a regular text or ASCII file that can be readily updated using a simple text editor. The defect classification computer 46 can determine if a given classification is correct within a certain confidence or certainty level, If a certain rule consistently results in misclassifications, it can be deleted.

Weight values for descriptors can be changed based on the importance a certain descriptor has in determining a classification. To ease in the adjustment of weights, weight values are stored apart from the defect knowledgebase 50 and are applied when the program is run.

Since descriptor values for certain anomalies may vary in a large range depending on the characteristic of the defect, the knowledgebase includes information about the mean and standard deviation of a range of descriptor. These values are used when an unknown defect's descriptors are compared to ones in a knowledge base.

In order to provide rapid retrieval and access to the large amount of information that may be stored in the defect knowledgebase 50 and defect image file 54, the present invention includes a method of storing, indexing and retrieving information. Instead of storing all the information about a given anomalies attributes in a database, subdirectories are created in a computer's operating system. Each subdirectory is associated with a particular piece of information regarding the anomaly. For example, the first subdirectory may represent lot number while the second subdirectory may list the xy coordinates of the defect. For example, the directory string C:\1248\23source_drain\nit_in\14.08 can be translated as lot number 1248, wafer 23 has a nit in defect in the source drain level located at x=14 and y=8. Thus substantial information can be obtained just by examining the directory information. Through the use of pointers and segmenting the directory, more information can be stored on the subdirectory. Through the use of an operating system's tree command, a linked list of the files and subdirectories can be produced in order to have a way of quickly reviewing defects. Because of its generic object oriented format, the defect index can retrieve information and images stored on different platforms at different sites.

The systems and methods introduced above will now be described in more detail.

II. ANOMALY DETECTING-AND-LOCATING SYSTEM

Figure 3:
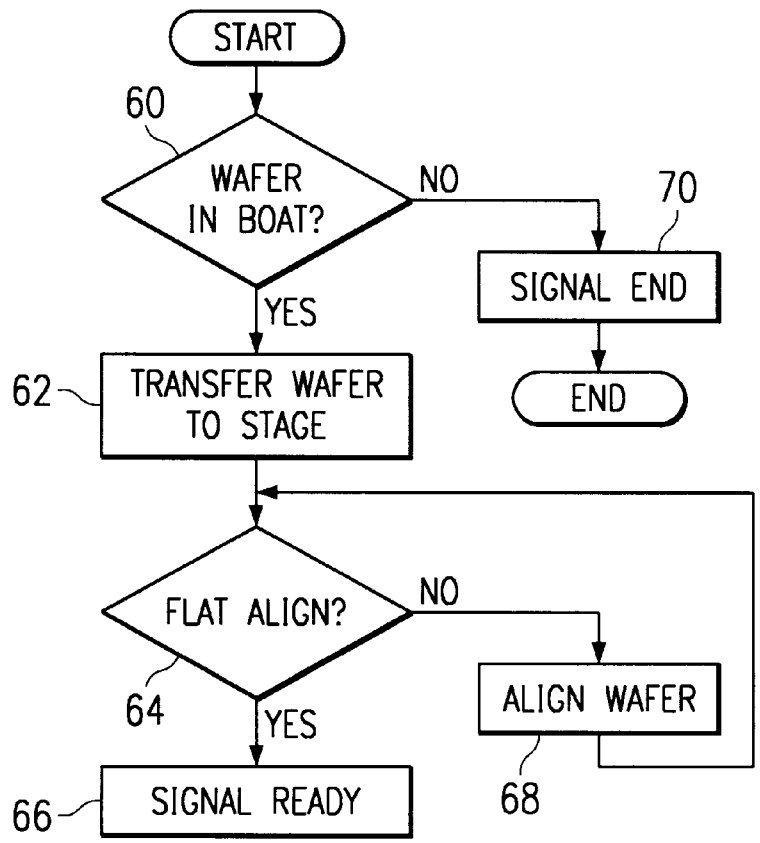
FIG. 3 is a flowchart of the wafer load program to load wafers to the stage of FIG. 2.

Referring to FIGS. 2 and 3, the anomaly detecting-and-locating computer 30 signals a wafer loader (not shown) or other device used to place a wafer 20 or other manufactured object onto the xy stage 22. First, in step 60, the computer determines if a wafer 20 is in the boat of the loader. If so, the wafer 20 is transferred to the xy stage 22 at step 62. If not, a signal is sent to anomaly detecting-and-locating computer 30 indicating the procedure is over, at step 70. After step 62, it is then determined at step 64 if the position of the flat edge of the wafer 20 is in the position on the stage 22 required in order to obtain images for anomaly detecting-and-locating computer 30. If so, at step 66 a ready signal is sent to the anomaly detecting-and-locating computer 30. If not, at step 68 the xy stage 22, under direction of the anomaly detecting-and-locating computer 30, moves the wafer 20 under the microscope 24 to a location provided by the operator or by an alignment program so that the first region of the surface of the wafer area to be used for the precise alignment of the wafer 20 comes into view on the microscope 24 and in the camera 26.

Referring to FIG. 4, there is illustrated a flowchart of the program to align the wafer 22 in order to proceed with capture of images so as to detect anomalies and provide their approximate locations to the defect classification system 2. If the anomaly detecting-and-locating computer 30 has not been directed to function in automatic mode, the xy stage 20 is moved in response to coordinates provided by an operator using an entry device such as a trackball, joystick or keyboard (not shown). These coordinates can be stored in an alignment file 32 for use when the system is operated in automatic mode. The digitizer 28 captures the image in the camera 26 and converts it to an array of pixels, or pixel-based representation of the image. The pixels are stored in the digitizer's memory or that of anomaly detecting-and-locating computer 30 or other computer.

The geometries in the image are obtained by symbolic decomposition of the image to produce a primitives-based representation of the image. The decomposition may be accomplished as described in "Apparatus and Method for Automatic Knowledge based Object Identification" Hennessey, et al. cited above, or U.S. Pat. Nos. 5,515,453 and 5,553,168, which are incorporated herein by reference for all purposes. A simplified example of the decomposition of an image as an aspect of the present invention is now described.

Figure 5:
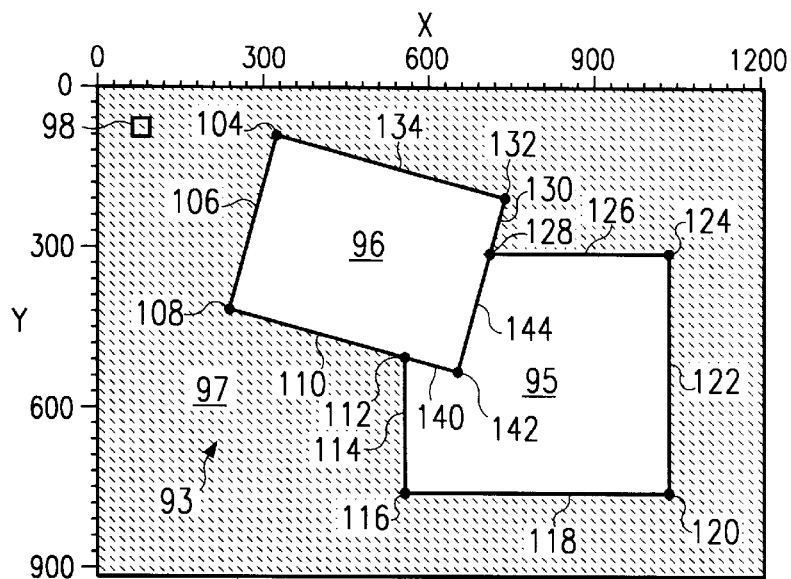
FIG. 5 is a simplified image that may be decomposed into image primitives according to an aspect of the present invention.
Figure 6:
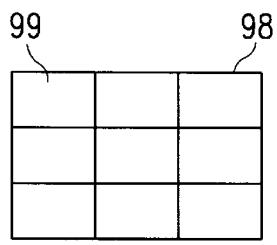
FIG. 6 is an schematic representation of a decomposition window according to an aspect of the present invention.
Figure 9:
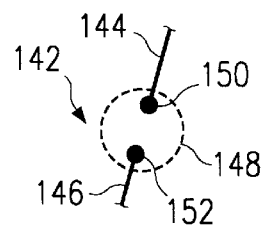
FIG. 9 is a schematic representation of two adjacent line segments from FIG. 7.

Referring to FIG. 5, decomposition window 98 is passed beginning from the upper lefthand corner (0,0) in the +X direction, i.e., to the right for the orientation shown.

The decomposition window 98 may consist of sections 99 (FIG. 6) that are used to compare pixels within different sections of deposition window 98 to determine the gradient for window 98. Decomposition window 98 may have a default search pattern that begins at the origin (0,0) in the upper lefthand corner, and traces in a search pattern in the positive X-direction until reaching the right edge of the scope-of-view window 94 (FIG. 5), at which time it returns to the left edge of a scope-of-view window 94 (i.e., x=0), and increments in the Y-direction by the width of the decomposition window 98. This search pattern is continued until a portion of an image is detected by decomposition window 98 by locating a gradient greater than background 97 by a specified threshold amount. The decomposition window 98 then traces the image, and then returns to where the trace began for that particular image segment and continues the search pattern until another segment is found. The segments that have already been decomposed are masked, i.e., the processor will not trace that aspect of the image when it encounters it later in the search pattern. This process continues until the entire window is searched or until enough information is gained for a particular process.

Upon reaching a corner 104 of a polygon 96 of an image 93, decomposition window 98 senses the gradient of a line 106 and begins tracing in the direction of segment 106, and each pixel considered along segment 106 is processed, while searching for a change in gradient which may signal a new line segment or the end of the line segment. Upon reaching corner 108, calculations for decomposition window 86 indicate or sense a change in the gradient that is greater than a predetermined gradient threshold, and therefore, line 106 is considered a single segment for decomposition purposes. For the simplified example, the primitives of the start point, end point, left texture and right texture are developed. The standard deviation and curvature are also calculated.

For the segment of line 106, the start point is approximately (330, 90) and the end point is approximately (240, 390). Moving from the start point to the end point, the texture is recorded on each side of the segment of line 106. To the left (for the frame of reference of corner 104 facing corner 108) of line 106, the gray scale value 20 is recorded and a gray scale value of 192 is recorded for the right value. Having completed the first segment, the decomposition window 98 continues along the outer trace along line 110, i.e., moves in the direction consistent with the changing gradient. The path of decomposition window 98 is in the direction consistent with the changing gradient, and if two gradients are received in window 98, the decomposition window 98 may proceed with a programmed bias to one direction or the other, e.g., seek to make lefthand traces. Additionally, in tracing the border, if window 98 reaches a dead end of a segment, after decomposing that segment, it will attempt to retrace its steps to where it last sensed other gradients within window 98 (i.e., where it had to decide which way to go), and will proceed down the other gradient. If at any time it is unable to complete a trace of the border of a complete image to return to where it started, it will do as much as possible and then return to where it began the segment and continue with the search pattern.

Figure 7:
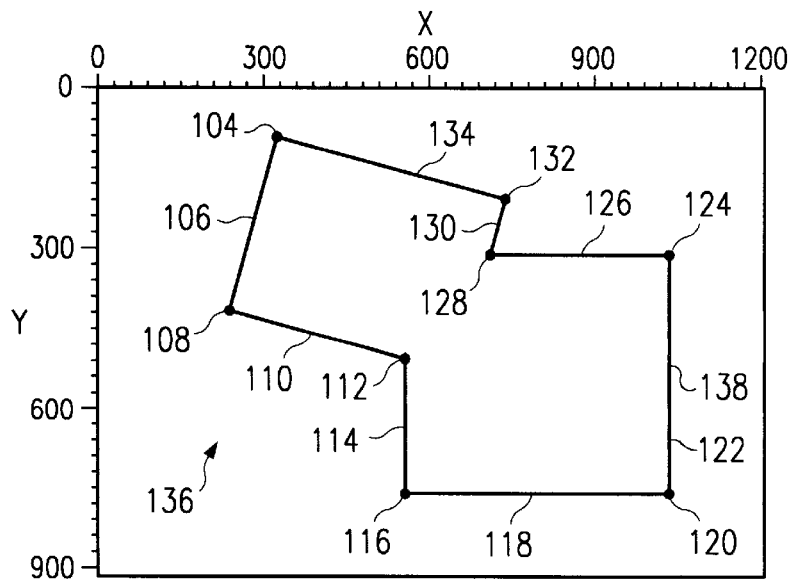
FIG. 7 is a schematic representation of the outer border of the image of FIG. 5.
Figure 8:
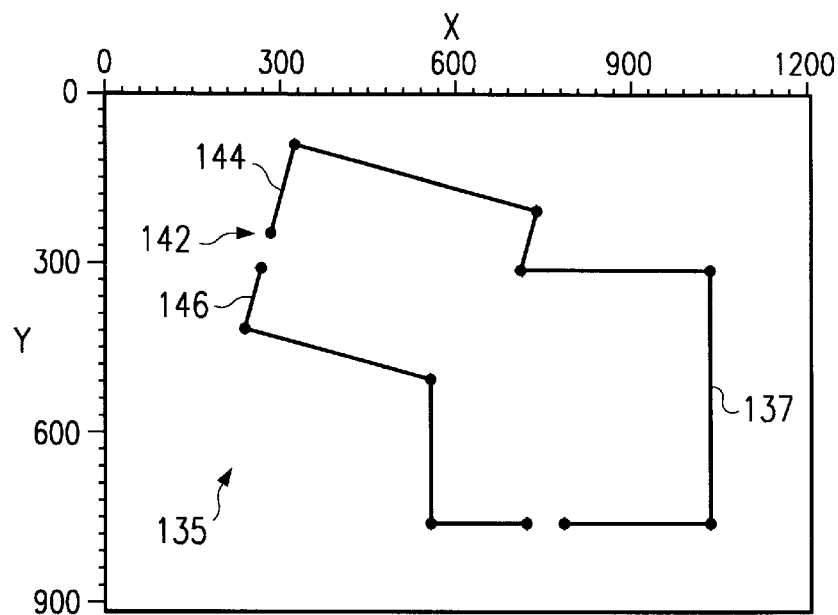
FIG. 8 is a simplified image having broken line segments that may be decomposed into image primitives according to an aspect of the present invention.

Continuing with the example of FIG. 5, upon reaching corner 112, decomposition window 98 will sense a change in gradient signaling the end of the segment of line 110. The start and stop and left and right texture information for line 110 is recorded. Decomposition window 98 senses two gradients at corner 112: The gradient of line segment 114 and the gradient of line segment 140; however, for this example, a preprogrammed bias seeking the outer most gradient has been utilized. Continuing to trace the outer border, the window 98 then proceeds along line 114 to corner 116, where a change in gradient is again sensed that signals the end of a segment. The start, stop and texture information is then recorded for line 114. The same process continues for lines 118, 122, 126, 130 and 134 with the respective corners 120, 124, 128 and 132. The trace thus makes a closed pattern ending at corner 104 as shown in FIG. 7. The following chart is thus produced for the outer trace of image 93.

TABLE I

| Line Segment | Start Point | End Point | Left Texture | Right Texture |
|---|---|---|---|---|
| 106 | (330, 90) | (240, 390) | 20 | 192 |
| 110 | (240, 390) | (550, 490) | 20 | 192 |
| 114 | (550, 490) | (550, 730) | 57 | 192 |
| 118 | (550, 730) | (1040, 730) | 57 | 192 |
| 122 | (1040, 730) | (1040, 330) | 57 | 192 |
| 126 | (1040, 330) | (710, 330) | 57 | 192 |

TABLE I-continued

| Line Segment | Start Point | End Point | Left Texture | Right Texture |
| --- | --- | --- | --- | --- |
| 130 | (710, 330) | (740, 190) | 20 | 192 |
| 134 | (740, 190) | (330, 90) | 20 | 192 |

The above chart symbolically represents the outline of the image 93 as shown by reference numeral 136 in FIG. 7. The information on the left and right texture is determined by part of the decomposition window 98 that is to either side of the gradient being followed or traced.

After having decomposed the line segments as suggested in Table I, the anomaly detection and location system masks or otherwise instructs, anomaly detecting-and-locating computer 30 to disregard the location of the line segments already decomposed, and the search for additional segments continues where the previous trace began. Thus, having started the trace of the border 138 (FIG. 7) at point 104 (FIG. 5), the decomposition window 98 returns to point 104 and continues the search pattern moving to the right. Because of masking, the next point that decomposition window 98 will pick up to trace is point 112 (just to one side of it) where line segment 140 begins. The trace will continue to corner 142 then along line segment 144 and finally terminating at point 128 again because of masking. The additional line segments produce the following information:

TABLE II

| Line Segment | Start Point | End Point | Left Texture | Right Texture |
| --- | --- | --- | --- | --- |
| 140 | (550, 490) | (670, 520) | 20 | 57 |
| 144 | (670, 520) | (710, 330) | 20 | 57 |

For the simplified image 93 of FIG. 5, the trace will again continue after masking the new line segments 140 and 144, but for the image 93, there will be no additional entries, i.e., the end of search pattern is reached (for some embodiments the search may terminate once an adequate amount of information is obtained that may be less than the entire window 94). Thus, the final decomposed image may be represented by the following table of image primitives:

TABLE III

| Line Segment | Start Point | End Point | Left Texture | Right Texture |
| --- | --- | --- | --- | --- |
| 106 | (330, 90) | (240, 390) | 20 | 192 |
| 110 | (240, 390) | (550, 490) | 20 | 192 |
| 114 | (550, 490) | (550, 730) | 57 | 192 |
| 118 | (550, 730) | (1040, 730) | 57 | 192 |
| 122 | (1040, 730) | (1040, 330) | 57 | 192 |
| 126 | (1040, 330) | (710, 330) | 57 | 192 |
| 130 | (710, 330) | (740, 190) | 20 | 192 |
| 134 | (740, 190) | (330, 90) | 20 | 192 |
| 140 | (550, 490) | (670, 520) | 20 | 57 |
| 144 | (670, 520) | (710, 330) | 20 | 57 |

Having decomposed image 93 to image primitives or descriptors or symbols, the processing of the primitives in symbolic space may begin. Note that Table III represents image 93 with a small fraction of the information required for a pixel map of the same image. To demonstrate that all of the information about the image is retained in symbolic space, the image may be completely reconstituted from the primitives using an image restoration process.

In decomposing an image, such as image 93 of FIG. 5, the ability to trace a particular aspect of an image may be impaired by discontinuities in the various line segment. Certain discontinuities may be addressed, however, during the decomposition process. For example, consider FIG. 8, which shows discontinuities developed in a trace of the border 137 of image 135. The discontinuities may be caused by any of a number of things such as noise, shadows, or inadequate contrast. During the decomposition process, consideration may be given to whether an additional gradient is sensed within a predetermined distance of the end point of the previous line segment. For example, considering FIGS. 8 and 9, for the discontinuity 142 between line segments 144 and 146, if the end point 150 of line 144 is within predetermined distance, which is represented figuratively by the diameter of circle 148, of start point 152 of line segment 146, and if the texture to the left and right of line segments 144 and 146 are fairly consistent, i.e., within a predetermined threshold, the discontinuity will be removed by generating a line segment to connect them. Thus, the discontinuous trace of the border 137 shown in FIG. 8 could be represented similar to border 138 of image 136 shown in FIG. 7.

The analysis or processing of the image in symbolic space may include any of a number of desirable operations such as enhancing the image by inference, enhancing the image by making symbolic primitive perfects, filtering noise at the symbolic level, or locating or identifying objects within the image based on a knowledgebase. Before processing an image, it may be desirable to have a knowledgebase available containing information on objects to be located or analyzed within an image.

One aspect of image processing for use as part of the invention includes grouping image primitives in a manner that allows isolation of an object in a particular image. For example, referring again to image 93 of FIG. 5 and the image primitives of Table III, which symbolically represents image 93, it may be desirable to isolate polygon 96 from other aspects of image 93. To group the particular image primitives, the left and right textures for the various segments may be compared. The segments containing the same or approximately the same left and right textures, Group I, are then considered. If an end point for a particular segment in Group I of segments, which have approximately the same textures, approximately coincides with a start point of another segment belonging to Group I, then the two segments are linked as being part of the same aspect of image 93. For example, considering line segment 106, which has a left texture of 20 and a right texture of 192, and an end point 108, this segment 106 is linked with segment 110 because they share the same left and right texture, and the end point of segment 106, point 108, coincides with the starting point, point 108 of line segment 110. Thus, in the first pass through Table III in this manner, the following line segments would be linked: line segment 106, line segment 110, line segment 130, and line segment 134. The image thus far linked does not make a closed pattern. Therefore, the analysis continues attempting to group a closed image. The next step may be to consider line segments having a left or right texture that approximately match the interior texture of the segments grouped thus far, e.g., having a gray scale of 20 for this example, for its left or right texture of the segment. Thus, the segments to be considered are line segments 140 and 144 because their left texture is 20. The process then considers whether any of the segments in this second group, Group II, has a starting point or end point that approximately coincides with the starting point or ending point of a line segment that has already been grouped. In the example, because line segment 140 of this second group has starting point 112 which approximately coincides with ending point 112 of line segment 110, line segment 140 is added to the grouped image. In a similar fashion, because segments 144 and 128 approximately share point 128, segment 144 is likewise grouped. Thus, first polygon 96 is grouped or isolated from image 93. In a similar fashion, other images, such as polygon 95, may be grouped.

Images processed in symbolic space according to an aspect of the present invention may allow for the filtering of noise. The standard deviation for the line segments may be produced. As each pixel of information is considered by decomposition window 98 during the decomposition process, running calculations are maintained to allow the standard deviation to be calculated for each segment, along with the approximation of the curvature, if any, such as by a n-degree polynomial or B-spline. The deviation may be used to filter noise from the image in symbolic space. For example, when a line segment is shown to be short compared to other line segments of the image, and to have a high standard deviation, it may be considered noise and deleted from the image primitives. In this manner, noise in the image may be removed by processing in symbolic space.

While the example given for FIG. 5 did not involve curvilinear segments, the approach is substantially the same for images with curvilinear segments. For a curvilinear segment, the start point and end point are provided along with an approximation of the curvature, which may be represented in a table by estimating the location of a mid point for a second order or other order approximation of the curve with a polynomial or by other mathematical techniques.

Geometries obtained from symbolic decomposition can be saved along with the image coordinates in an alignment file for later use in automatic mode by the anomaly detecting-and-locating computer 30 (FIG. 2). The methods that may be used to automatically align geometries of one image with those of another image of the same structure in another location are illustrated in FIG. 10*a–q*.

Figure 10A:
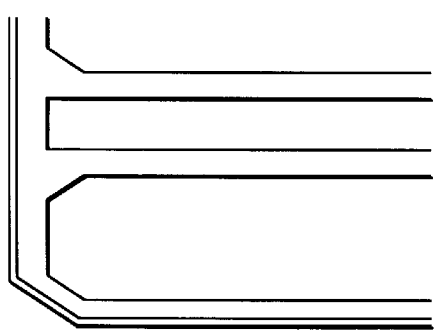
FIG. 10a illustrates a first image.
Figure 10B:
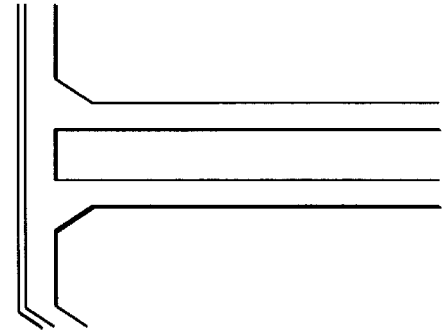
FIG. 10b illustrates a second image.
Figure 10C:
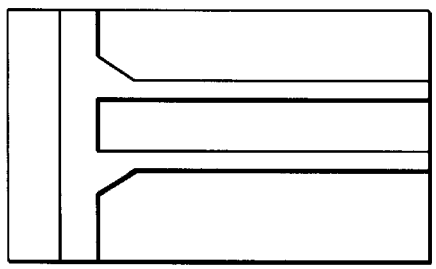
FIG. 10c illustrates the symbolic decomposition of the first image.
Figure 10D:
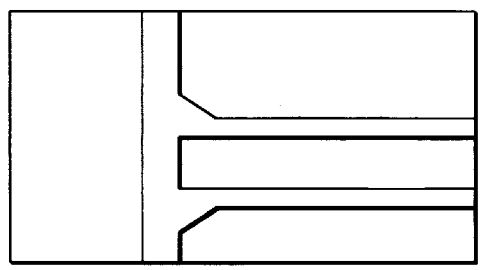
FIG. 10d illustrates the symbolic decomposition of the second image.
Figure 10Q:
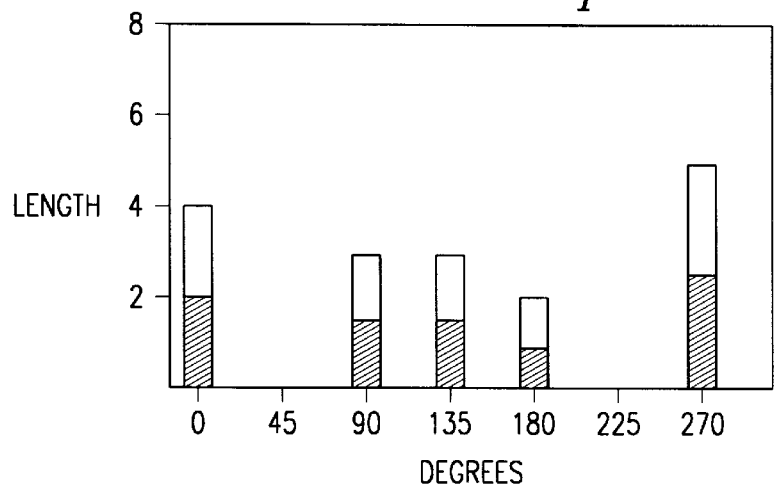
FIG. 10q illustrates histogram of second image primitives adjust to first image.
Figure 10R:
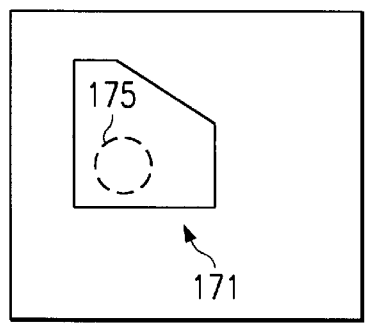
FIG. 10r illustrates a primitive-based image.

FIGS. 10*a* and 10*b* show two images of the same structure that are offset from one another; FIG. 10*c* and 10*d* show the symbolic decomposition of the images from FIGS. 10*a* and 10*b*, respectively, into FIG. 10*e* and 10*f* show how the primitives of the images aligned horizontally and vertically when compared or overlayed.

FIG. 10*g* illustrates the primitive of a first image and 10*h* illustrates the primitive of the same image rotated. From the primitives of an image, a histogram can be formed by graphing the length of an individual primitive (or a normalized length) on the y-axis and the angle of the primitive along the x-axis. Considering FIGS. 10*g* and 10*h*, illustrated in each is the same five sided figure with the FIG. in 10*h* being a rotated version of the FIG. in 10*g*. Considering a first segment 150 of the FIG. in 10*g*, it is at an angle of 0 degrees and has a length of three units. On a histogram bar graph 3 units long at 0 degrees is drawn 160, as illustrated in FIG. 10*i*. A second segment 152 is at an angle of 45 degrees and is three units long. This is graphed on the histogram in FIG. 10*i* as shown by reference numeral 162. A third segment 154 is at an angle of 90 degrees and is two units long, and it is graphed in FIG. 10*i* and is shown by numeral 164. A fourth segment 156 is at an angle of 180 degrees and is five units long which is graphed in FIG. 10*i* as 166. The angle is 180 degrees because the segments are being analyzed in a counterclockwise manner, the first horizontal line was measured to be 0 degrees so the second is 180 degrees by this convention. Alternatively, the convention that the angle must be between 0 and 90 degrees could be used. In that case the five units would be added to the length already graphed in FIG. 10*i*. A fifth segment 158 is five units long at 270 degrees. This is graphed in FIG. 10*i* as shown by reference numeral 168. The same steps can be drawn for FIG. 10*h*, and the results are shown in FIG. 10*j*.

The two histograms (FIGS. 10*i* and 10*j*) are aligned by shifting the histogram of the first image and superimposing it over that of the second image. When a large segment of the first image histogram matches a similar segment of the second image histogram (or comparison error is minimized), the difference between the angle of the first matching bar of the first image histogram bar and that of the second image histogram as in FIG. 10*k* is the angle of rotation that the image must be moved in order to precisely align the two images. As can be seen in this example, the image in FIG. 10*g* has been rotated 90 degrees to obtain the image in FIG. 10*h*.

If the primitive lengths in the reference image are not the same size as those of the current image, they can be scaled up or down proportionally until they match; this proportional adjustment gives the magnification level adjustment between the two images. FIG. 10*m* is the same five-sided image as in FIG. 10*h*. FIG. 10*n* is also the same image, reduced in size. FIG. 10*o* is the histogram for FIGS. 10*m* and 10*p* is the histogram for 10*n*. These two histograms can be overlayed and from the difference in the magnitude of the histogram segments, the magnification can be calculated. In this example, the image in FIG. 10*m* is 2 times larger than the image in FIG. 10*n* (this is calculated by taking the value of the image in FIG. 10*m* and dividing it by the value of 10*n* for a given angle. For example, at 0° 10*m* is 6 units and 10*n* is 3 units. Thus, the magnification is 200 percent (6 divided by 3 is 2)).

Figure 10S:
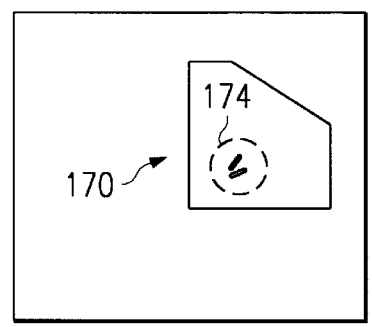
FIG. 10s illustrates a similar primitive based image with a defect.
Figure 10T:
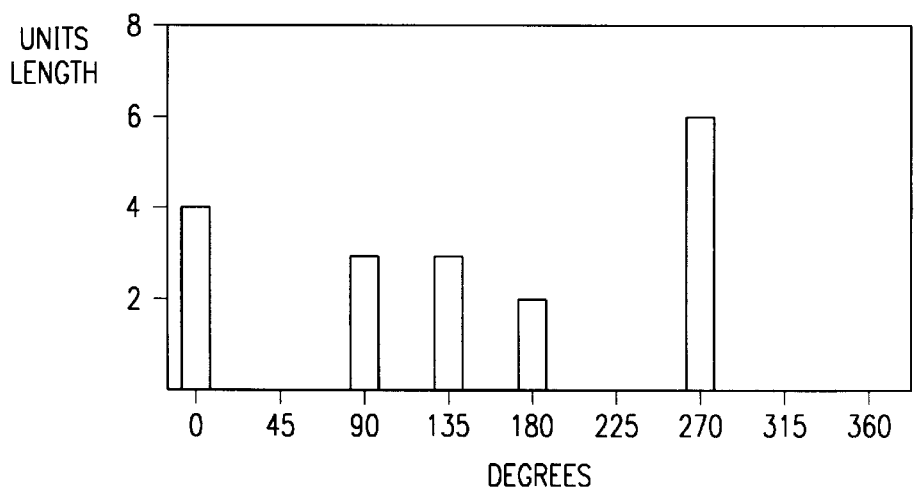
FIG. 10t is the histogram of FIG. 10r.
Figure 10U:
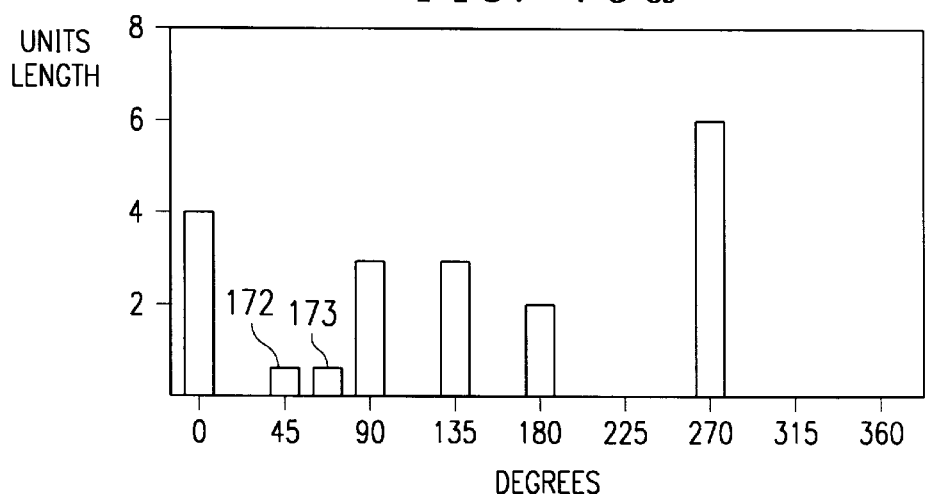
FIG. 10u is the histogram of FIG. 10s.
Figure 10V:
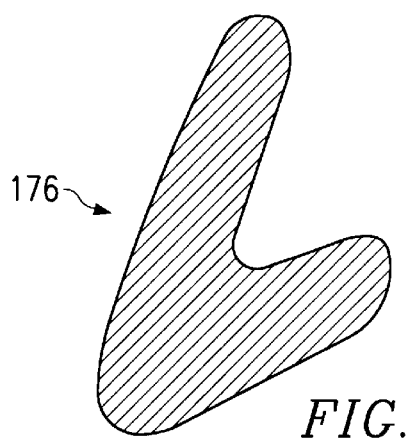
FIG. 10v illustrates the reconstructed defect.

Referring to FIG. 10*s*, a primitive-based image 170 is shown. According to an aspect of the present invention, image 170 may be compared with a reference image 171 in FIG. 10*r*, which is also a primitive-based image, to precisely locate an anomaly. A histogram is derived for image 170 according to the techniques previously discussed and is shown in FIG. 10*u*. A histogram is derived for image 171 according to the techniques previously discussed and is shown in FIG. 10*t*. In comparing the histograms of FIGS. 10*t* and 10*u* in this example—which for convenience was selected with rotation and size of the predominant objects already aligned—two primitive sets 172 and 173 are identified. The primitives associated with each may then be considered. Because the x-y location primitives for each shows them within a predetermined distance, they are regarded as one defect. The primitive information for each is used to reconstruct the image including the textures around the area as shown by circle 174. The corresponding information from the reference image, circle 175, may then be subtracted from the anomaly primitives, i.e., circle 174, such that only a precise image 176 of the anomaly remains as shown in FIG. 10*v*. Before undertaking the comparison discussed herein, noise may be removed.

Noise may be removed by comparing the histogram and recognizing that noise will have a random distribution. Thus, a baseline of noise may be recognized and removed. For example, if the histogram analysis shows that most all degrees of rotation have at least one unit, one unit is probably noise and may be removed before further analysis proceeds. Other noise reduction techniques may be used as well.

After the first alignment position is acquired, anomaly detecting-and-locating computer 30 then signals the xy stage 22 (FIG. 2) to move to the next alignment position, so that a region of the surface of the wafer 20 again comes into view of the microscope 24 and camera 26. The geometries of the object in the image are aligned with those on file for that location and the precise location of the object is again reported. This is repeated until all the alignment objects or targets have been precisely located. An xy placement coefficient or correction is calculated from these positions, which the anomaly detecting-and-locating computer 30 sends to the xy stage 22 to direct it to move so as to precisely align the wafer 20.

Figure 11A:
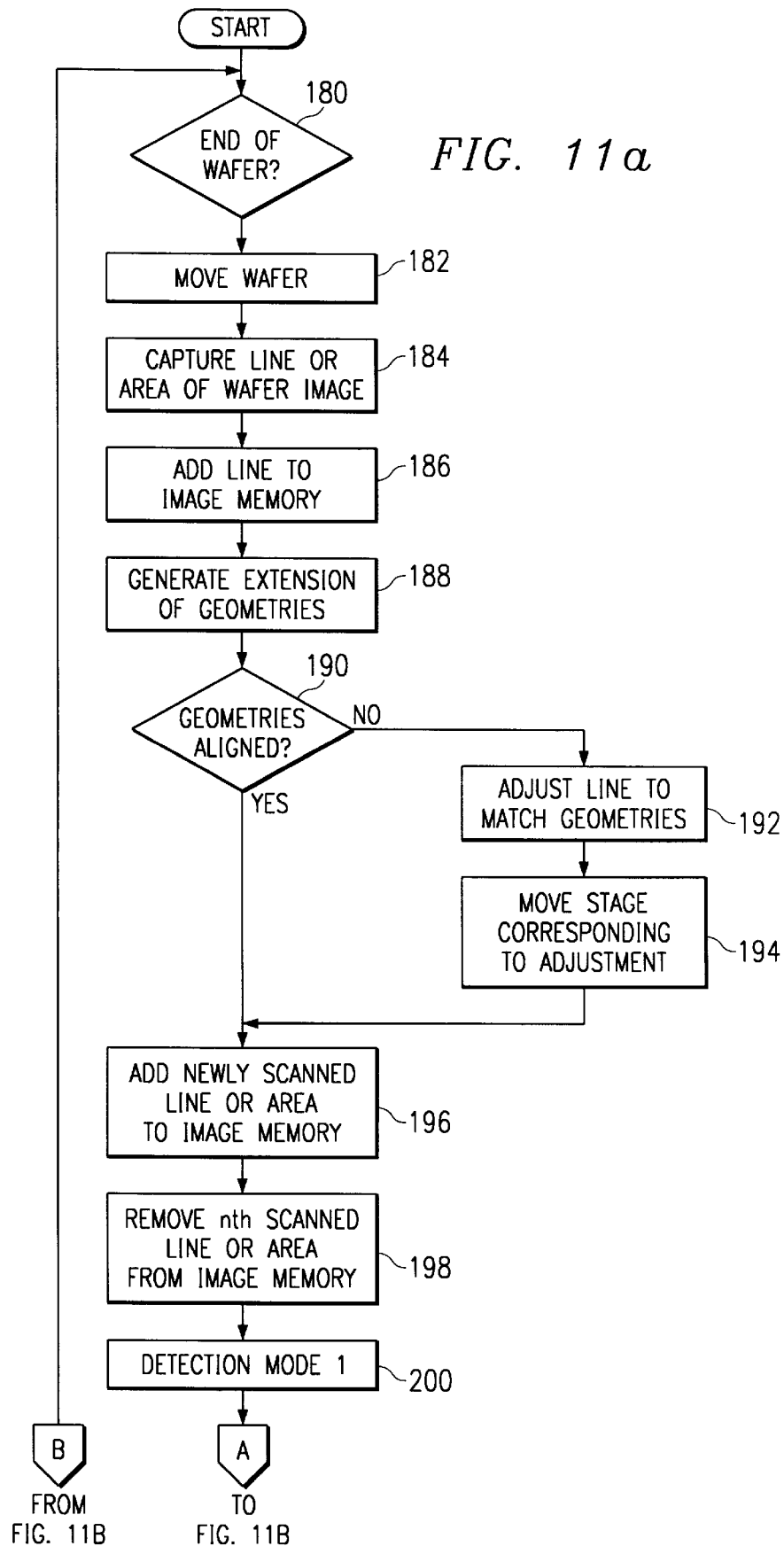
FIG. 11 is a flowchart of line scan and area scan acquisition with continuous alignment of images.
Figure 11B:
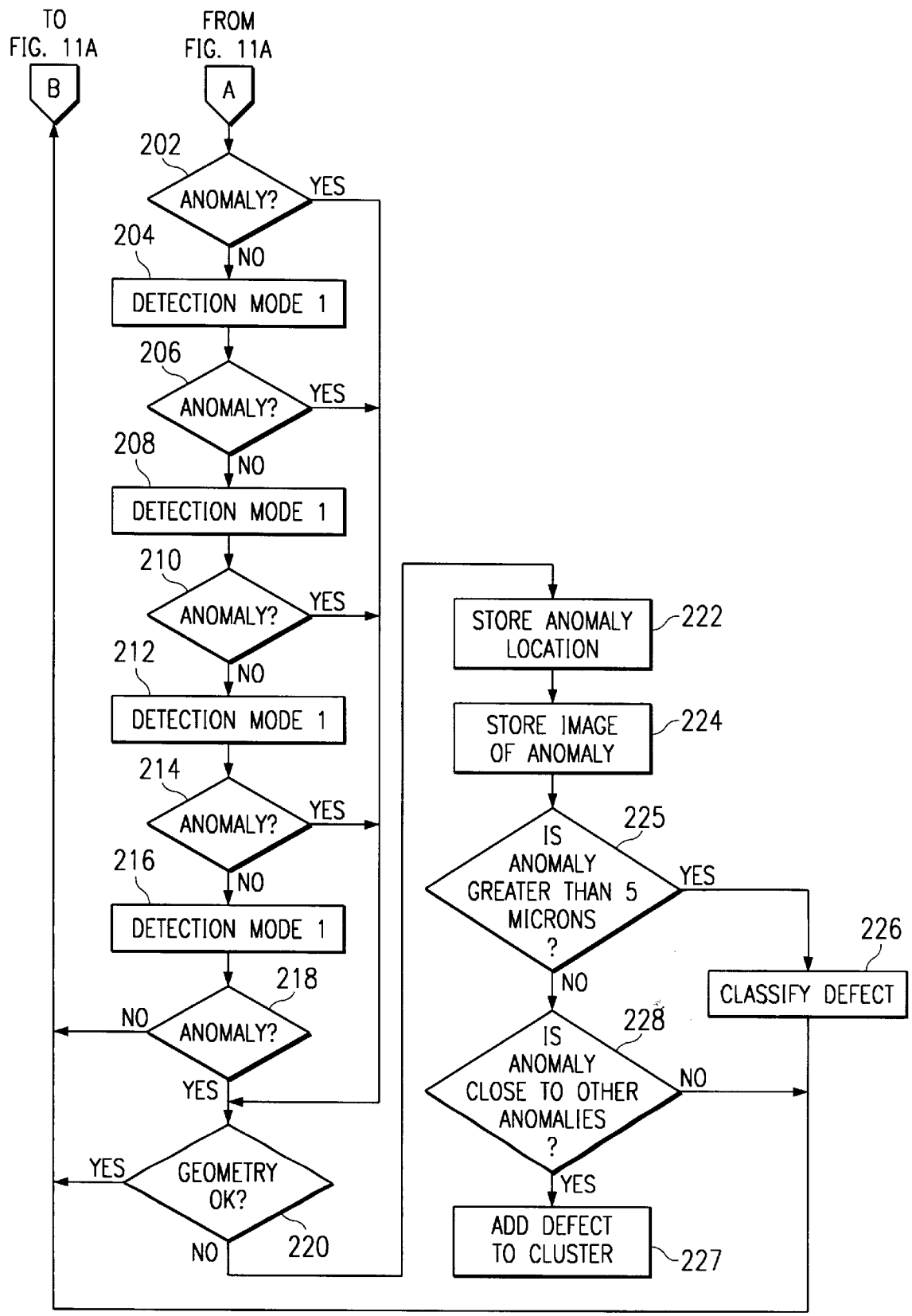

A flowchart of a program for use with or as part of anomaly detecting-and-locating computer 30 is illustrated in FIG. 11. Using, in one embodiment, a line scan or area scan camera 26 and continuously or periodically moving the xy stage 20, one line or an area of an image (step 184 of FIG. 11) of the wafer surface is captured using a low resolution microscope. The captured line or area is added to the stored image (step 186) and the image's geometries are extended (step 188). The line or area is aligned so that the previous geometries extend in the same direction or diverge sharply (e.g. at right or 45° angles, Step 190). XY stage 22 is signaled to move to correspond with the alignment adjustment. Using detection methods, which are described in detail below in connection with FIGS. 15–18, anomalies are detected (steps 200–218 of FIG. 11). If any anomaly is found, the location of the anomaly is reported. If the anomaly is found and is larger than 10 pixels, the defect is classified and/or diagnosed as discussed further below.

Figure 12A:
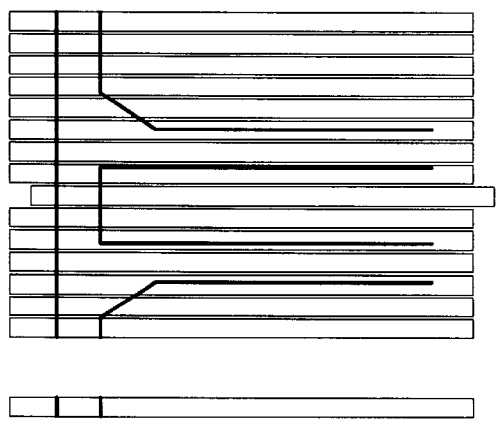
FIG. 12a illustrates construction and alignment of image from scanned lines or areas and FIG. 12b illustrates primitives symbolically decomposed and derived from the adjusted scan lines or area rectangles acquired by scanning the image.
Figure 12B:
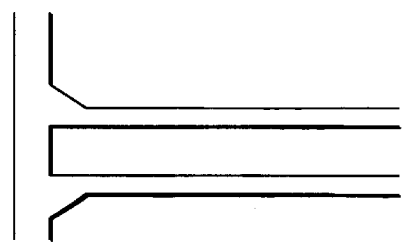

Referring to FIG. 12a, after six lines, the new line is displaced and this line is shifted which is indicated by a dashed line and extension to align the primitives that represent the geometries of the objects in the image with the end of the other six lines. This is step 190, 192, and 194 of FIG. 11. FIG. 12b illustrates primitives symbolically decomposed from the adjusted line scan image. No shifting occurs if there is a sharp divergence. Before a new line is added to image memory (step 196) an old line (n) is removed (step 198) and the entire image is shifted in memory; the new line is then appended to image memory (step 198). Detection and storing of the locations of wafer anomalies continues until the wafer has been completely scanned or until the required areas of the wafer have been scanned.

The five methods for defect reduction are now discussed in more detail. Reference is also made to U.S. patent application Ser. No. 08/347,020, entitled "Apparatus and Method for Automatic Knowledgebased Object Identification," filed Nov. 30, 1994, which is incorporated herein for all purposes.

Figure 13A:
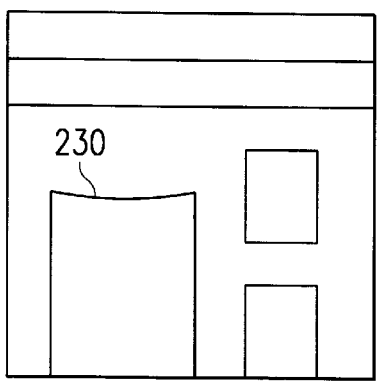
FIG. 13 illustrates examples of defects detected by Method 1.
Figure 13B:
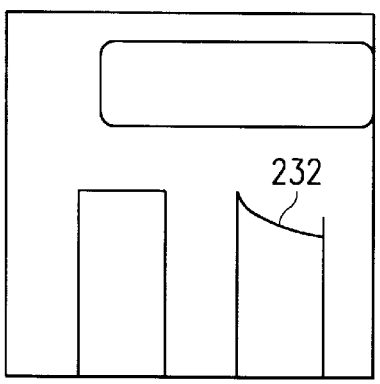
Figure 13C:
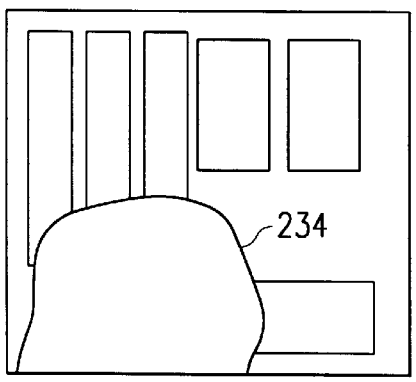

Defect Detection Method One. After decomposition of the anomaly area image into primitives and abstraction into higher-level primitives or descriptors, the first method examines the higher-level primitives for irregular angles, sudden changes (like texture changes or in a straight line), isolated objects or vague objects as shown in FIG. 13, where the image in FIG. 13a contains a structure with an irregular break 230 in a straight line, some of the structures in FIG. 13b are at irregular angles 232 to one another, and FIG. 13c contains vague edges 234.

Figure 14A:
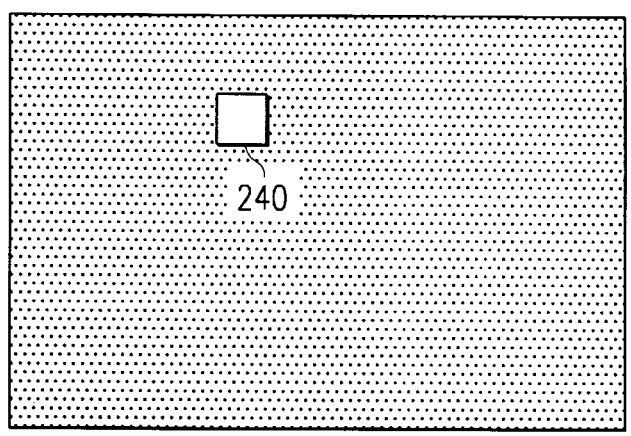
FIG. 14 illustrates defect detection according to Method 2.
Figure 14B:
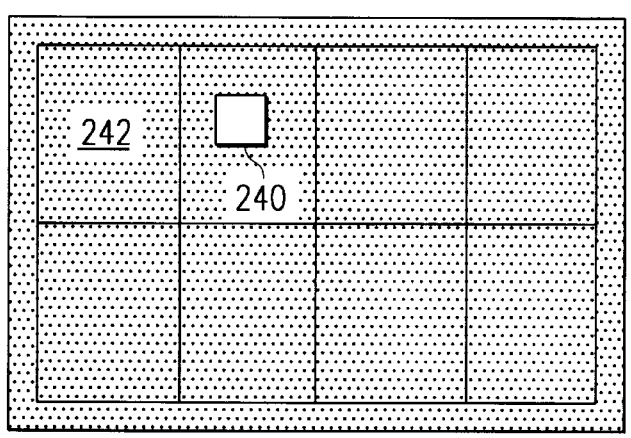
Figure 14C:
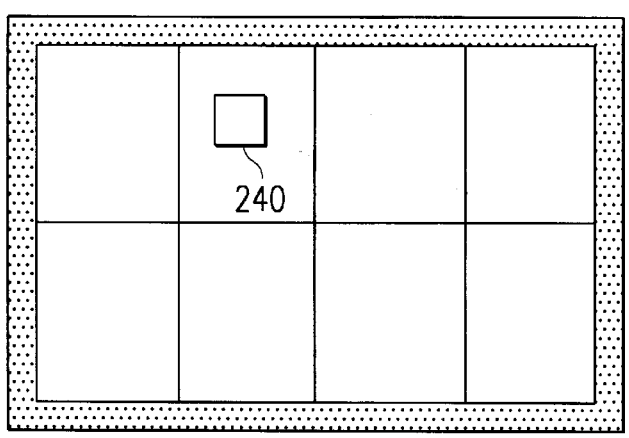

Defect Detection Method Two. If method one is not successful, then method two, which looks for a repeatable pattern, is tried. The visual pattern of many wafer types, such as memory wafers, consists of the same pattern repeated many times, known as a repetitive pattern, so the system can detect a defect using only the image of the anomaly area. This is done by examining the higher-level primitives to determine whether a group of similar primitives occurs repeatedly across and/or down the image. Illustrated in FIG. 14a is a repetitive pattern with a defect 240. To locate the defect the image is partitioned into segments 242 as shown in FIG. 14b. The contents are compared and the repeatable pattern is subtracted from each segment. This leaves an image of the non-repeated portion, which is the defect as shown in FIG. 14c.

Defect Detection Method Three. If no overall repeated pattern in the image is on a current die such as that shown in FIG. 15a, then Method Three, illustrated in FIG. 15 can be tried. This method compares the current image 252 with a reference image 254. In this method, the xy stage 22 (FIG. 2) is moved to an identical position on an adjacent die on the wafer, capturing an image—called the reference image 254 such as that shown in FIG. 15b—of the same area on the adjacent die as that of the die on which the anomaly 250 was found. Alternatively, a stored reference image can be used. The images are decomposed into primitives from which higher-level primitives are derived. The primitives are then used to align the images, using the method illustrated and described in connection with FIG. 10 or some other alignment method such as computing the major axis.

Figure 15C:
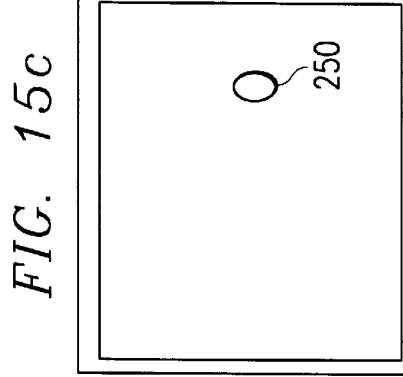
FIG. 15 illustrates defect detection according to Method 3.
Figure 15B:
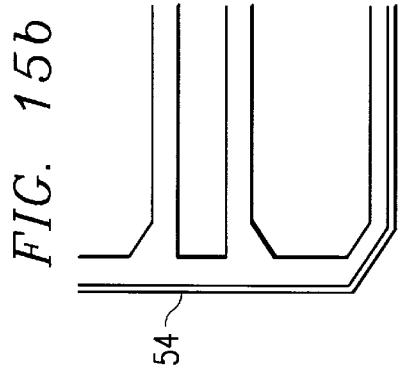
Figure 15A:
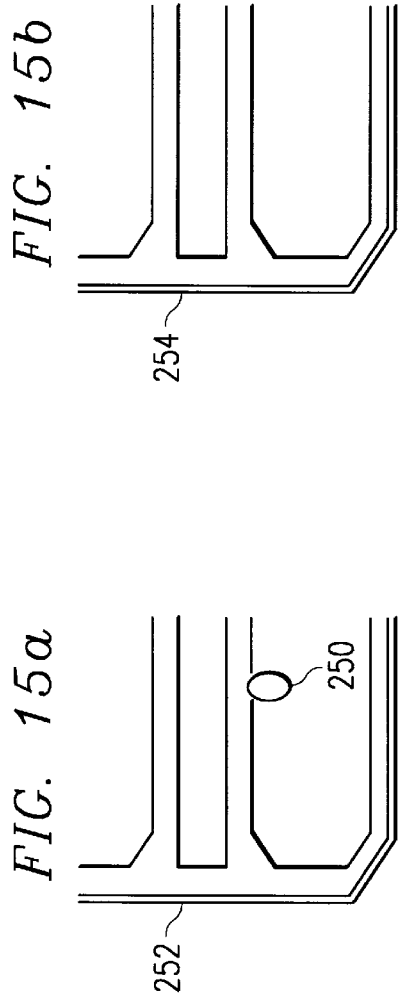

Once the two images are precisely matched, their higher-level primitives are compared to identify those that are not the same size and/or rotation, or are missing from either set of primitives. These primitives are used to precisely outline the defect area. The pixels inside this area are subtracted from the same area in the reference image, leaving the image of the anomaly 250 as shown in FIG. 15c.

Figure 16B:
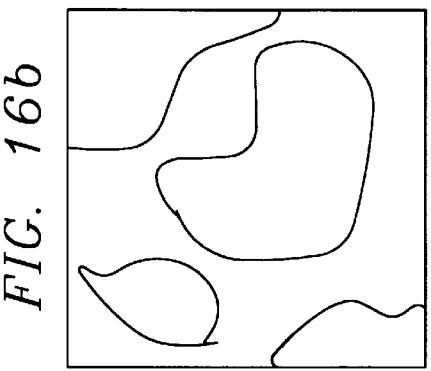
FIG. 16a illustrates no defect and FIG. 16b illustrates gross defect with no structure.
Figure 16A:
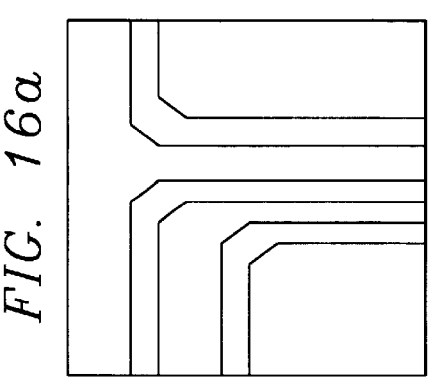

Defect Detection Method Four. If method three does not provide a clear outline and image of the defect, this may be because there is no defect or because the defect is so large that it is not possible to match any primitives. If all the primitives match almost perfectly to the reference area of the repeated structure or to the same area in the reference image, then the certainty level of an image with no defect, as shown in FIG. 16a, becomes very high. Likewise, if no primitives can be matched at all, this may be due to a gross defect such as that shown in FIG. 16b, where the defect occupies the entire image of the anomaly area.

Defect Detection Method Five. When methods three and four fail to provide a clear outline of the defect because clusters of primitives that are different in both the anomaly image and the reference image, this is usually because there are defects or striking anomalies in the reference image as well as the anomaly image. In this case, a second reference image is obtained, decomposed, its primitives are aligned, and the anomaly image is subtracted from it in the same way as described in method three above. The defect outlined in the anomaly image is the area that produces the same cluster of different primitives when both reference images are subtracted from the anomaly image.

Widescan Detection

Figure 17:
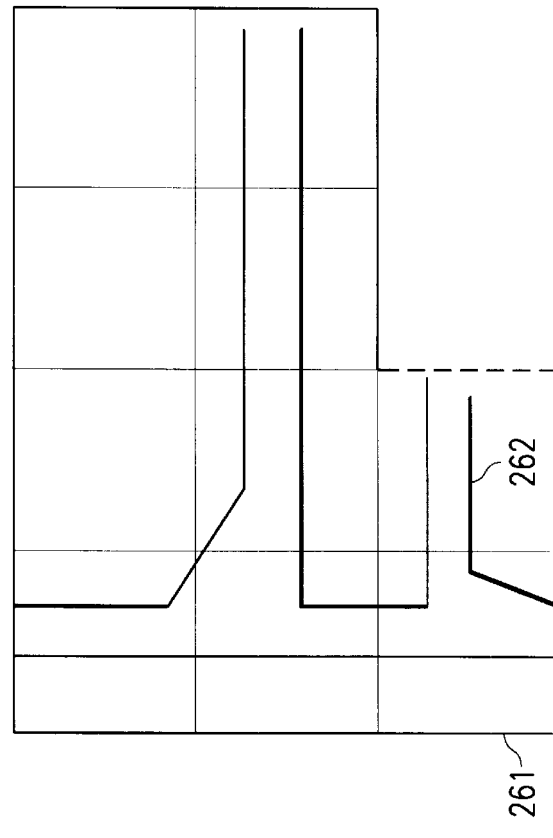
FIG. 17 illustrates acquisition of an image using a widescan camera.

In an alternative embodiment, the camera 15, can scan an area, such as a square, of a certain fixed size, such as 1000 bytes long by 1000 bytes wide. Referring to FIG. 17 a camera (not pictured) scans a first square 261. The images in that scan are decomposed symbolically by the previously described method. A second square 262 is acquired. First square 261 and second square 262 are then aligned such that the geometries of the first square 261 extend in the same direction as the second square 262. The second square is then appended to the file containing the first square 261. This continues into the entire image is acquired. The advantages of wide are scanning include faster acquisition of the image, the ability to use less intense light sources and better resolution.

Printed Circuit Board Anomaly Detection

Figure 18A:
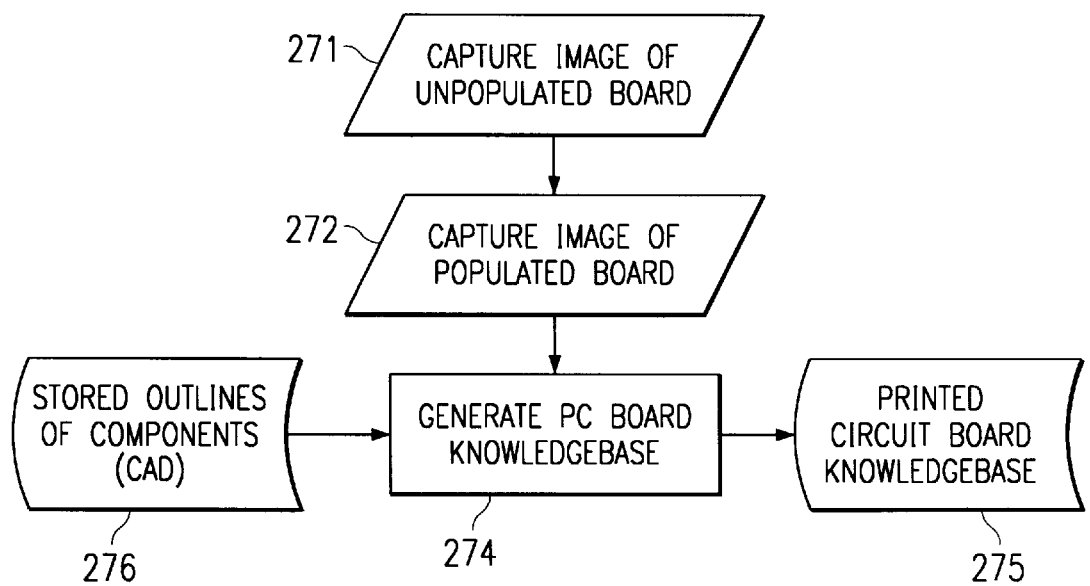
FIG. 18a and 18b are flowcharts outlining the detection of anomalies in printed circuit boards.
Figure 18B:
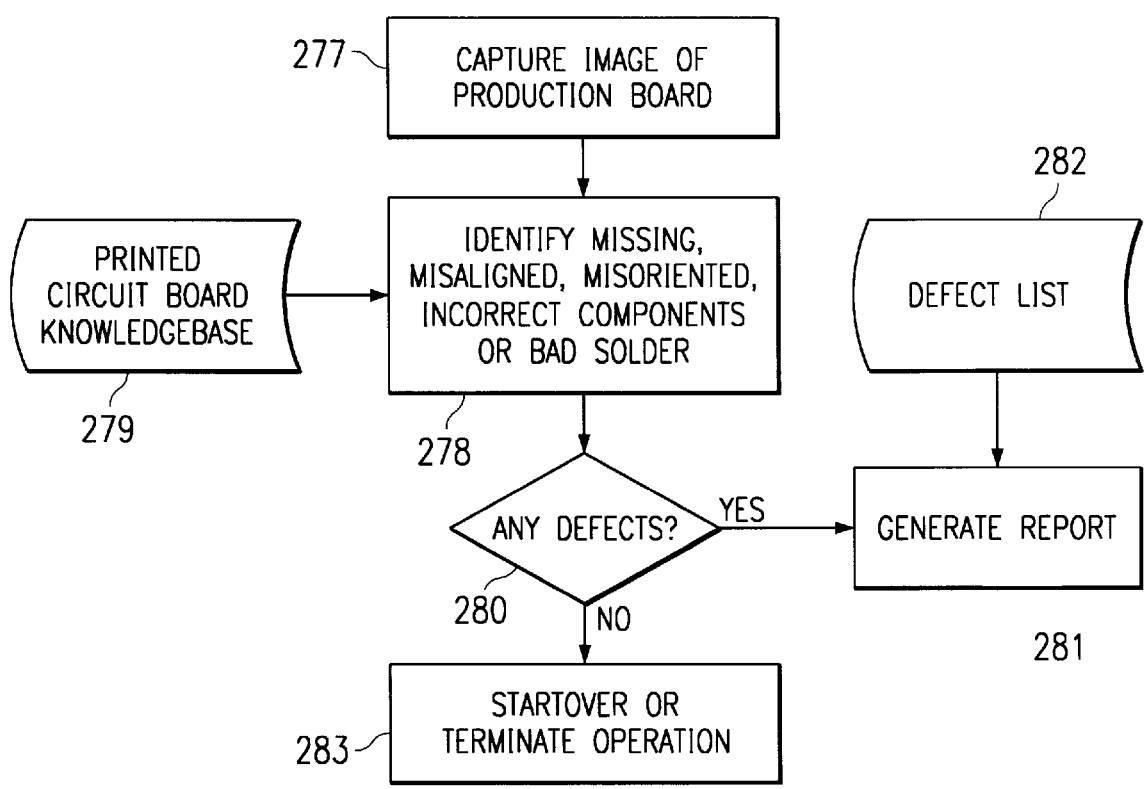

It is noted at the outset, the systems herein may be used in connection with a number of applications. An illustrative example was given in the semiconductor area. In another embodiment, defects in printed circuit boards can be detected. Referring to the flowchart at FIG. 18, in step 271 an image of an unpopulated board is acquired. The unpopulated board is simply the printed circuit board with solder marks in place as well as holes for the components, but no components are actually installed. Then, in step 272, a reference image of a populated circuit board is captured. From there, symbolic decomposition of the image occurs in step 274, a knowledgebase is generated with examples of images and/or drawings of component, the position of each component and the name of each component. This is stored in a PCB knowledgebase at step 275. Alternatively, instead of acquiring an image of the populated printed circuit board, a computer-aided design (CAD) file can be used to provide the populated image as shown in step 276. FIG. 18b outlines the technique used to search for printed circuit board anomalies. First an image of a production board is captured in step 277. In step 278, using the information stored in the PCB knowledgebase, missing, misaligned, mis oriented or incorrect components are searched for (step 278). If defects are found, a report can be generated at step 281 and the information is sent to a defect list (step 282).

III. DEFECT CLASSIFICATION AND DIAGNOSIS SYSTEM

In accordance with an aspect of the present invention, as illustrated in FIG. 2 the defect classification system 2 includes a review station computer 42 which obtains the approximate locations and sizes of wafer anomalies from the anomaly database 40. If images of defects are smaller than 5 pixels in diameter or if anomaly detection is carried out separately. The defect classification system 2 includes a defect classification computer 46 which is coupled to the review station computer 42 and may be part of the review station computer 42.

Figure 19:
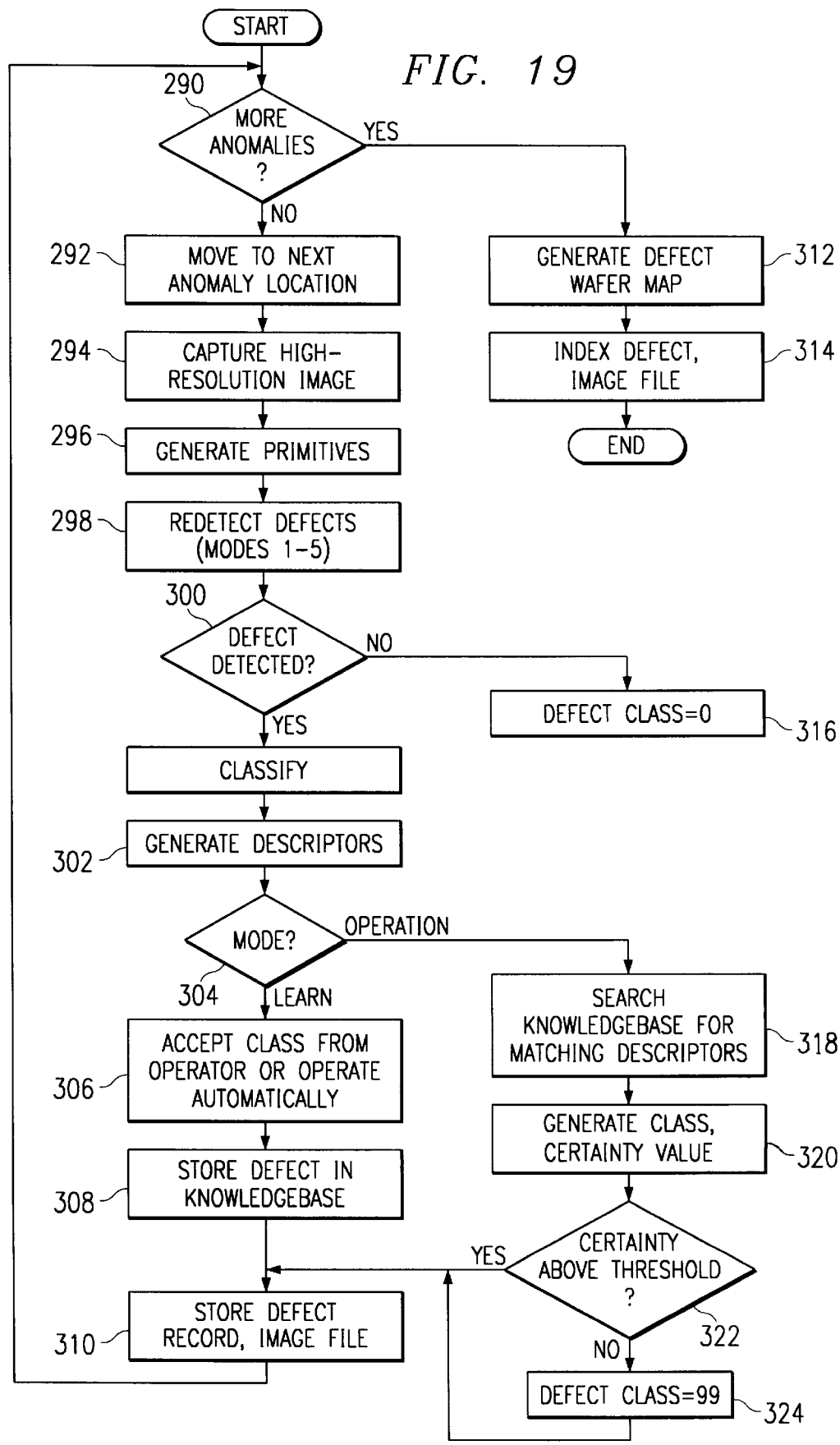
FIG. 19 is a flowchart of redetection and classification of defects.

A flowchart of a program for classifying defects is shown in FIG. 19. The defect classification computer 46 responds to instructions and other information entered by an operator at a keyboard (not pictured), in response to images and information visible on a display (not pictured) and reports generated by the defect classification computer 46 using images produced by camera 26 and digitizer 28, produces the defect location/classification file 52, and defect image file 54 from examples and rules generated by the defect classification program that are stored in the defect knowledgebase 50.

A review station computer 42 such as the Leica MIS200 manufactured by Leica GmbH, Wetzler, Germany, loads a wafer 20 on an xy stage 22 and aligns the wafer 20 on the xy stage 22 using the alignment techniques discussed above or other techniques such as that disclosed in U.S. patent application Ser. No. 08/603,026, which is incorporated herein by reference for all purposes. The same or different xy stage, camera, and other equipment used for anomaly detection and location may be used. Typically the microscope for classification of smaller defects is a higher resolution microscope than that for detection and location of defects. The camera also may be a higher resolution camera for classification and may also be designed to scan an area in a line. Alternatively, an area-scan camera can be used.

The approximate location and size of each anomaly on the wafer may be obtained from a wafer anomaly file, which is created by the anomaly detecting-and-locating system 1, and stored in the anomaly database 40. The defect classification computer 46, under control of a program with steps as shown in the flowchart in FIG. 19, signals the review station computer 42 to move the xy stage 22, on which the wafer 20 has been placed and aligned, to the approximate location of an anomaly (step 292). The review station computer 42 then signals the defect classification computer 46 that the anomaly area is in view. The defect classification computer 46 signals the digitizer 28 to capture the image in the microscope 24 from the camera 26 (step 294 in FIG. 19) that is mounted above it. The image of the anomaly area is sent to the defect classification computer 46 which analyzes a bitmap of the image by decomposing the image into primitives and assembling therefrom higher level primitives (step 296 in FIG. 19). This may be accomplished in a number of ways, but one suitable approach is to use software described in the previously cited application "Knowledge-Based Object Identification" (Ser. No. 08/347,020, filed Nov. 30, 1994, by Hennessey, et al.) which is incorporated herein for all purposes. The defect classification computer 46 determines whether the sharpness of the image is adequate to examine the anomaly; if not the defect classification computer 46 may send a focus adjustment message to the review station computer 42. When the defect classification computer 46 determines that the image is adequate, it precisely locates and outlines the defect (step 298 in FIG. 19) using one of the five methods illustrated in and described in connection with FIGS. 13 through 16. The locating methods may be enhanced by the well-known algorithm called zero crossing which has the property of eliminating random noise while enhancing very faint defects. When a defect is detected, descriptors or primitives are generated (step 302). (If not detected, the class is set for no defects, Step 316.)

At regular intervals, the contents of the defect knowledgebase 50, the defect location/classification file 52 and the defect image file 54 are transmitted along the network 38 to the defect database/archive 58 for use by the defect diagnosis system 3, including defect diagnosis computer 56. The defect image file 54 may be compressed by any one of a number of compression methods such as by JPEG compression; by fractal compression; by the image compression method described in the preceding invention "Apparatus and Method for Automatic Knowledgebased Object Identification" in application Ser. No. 08/347,020, filed Nov. 30, 1994, by Hennessey, et al.; by an image compression method in the public domain usually referred to as 'Wavelets' or by the technique discussed further below. The implementation of wavelets is known in the art.

Image Compression. The wavelet method mentioned above may give poor results at the edges of images. Decomposing an image using symbolic decomposition is useful for the edges, but does not easily represent sufficient information on the texture inside of an object in image. Combining the two methods, however, yields good results.

Referring to FIG. 20a, in step 340 an original image is acquired. Using the symbolic decomposition method as described earlier, the edges are converted into primitives and higher-level primitives in step 341. Once that is achieved, the image can be manipulated to give an image of just the edges (represented by primitives) and an image of the interior (step 342). The interior image is compressed using wavelets in step 343. The edge image is compressed in step 344 using the method as shown in FIG. 20b and FIG. 20c. FIG. 20c is a pixel by pixel representation of the primitive of an edge. In order to compress this image, the starting place of the first pixel 346 is located. In this case, first pixel 346 is initially at (3,3). The next piece of information needed to compress this image is what the starting direction is. Consider FIG. 20c, first pixel 346 is illustrated by itself The second pixel 348 on FIG. 20b can be in any one of the eight pixels around first pixel 346. The number in each of those locations is the starting direction number. In this case, second pixel 348 is in to the right of first pixel 346 and therefore has a starting direction of 0, or to the right. Once the starting position and the starting directions are found, the primitive is followed pixel by pixel. A 1 is recorded if the next pixel is directly in front of the previous pixel, a 0 is recorded if the next pixel is to the left of the previous pixel and a 2 is recorded if the next pixel is to the right of the previous pixel. Therefore, in FIG. 20b the starting position (3,3) and starting direction are recorded. Second pixel 348 is in front of first pixel 346 (since the starting direction, 0, is to the right). Therefore a 0 is recorded. Third pixel 349 is to the left of second pixel 348 so a 1 is recorded. Fourth pixel 350 is in front of third pixel 349 (since the turn was to the left for third pixel 349, the perspective is now in that direction). Following around the rest of the image, the following information is obtained.

| Starting position | Starting direction | pixels |
|---|---|---|
| (3,3) | 0 | 101121213 |

The final three indicates the end of the primitive. Finally the compressed interior and compressed edge information is stored as a file (step 345).

Defect Classification. The ADC or automatic defect classification system is described in detail in application Ser. No. 08/347,020, filed Nov. 30, 1994, which has been incorporated herein for all purposes. Referring back to FIG. 19, once the defect is outlined and a bitmap of the defect area is isolated, the defect classification system generates a set of high-level descriptors (step 302 in FIG. 19) from the primitive representation of the defect, each of which is a numerical value that represents a relevant visual characteristic of the defect area of the image, such as: color, size, edge sharpness, eccentricity, roundness, transparency, texture, contrast between surrounding image and image of defect, etc. Each defect is represented in a record that contains a value for each descriptor; this description record uniquely characterizes the image of that defect. Additional details of construction and use of the description record are described in application Ser. No. 08/347,020.

The defect classification computer 46, having converted the bit map of the defect image and, in certain cases, one or more reference images, into higher level primitives and aligned the images to each other using these primitives as described under method three above, operates the system in either classification learn or classification operation mode.

Classification Learn Mode. When in learn mode (step 304 of FIG. 13), the expert operator or the automated knowledgebase analyzer 48 selects images that are typical examples of each type of defect and provides a classification number for each example (step 306). The defect description record for each selected example is stored in the defect knowledgebase 50 (step 308) as a rule and a compressed version of the image of the defect is stored in the defect image file 30 (step 310). An inspector (skilled person or expert) may also provide a name that is to be associated with a defect class number in a defect dictionary stored in defect location/classification file in file 52, by selecting a particular defect and then entering a number along with an identifying name such as, "metal_1_extra_patt". Thus a class of a defect (the number in the far left column in Table IV below) is the number associated in the defect dictionary file in file 52 with a defect name such as "metal_1_extra_patt" that is given to each in a group of similar examples of the defect images by the inspector. The defect image is compressed, given a file name as shown in the second left column in Table IV, and stored in the defect image file 54.

Compression of the image of the defect, as discussed previously, can be done using a three step method: (1) subtracting the images of the primitives that have already been generated by the symbolic decomposition program—which represent the image in its spatial domain—from the defect image; (2) compressing the remaining textures using the "wavelets" method to describe the remaining textures in the frequency domain; and (3) encoding the data representing these primitives and wavelets coefficients so as to compress them further. This compression technique is illustrated in FIG. 20. The encoded, compressed version of the image of the defect and the anomaly area immediately surrounding the defect is stored in the defect image file 54. Other methods can be used to compress images including JPEG compression, fractal compression, or wavelet compression.

Table IV contains an example of how the contents of a defect knowledgebase 50, created by an operator, may be stored. It shows that each line of text—or knowledgebase rule—contains a set of descriptor values generated from an image of a selected example defect, along with other information such as the defect class, the detection method, and the name of the file in which the image of the defect is stored.

TABLE IV

| Defect Class | Detection Method | Image Filename | Size | Color | Sharp edge | Eccentricity | Texture | Smooth edge |
|---|---|---|---|---|---|---|---|---|
| 4 | 5 | mtl2-44 | 48 | 11 | 137 | 64 | 54 | 81 |
| 15 | 5 | ply1-38 | 193 | 28 | 22 | 82 | 11 | 37 |
| 4 | 5 | mtl2-94 | 53 | 13 | 181 | 68 | 51 | 66 |
| 15 | 5 | ply1-11 | 205 | 16 | 29 | 98 | 23 | 24 |

Alternatively, the descriptor records of the examples of each class of defect stored in the defect knowledgebase 50 may be condensed by an assimilation method, described below, or by any other method of generalizing or emphasizing the descriptor values for each class of defect. One assimilation method analyzes the descriptors in the example defect records in the defect knowledgebase 50 using fuzzy logic, statistical correlations, and other well known methods as well as mapping the defect descriptors in feature space, in order to provide a single or small set of defect descriptor records for each class of defect. Details of procedures for creation, evaluation, and alteration of the defect knowledgebase 50 are given below under knowledgebase creation, maintenance and optimization and are illustrated in the flowchart in FIGS. 39 and 40.

Classification Operation Mode. When in operation mode (step 304 of FIG. 19), the defect classification computer 46, under program, control searches and compares the descriptor values (step 318) of the detected defect (which are stored in the defect description record) to the descriptor values of example defects in the defect knowledgebase 50 and determines which group of defect examples with the same class number, when their descriptor values are mapped in feature space, are closest to the position in feature space of the descriptor values of the detected defect, giving the highest certainty value. The exact way this is done is discussed in the knowledgebase creation, maintenance and optimization section below. If the certainty value is above a predetermined threshold, this class number is selected (step 322) as the classification identifier of the detected defect and stored in the defect record (step 310), along with other information about the defect such as its location and the location of the compressed defect image file, in the defect location/classification file 52. At regular intervals each defect record in the defect location/classification file 52 is transferred to the defect database/archive 57 where it may be indexed by location, class, lot, wafer, layer, die and other relevant characteristics of the defect. If the certainty level is below a predetermined threshold, it is classified as 99 or unclassified (step 324). This signals the operator that the operator should examine the knowledgebase.

Figure 21:
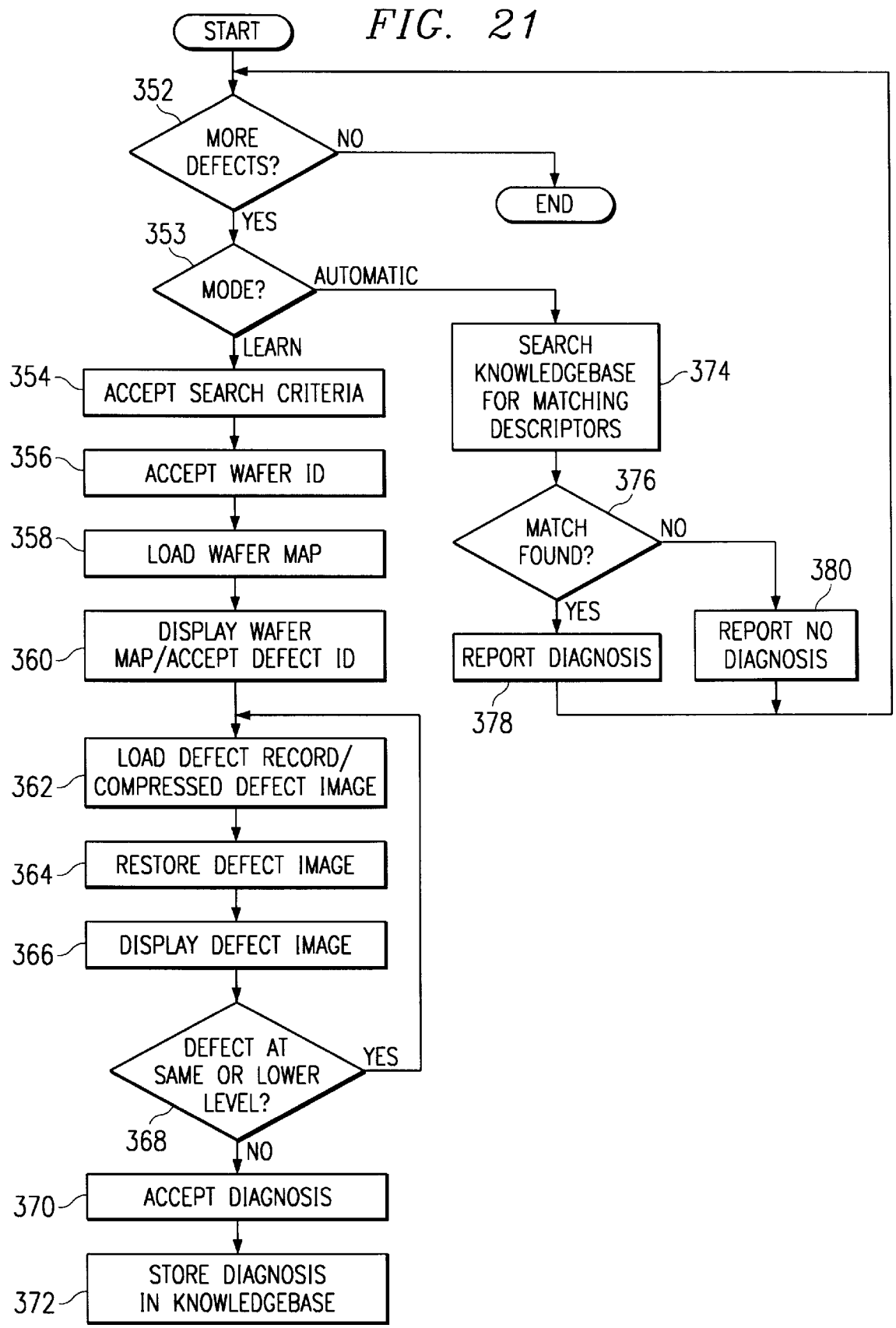
FIG. 21 is a flowchart of the diagnosis operation according to the present invention.

Automated Defect Diagnosis. One of the specialized types of defect classes by which example defects may be grouped is the diagnosis, or cause, of the defect. The defect classification discussed above assigns a defect-type label to a defect, but it is also possible to use the systems and methods discussed herein to diagnosis the source of the defect or assign a defect-source label to the defect. Referring to FIG. 21 and using the learn mode (step 352) like that described above for classification, the expert selects examples of defects along with a classification number to represent the cause or diagnosis of the defect. Reaching a correct diagnosis may not be possible for some time after the defect has been detected and initially classified and different experts may be involved in making the determination of cause of the defect.

Referring to FIG. 21, there is a flowchart of the diagnosis program. The operation to diagnose defects is similar to that to classify defects. If the processor is operating in automatic mode or unsupervised mode (step 353), the defect knowledgebase 50 searches for diagnosis records (step 374) with sets of nearly matching descriptor values and, if found, (step 376) uses the diagnosis number to retrieve the diagnosis name, which is then reported (step 378). If in learn mode, the search criteria (step 354) such as lot, date, device, position, shape or size of defect is obtained from the operator. All records that meet the search criteria form are retrieved from the defect knowledgebase 50. Summaries such as graphs and statistical defect analyses generated from the contents of these defect records are displayed and defects are listed by wafer numbers, lots, and other criteria for selection of an individual defect. The defect locations can be displayed on a computer representation of a wafer map, so that the operator can select a specific defect by pointing to the location on the wafer map using a pointing device such as a trackball, mouse, or light pen. The name of the file containing the compressed image of the defect can be obtained from the defect record as shown in Table IV, shown previously. The compressed image of the defect can be retrieved, restored and displayed (steps 362, 364, 366) to assist the operator in determining the diagnosis of the defect, which is then entered on the keyboard (steps 370, 372).

Some classes of defect, such as "metal_missing" or "open" that occur on one layer are frequently caused by another defect such as "particle" on a previous layer. The defect diagnosis computer 56 may be programmed to provide an "electronic peelback" (analogous to the current practice of chemical peelback which removes several layers to reveal the original defect). Referring back to FIG. 21 and starting with the topmost available layer, the defect database/archive 58 index is searched to find defect records that match the search criteria (step 354) and the locations of all defects on that layer of the wafer is retrieved (step 356). They are then displayed on the wafer map so the operator can select a specific defect as described above (steps 358). The records of all defects occurring at the same location on previous layers at the same location (steps 360, 362, 364, 366) are also retrieved. When the operator selects another layer, the image of the defect at that layer (step 362) from the defect image file 54 is retrieved, restored and displayed (steps 364, 366) along with other details of the defect obtained from the defect record retrieved from the Defect Knowledgebase 50. Thus, the operator can electronically "flip" through the images of defects at lower layers so as to determine if the actual cause of a defect that appears at a higher layer occurred on a previous layer.

As shown in the flowchart in FIG. 21, in order to determine whether the cause of a detected defect is due to another defect in a previous layer, the automated diagnosis procedure operates to read the defect records (step 362) of those defects detected nearby in previous layers and load them along with restored version of their compressed images (steps 364) retrieved from the defect image File 50 into a small local database (e.g., in one embodiment, Microsoft Access, manufactured by Microsoft is used) for handling the information. The wafer map generated from these records gives the locations of the defects as displayed in FIG. 22, so that the operator can enter the selection of a defect (steps 360) and display the defect image (steps 362, 364, 366). The computer then searches for defects with same location on the wafer in lower layers (step 368) to determine whether a defect record exists for that same location and if found display the previous layer (steps 362, 364 366) and search for defects. If there are no defects, the system reports this. From this, the operator can determine and enter a diagnosis of the cause of the defect (step 370), which is then stored as a rule in the diagnosis knowledgebase (step 372). In automatic mode, the diagnosis system functions as in defect classification operation mode (see FIG. 19) and produces the diagnosis. Analysis of the defect description records can also provide this information to defect classification system 46 such as statistical information by lot on the types of errors (nit-im_particle, unknown_class, p1-p2_particle, current_particle, unclassified, undetected_p2-stack_particle, stack_bpsg_part, missing_moat, im-p1_particle, stack_short, missing_contact, missing_metal) also information on classes by level, defects by level, electrical results, defects by lot, and class by lot.

Figure 22A:
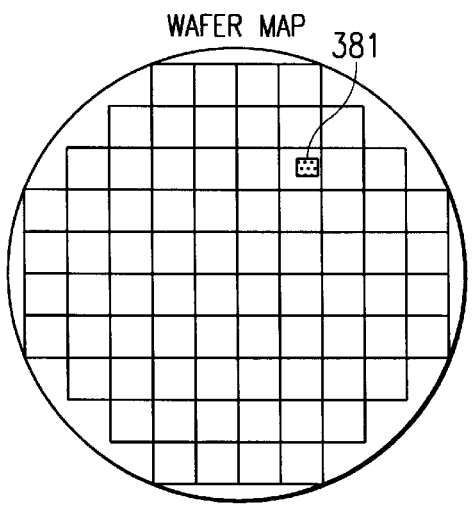
FIG. 22 illustrates a wafer map with defects.
Figure 22B:
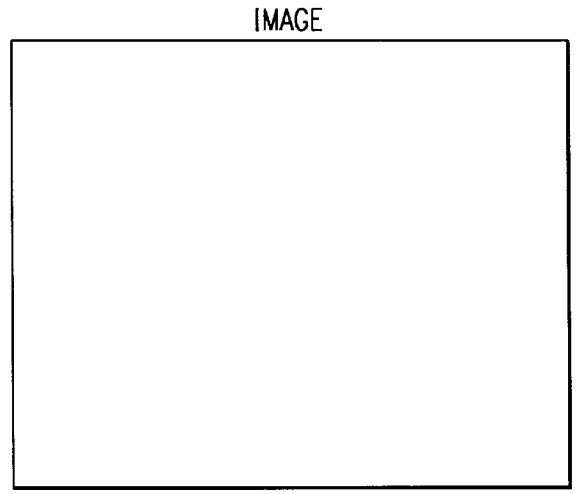
Figure 23A:
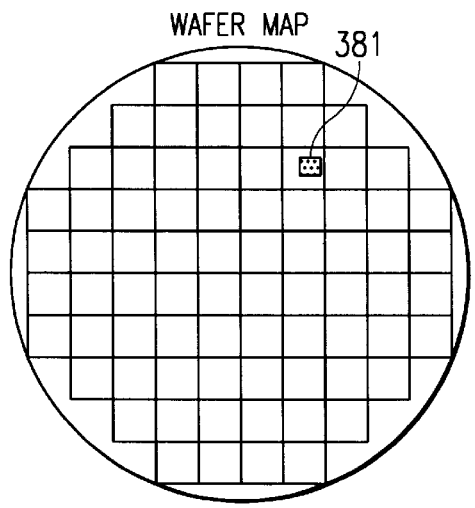
FIG. 23 illustrates selection of a defect and retrieval of an image of that defect from the defect imagebase on a given layer.
Figure 23B:
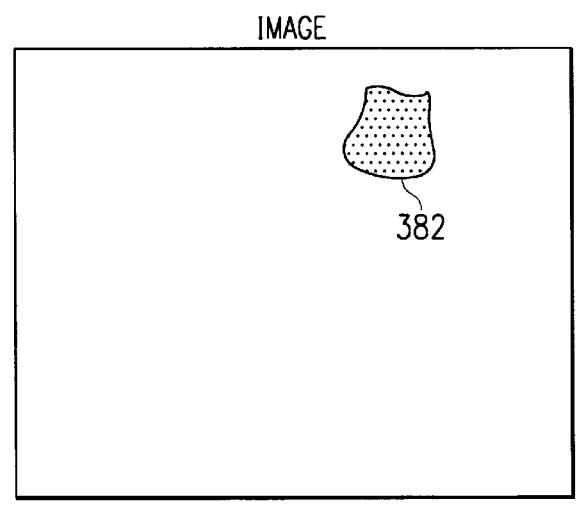

Considering FIG. 22*a* and 22*b*, they illustrate a wafer map (FIG. 22*a*) and an image screen (FIG. 22*b*). This is what would be displayed on an operators screen when performing an electronic peelback or other classification procedure. Initially there is only a wafer map showing the location of a defect 381. Initially, the image has not been retrieved. FIG. 23*a* and 23*b* illustrate an operator's screen at another layer. Illustrated at FIG. 23*b* is an image of the defect 382. In FIG.

Figure 24A:
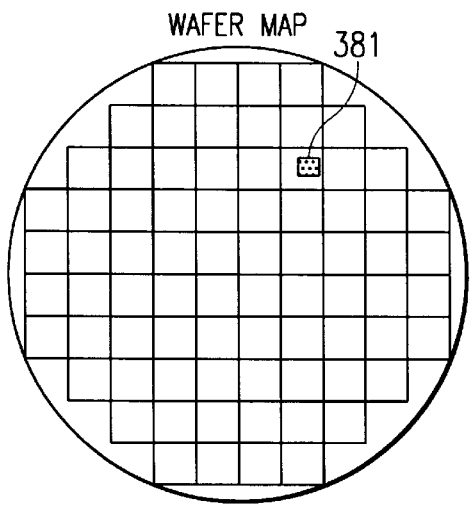
FIG. 24 illustrates an image of the same location on a previous layer to that in FIG. 23 on the same wafer.
Figure 24B:
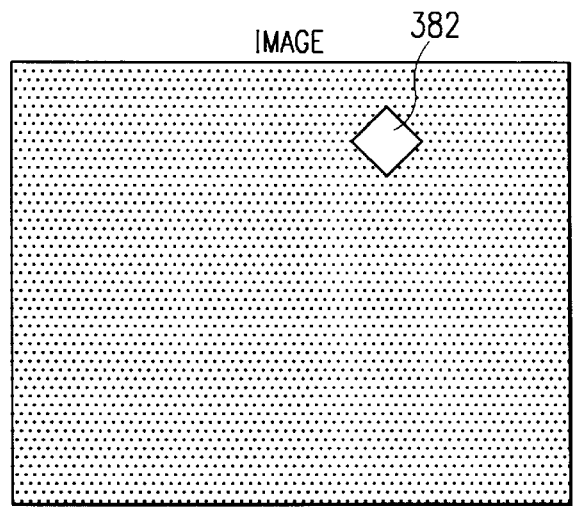
Figure 25A:
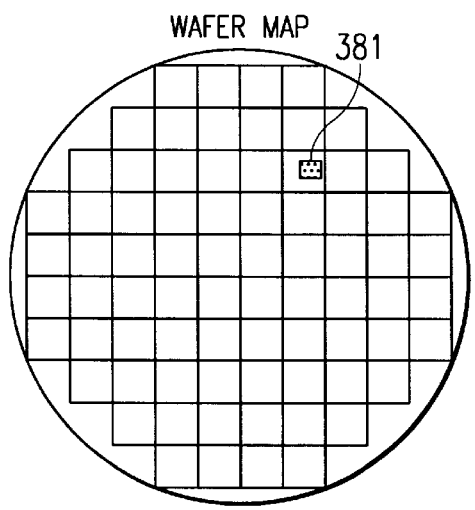
FIG. 25 illustrates another previous layer with no defects.
Figure 25B:
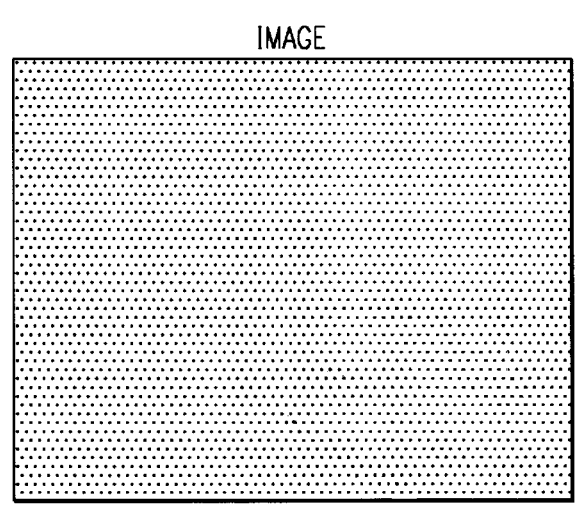

24a and 24b, the next level is shown. FIG. 24b shows that at this level, the wafer has a repeatable pattern. Defect 382 is shown to be a missing pattern defect. FIG. 25a and 25b show the next level down. As can be seen in FIG. 25b, no defect exists at this level. An operator using electronic peelback can therefore see a defect at the first level at which it appears (FIG. 23b) and go down to the next lower level to ensure that the cause of the defect is located at the former level.

IV. Automated Defect Repair

One use of the stated method of defect classification and diagnosis is to classify a detected defect as either repairable or not repairable, or "in tolerance" or "out of tolerance." The repairable or not repairable information, along with an image of the anomaly area and the detected defect, is integrated with information produced by a repair tool to produce a precise location and image of the repair and repair instructions for the repair tool. After the repair has been done, the automated defect repair system 4, (FIG. 2) captures an image of the repair, analyzes the repair to determine whether it has been correctly completed, decides whether to direct the repair tool to make another repair attempt, and may report the status of the repair to the yield management system 5 (FIG. 2).

Referring to FIG. 26, an example of the repair process is shown. It begins with detecting and providing the approximate location of defects at step 440. The next step 442 is classification of the defects as repairable or not repairable according to examples of defects stored in a knowledgebase. In the next step 444, a magnified image of the defect area generated by the repair tool is used to redetermine whether a defect is repairable, and if so, to generate a precise image of the repair (step 445). The repair is attempted in step 446. An image of the repair is captured and analyzed to determine whether the repair has been successful or unsuccessful, whether the repair has caused damage to the area around the defect, and whether to attempt another repair, at step 448. If the repair was unsuccessful, another attempt can be made (step 449). At the end, a check repair step 450 is performed.

Referring to the block diagram of FIG. 27, a wafer defect detector 460, such as the Surfscan AIT manufactured by the TENCOR Corporation or the KLA model 2132 of KLA Instruments Corporation or any other wafer detect detector, detects defects and reports their approximate location on the wafer. Any device that provides the location of each defect within a radius of 150× the width of the smallest defect to be detected may be used. An automatic defect classification (ADC) program, running on a connected review station 464 with a microscope, xy stage, camera, and processor (defect classification computer 46 in FIG. 2) such as a standard PC equipped with an image capture circuit board and loaded with DOS/Windows or other operating system and the ADC program which operates in a manner discussed above is provided.

Referring to FIG. 2, in the wafer anomaly detection and location system 1, a semiconductor wafer 20 is placed on an xy stage 22 so that an area of the wafer is illuminated by an energy source 25 that can produce energy such as white light, polarized light, laser refraction, scanning electrons or X-ray. The anomalies on the wafer are detected, usually with a microscope 24, a camera 26, and a digitizer 28 or other means of converting the image of the anomaly from analog to digital form in order to supply a digitized rendering of the image for the anomaly detecting-and-locating computer 30. This produces, under program control, information about the anomaly, such as its approximate size and location, which is stored in the anomaly location file 34. An image of the anomaly may also be stored in an anomaly image file 36. These files are transmitted via a network 38 or other means to an anomaly database 40 where the files may be retrieved by other stations and systems connected to the network 38.

The program operates with the review unit 464 to precisely locate and classify the defects as either repairable or non-repairable. This information is stored in a results file (466 of FIG. 27), which contains the precise coordinates of the defects with the defects flagged as repairable or non-repairable, and their images in a digital image format. As this data can be very large in volume, it may be compressed and stored on a network server or other mass storage device. A defect repair unit or tool, such as a MICRION 9800 ion beam machine (468 of FIG. 27), is ready to repair a defect when it obtains the precise coordinates of the repairable defects and generates a magnified image of the defect. An ADR (automated defect repair) program aligns and magnifies the original defect image so that it is superimposed over the repair unit image of the same defect. It obtains a reference image of the same area from an adjoining die or from a CAD file (provided, in one embodiment, from the defect management system 472 or the review station 464), outlines the defect, and generates a repair bit map of the precise area of the defect for which metal is to be removed or added. MICRION 9800 is a product of MICRION Corporation, One Corporation Way, Peabody Mass. The precise outline, or bitmap, of the repair is sent back to the MICRION repair unit, which activates the MICRION focused ion beam to either lay down metal ions or to burn out metal ions. When the repair is complete, another image of the defect area is generated. The ADR program system determines whether the repair has been successful and classifies the defects as repaired, un-repaired, or damaged and stores the repair image along with the ADR results.

The ADR program determines whether to repeat or abandon the repair attempt and whether any damage to the area has occurred during the repair attempt. These results may be reviewed at any time, at a review station 467 (of FIG. 27) so that the process can be monitored. The image of what has to be repaired is then classified as repaired or non-repaired, repaired but ruined, etc.

Referring to FIG. 26, a flowchart is shown for the repair process according to one aspect of the present invention. Alternatively, the repair process may be considered to include the nine steps listed below.

Step 1: Capture and align the optical defect image to the optical reference image.

Step 2: Precisely locate, outline, and classify the defect as repairable or non-repairable.

Step 3: Capture an image of the defect from the repair unit.

Step 4: Magnify the symbolic primitives and the defect rectangle to match the repair unit image.

Step 5: Align the symbolic primitives to those of the repair unit image.

Step 6: Detect the defects that fall in the defect rectangle in the repair unit image.

Step 7: Generate a repair bitmap from the detected defect(s).

Step 8: Repair by removing metal or laying down material.

Step 9: Capture another image from the repair unit and determine whether the defect is repaired, not repaired, or damage to the area has occurred; if feasible, repeat the repair attempt (steps 7-8).

Figure 28A:
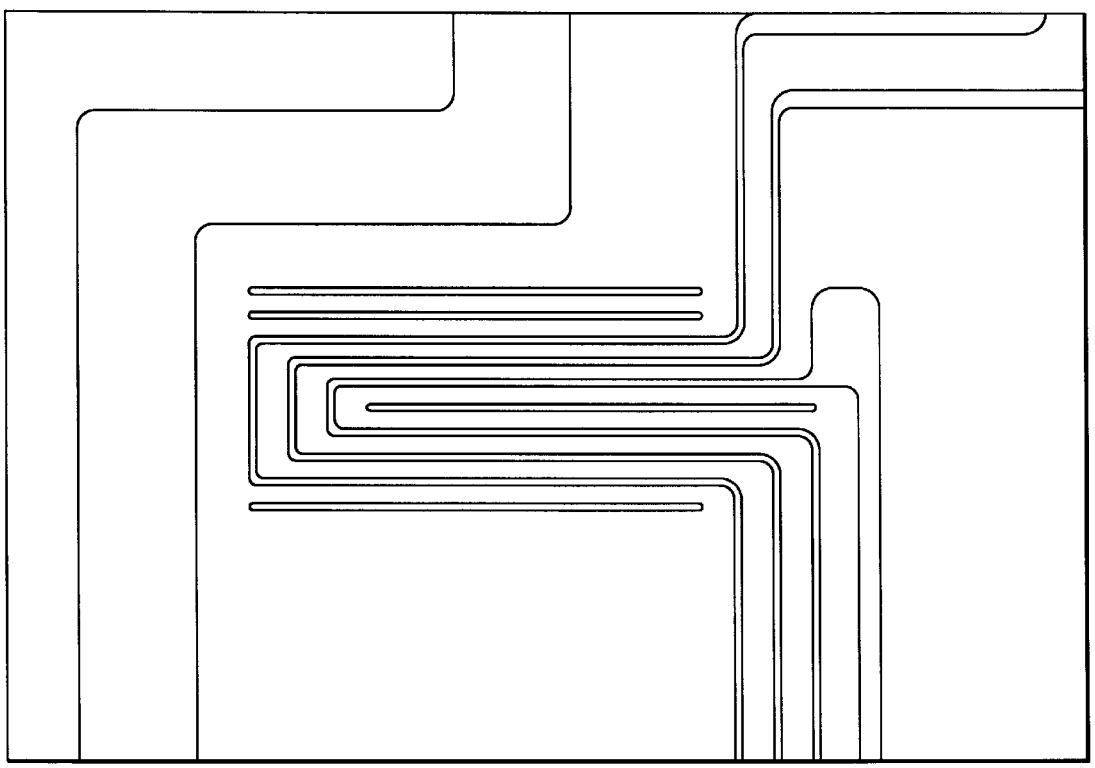
FIG. 28a illustrates a reference image.
Figure 28B:
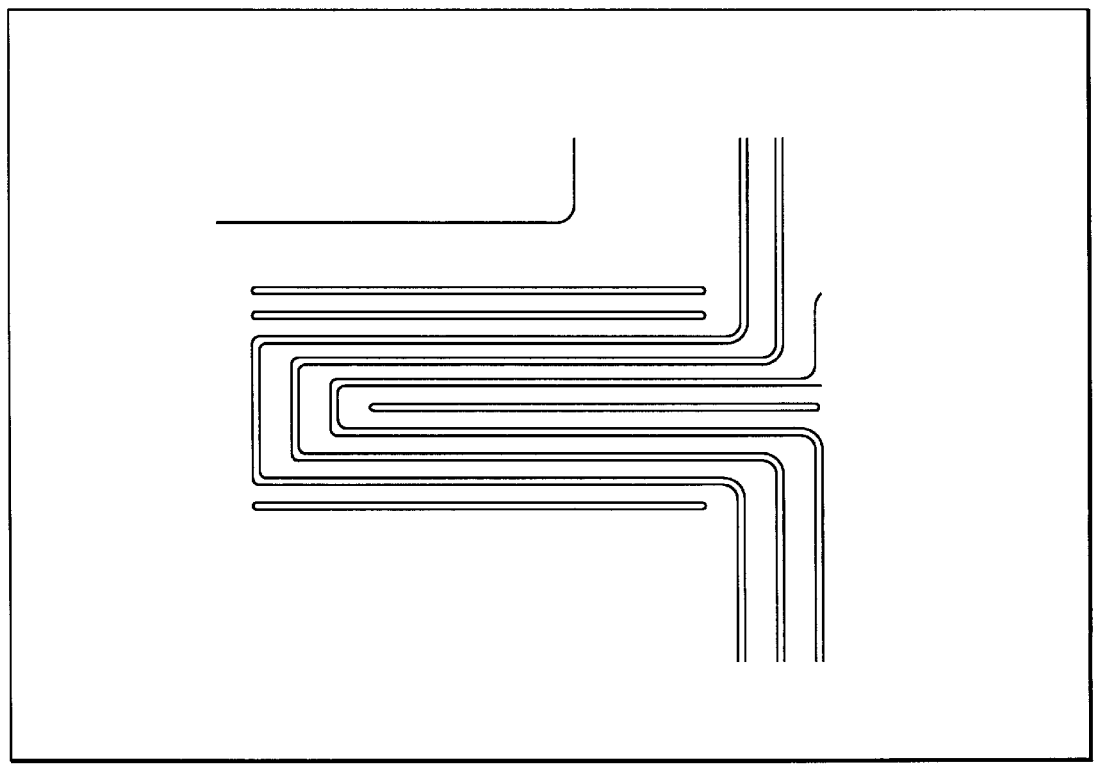
FIG. 28b illustrates the symbolic representation of the reference image.

In step 1 the optical defect image is aligned to an optical reference image. The symbolic representation of the reference image is generated as outlined previously by a command such as "symbolic_decompose( )". The symbolic representation of the reference image is aligned to the symbolic representation of the defect image. The command may be, for example, "align_all ( )", and the alignment may be accomplished using either the histogram method or major axis method or some other alignment method. For example, a reference image is illustrated in FIG. 28a. FIG. 28b illustrates a symbolic representation of the reference image stored in storage 462 of FIG. 27. The symbolic representation is the symbolic primitives as discussed previously. See also application Ser. No. 08/186,750, filed Jan. 21, 1994 of Hennessey, et al., entitled "Apparatus and Method for Image/Processing in Symbolic Space" which describes generation of symbolic primitives and application Ser. No. 08/347,020, filed Nov. 30, 1994, which are incorporated herein by reference for all purposes.

Figure 29A:
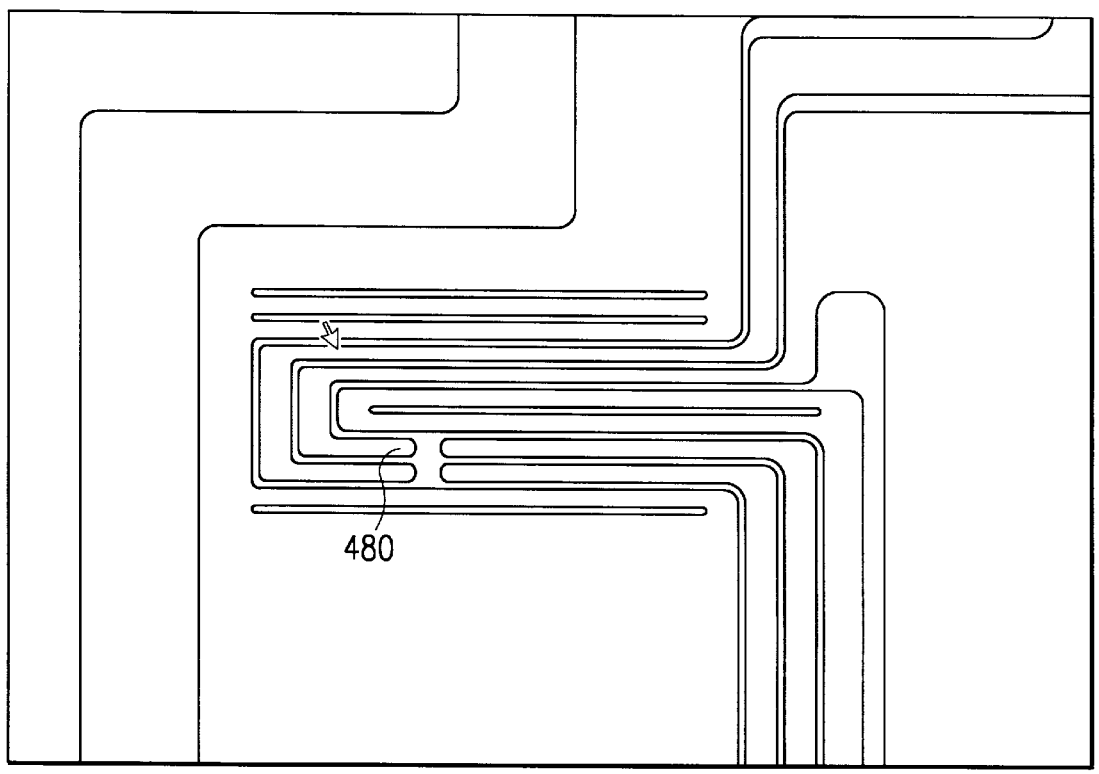
Figure 29B:
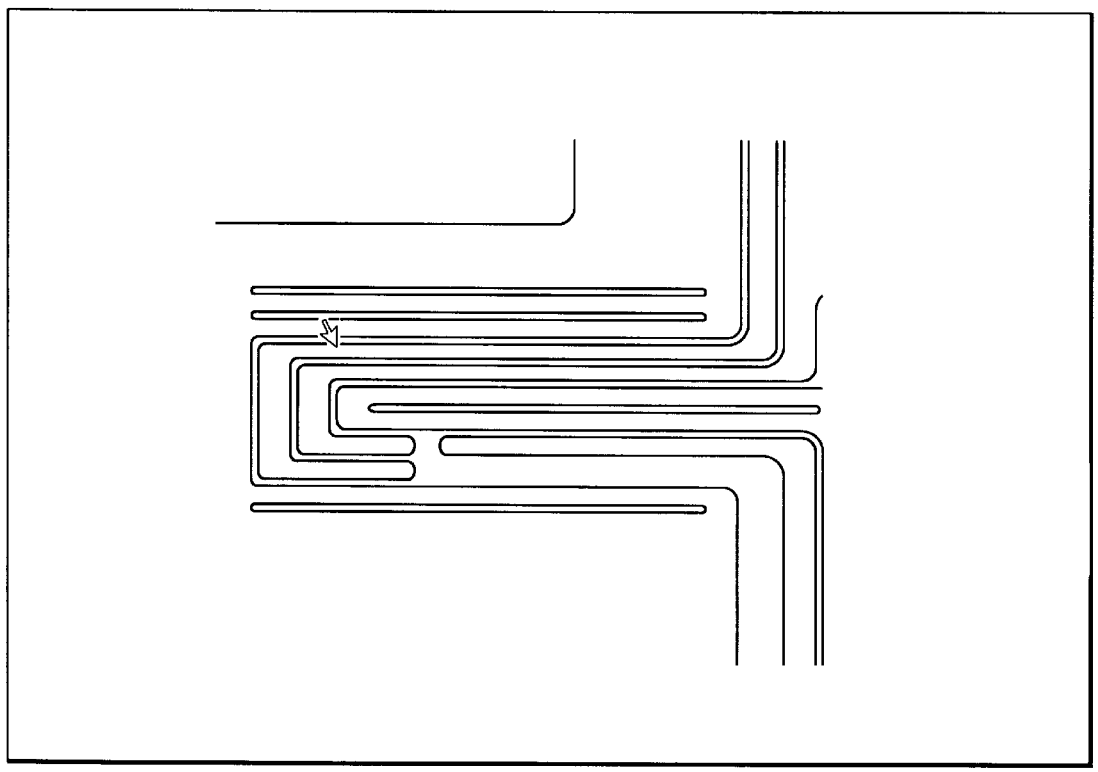

The defect 480, as found by a defect detection system (460 of FIG. 27), is illustrated in FIG. 29a. FIG. 29b is the symbolic representation of FIG. 29a. The image of FIG. 28a is fine aligned to the defect image of FIG. 29a using the symbolic representation of the images defined by FIG. 28b and 29b and the previously disclosed alignment method. The alignment processes described earlier can be used.

Figure 30B:
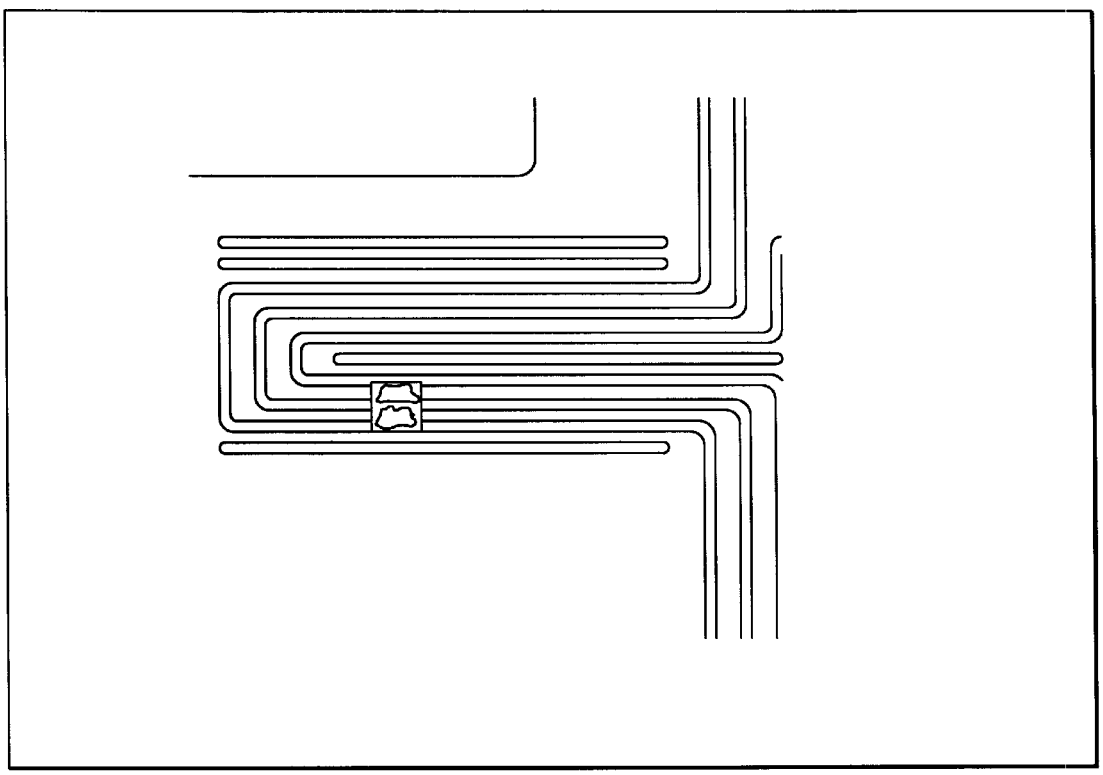

In step 2 the image of the defect is obtained by using image subtraction. The defect is outlined by subtracting the optical image from the reference image. The command to perform this step is, for example, "defects_from_subtraction ( )", which is illustrated in FIG. 30a where the reference image 500 and defect image 501 are subtracted leaving the defect image only 503. If there is excess metal in the defect image, a code 0 is generated indicating excess metal (a short), necessitating a burnout for repair. If there is metal missing, then a code 254 is generated indicating an open, which will be repaired by laying down more metal. The next step is to outline the defect with the rolling ball technique or some other decomposition technique such as that outlined in the anomaly location section or a reference incorporated herein. The coordinates of the defect shape is then stored. The command to do this is, for example, "locate_defect ( )". FIG. 30b illustrates the outlining of the defect. The x and y coordinates are taken at the center of the defect. This is stored and sent to the repair station (FIG. 468 of FIG. 27) to do the repair. In FIG. 30a, the defect image is isolated 505 and decomposed into primitives 506.

In step 3, an image of the defect is captured by the repair unit using the coordinates generated.

Figure 31:
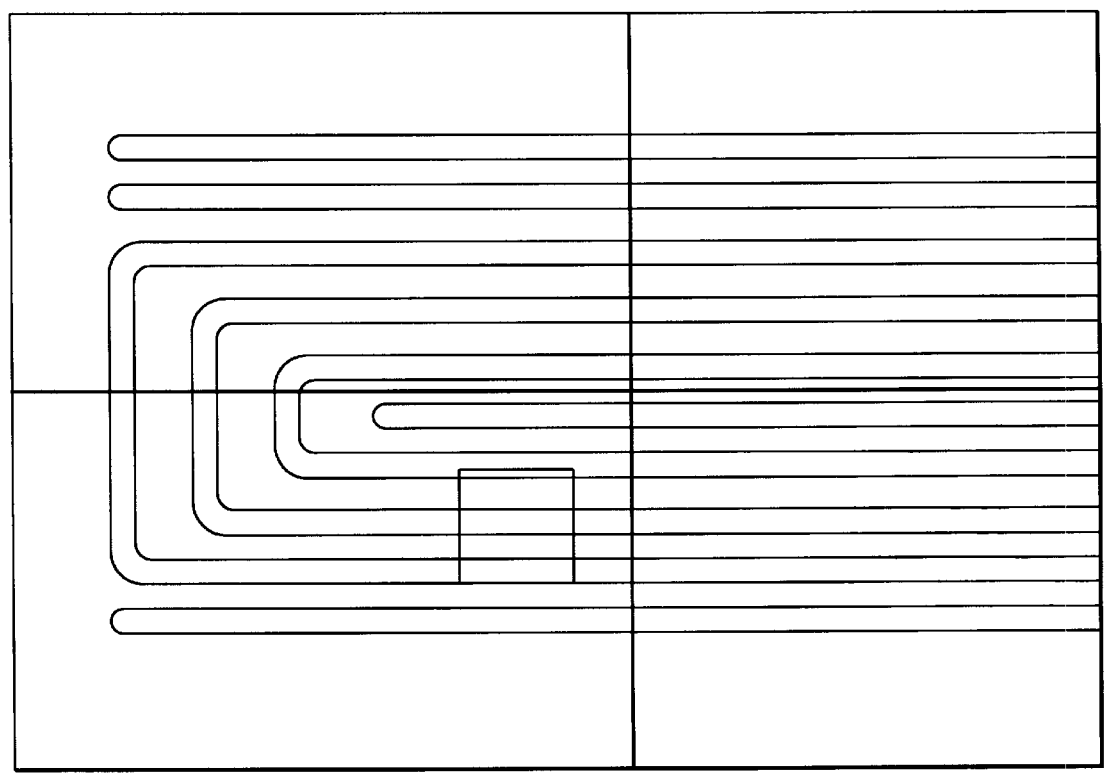
FIG. 31 illustrates defect area magnified in symbolic representation.
Figure 32:
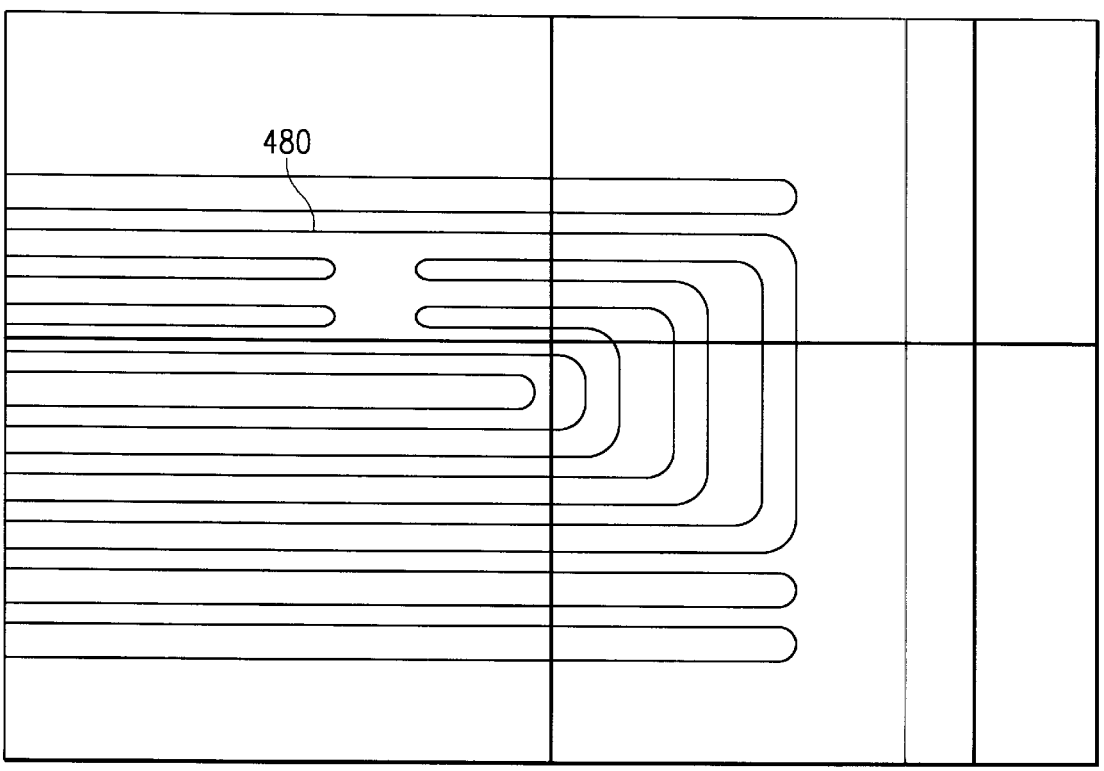
FIG. 32 illustrates defect area from repair tool image.

In step 4 the symbolic representation of the image in the defect rectangle is magnified to match the magnification level of the repair unit image from which a symbolic representation is also rendered. This is shown in FIG. 31. To do this, the system calculates the magnification factor for the optical image to match the repair beam image. The optical image symbolic information and the defect rectangle are magnified using the magnification factor determined. FIG. 32 illustrates the image of a defect 480 area obtained from the repair tool. A symbolic representation of this image is then used to match the magnification level of the symbolic representation of the optical image.

In step 5 the symbolic representation of the image is aligned to the repair unit image.

Figure 33:
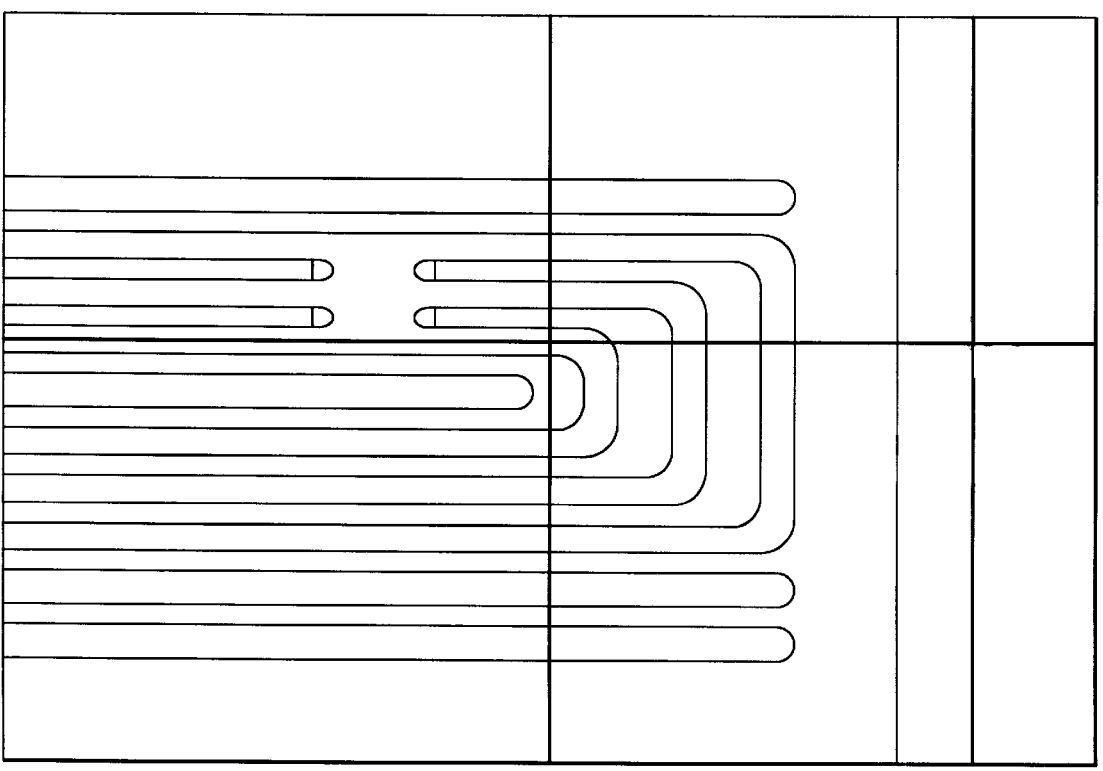
FIG. 33 illustrates alignment of enlarged symbolic representation with repair tool image.
Figure 34A:
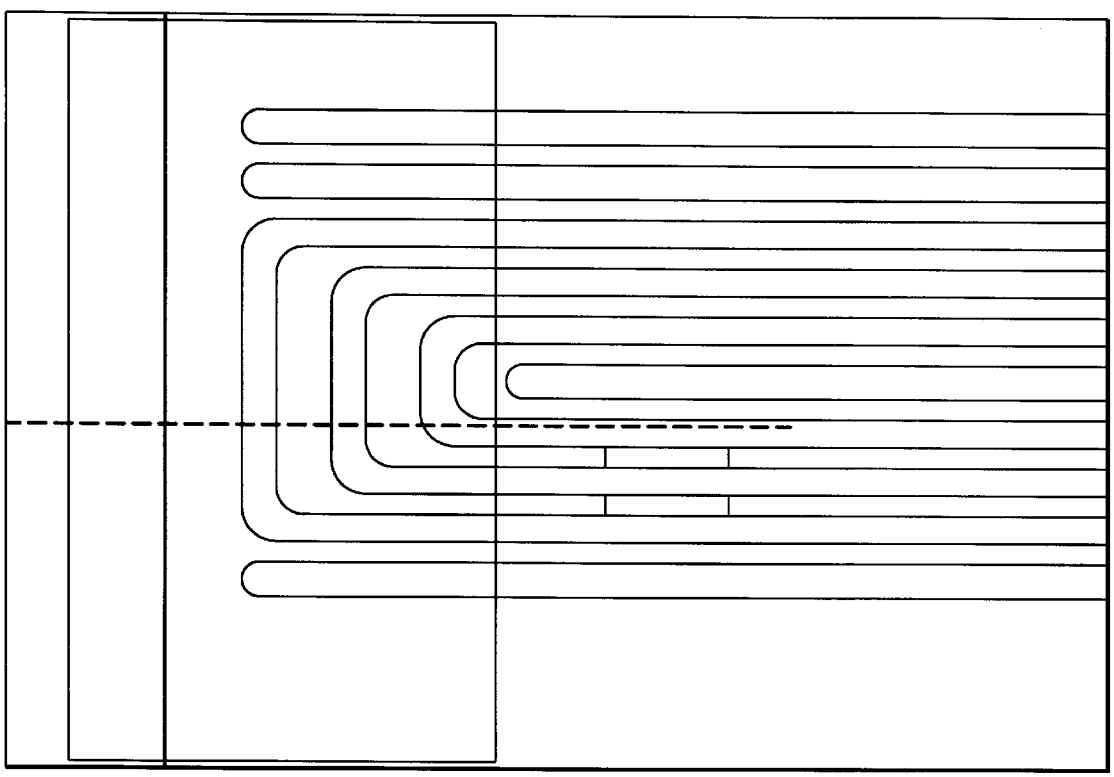
FIG. 34a illustrates the delineation of repair area in repair tool image and FIG. 34b illustrates enhances symbolic representation of repair (extended to a set of straight lines)

The zoomed symbolic information is aligned to the repair beam image by using the symbolic representation of the symbolic representation of the defect from the repair tool and optical image as illustrated in FIG. 33. This command is, for example, "align_all ( ), align_around ( )". An outline of the repair area is made. FIG. 34a illustrates delineation of repair area in repair tool image. In FIG. 30a, the symbolic representation of the defect from the repair tool 507a is aligned with the symbolic representation of the optical image 507b.

Figure 34B:
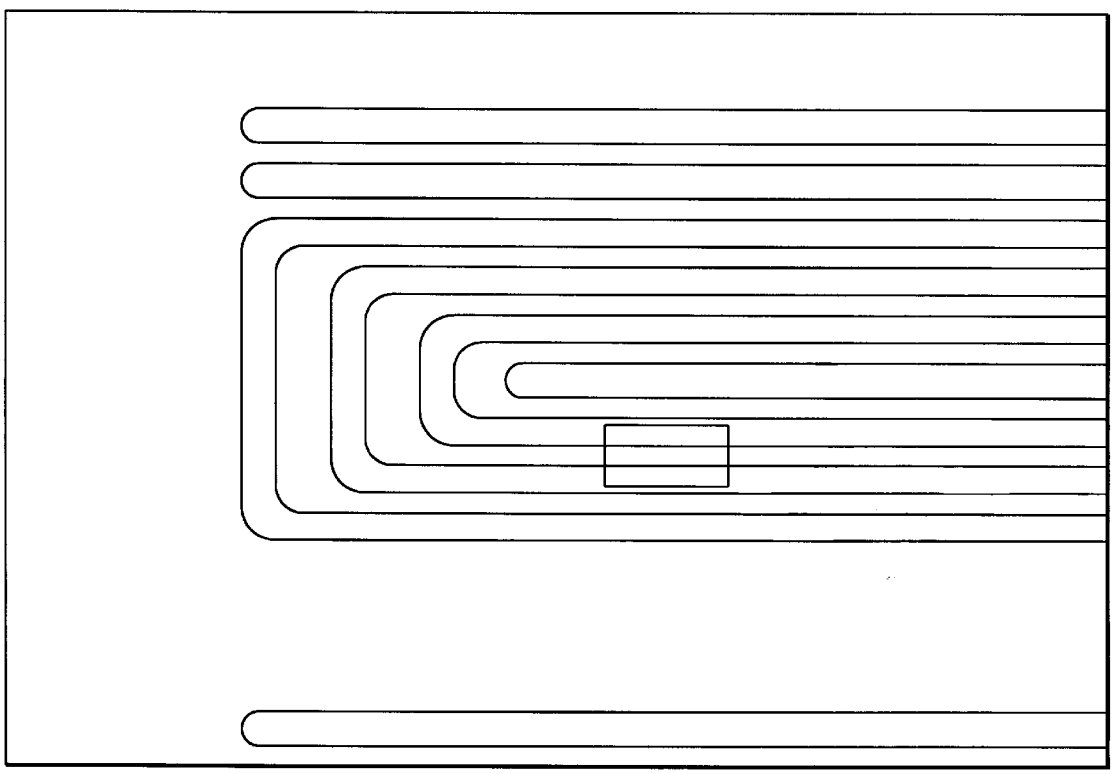

In step 6 the defects that fall in the defect rectangle of the repair unit image are detected. The symbolic information within the defect rectangle is extended into a set of straight lines that form the edges in the repair unit image (FIG. 34b). The command is "get_lines_from_seg ( )." The lines are aligned to the repair unit image for better accuracy.

The command is "align_seg_line ( )". Two lines at a time are taken and checked to determine if the area between the lines has any defect. This step is carried out by taking a small window between the lines. See FIG. 34b. The windows with defect are marked and all the adjacent defect windows are joined. The command is "catch_defect ( )."

In step 7, the system generates a repair bit map from the defect window and passes it along with the repair code (0 for excess metal or 254 for missing metal) and the repair coordinates to the repair tool.

Step 8 produces the repair by removing metal or laying down material depending on whether a 0 (excess metal) or a 254 (metal missing) code has been received.

Figure 35A:
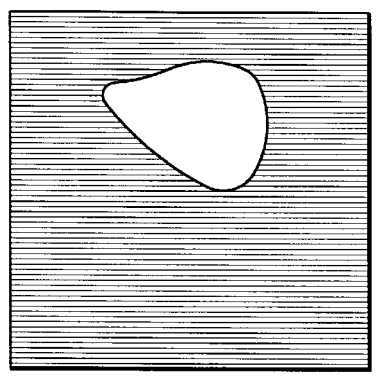
FIG. 35a illustrates a defect.
Figure 35B:
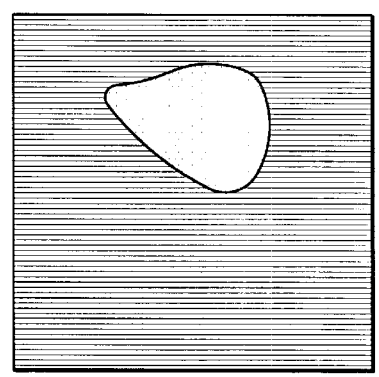
FIG. 35b illustrates the symbolic decomposition of the defect.
Figure 35C:
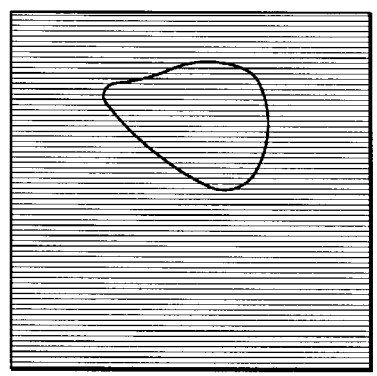
FIG. 35c illustrates a repair bitmap of the image.
Figure 35D:
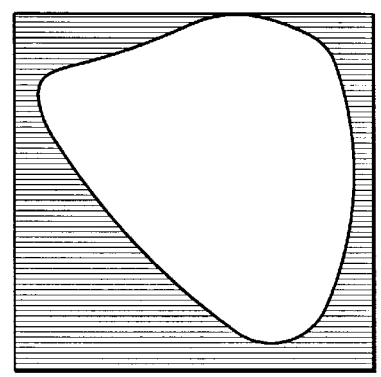
FIG. 35d illustrates a repair too large to fix.

In step 9, an image of the repair is obtained and the repair is obtained and analyzed to determine whether the repair was successful, unsuccessful, or caused damage to the surrounding area. If the repair was unsuccessful, the system analyzes the repair image to determine whether to repeat the repair attempt (steps 7-8). FIG. 35a illustrates a defect 381 on a wafer. FIG. 35b illustrates the defect 381 detected and outlined symbolically. FIG. 35c illustrates the repair bitmap and FIG. 35d illustrated a defect that is potentially unrepairable due to its large size.

According to another aspect of the invention, a camera is mounted on a manufacturing device and images or parts of the device and objects emerging therefrom are captured at regular intervals. Each image is treated as an image of a defect area. The system searches a knowledge base. Three sets, each having three or more examples per set, will have been selected by the operator and named "in tolerance," another set named "out of tolerance," and another "marginal tolerance." When the classifications "marginal tolerance" and "out of tolerance" reach a certainty level higher than a pre-set threshold, recently captured images are retrieved from the image base and the tolerance trend is calculated and displayed. Although the computer may automatically select and weight the most relevant attributes of the best examples for each set, or class of images, it can also display the performance of each example as a correct classifier so the operator can control and fine-tune performance of the system, as well as allowing the operator to add new examples or new sets with new names such as "extremely out of tolerance" or ">8% beyond tolerance." This embodiment can be used on a large number of industrial products and processes to monitor geometric tolerances and at the same time detect and classify intemittent defects such as cracks and malformations in product and manufacturing devices.

V. AUTOMATED YIELD MANAGEMENT

Enhanced yield management may be used as an aspect of the present invention. Yield management in the semiconductor industry involves collection, processing and storing vast amounts of information about defects, electrical test results and diagnoses as well as producing a variety of reports. Additional information from sources such as process logs, defects on previous layers of the wafer, the pattern of defects for an entire lot or production run, circuit designs, and device characteristics, are also used to make decisions about actions needed for continuous monitoring and improvement of semiconductor manufacturing processes, materials, procedures and designs.

An index of defect characteristics and other information for fast retrieval about subsets of defects and other relevant information can be derived from extraction of the yield management system's directory structure, because its subdirectory file names are created using, for example for the ADC system (defect classification system 2), defect features such as the device name, layer name, position of the defect, size of the defect, and defect class. Information retrieved by means of these indexes for all defect classes on a lot, e.g., lot L5074305, wafer 15, layer 16. Information may also be retrieved based on the number of defects for a process layer. This differs from other defect information retrieval methods in that the information can be retrieved in any order, in any subset without setting up a database query table.

The automated yield management system 5 manages not only defect class information but also indexes and manages images of defects, allowing review of information and images of defects by wafers, by layer, defect class, defect size, circuit design, electrical test results, etc. from the engineer's desktop without requiring direct examination of the wafer in the clean room, while at the same time providing displays from CAD files, electrical test files and defect classifications and diagnoses as well as analytical aids including correlation of electrical test data with defect data, and selection of defects within or outside a given range of values for descriptors as such as size, area, intensity per die and wafer. Yield management tools also include sorting and selection of sets of defects by a mixed set of criteria such as size, color and location, along with a yield history including failure rates for die from specific wafers.

VI. KNOWLEDGEBASE GENERATION, MANAGEMENT, AND OPTIMIZATION

As mentioned above, automated detemiination of the classification of a detected defect is done by mapping the descriptor values of the detected defect in feature space and finding the smallest Euclidean distance in feature space to the mapping of descriptor values of one or a group of classified defect examples (or knowledgebase rules).

Figure 36:
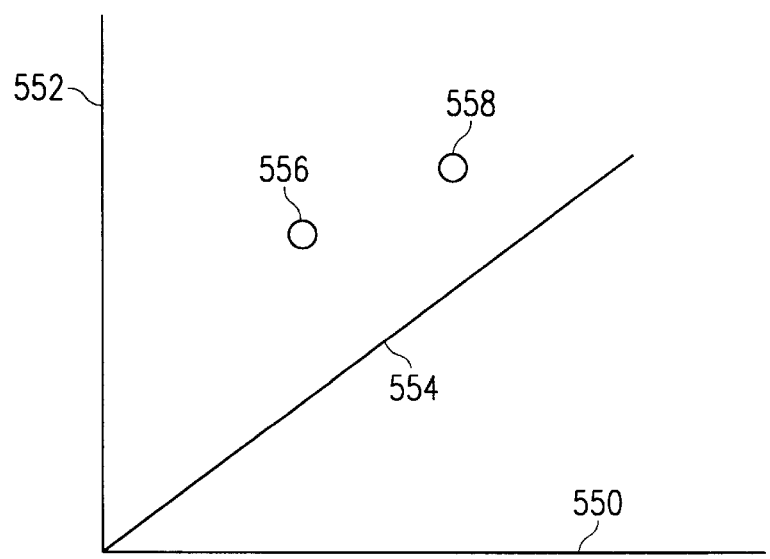
FIG. 36 illustrates a map in feature space of two defects using three descriptors.

Each rule can be represented as a position in a multiple-dimension graph, as suggested in FIG. 36. FIG. 36 illustrates an example where three descriptors are used, i.e., three dimensional. Each descriptor has an axis. For example, 550 is the axis (x-axis) for descriptor 1, 552 is the axis (y-axis) for descriptor 2, and 554 is the axis (z-axis) for descriptor 3. Defect 1 is shown by reference numeral 556, and defect 2 is shown by reference numeral 558. FIG. 37 is a three dimensional graph made up of two defects defined by the same three descriptors. The descriptors may be size, color, and eccentricity or any other group of three descriptors. The approach is analogous for n-th dimension descriptors. The dots represent the point of intersection of the values of the descriptors generated for example defect 1 (556) and example defect 2 (558) respectively. Therefore, in accordance with FIG. 37, if for example the values of descriptors 1, 2, and 3 of a redetected defect image intersect at or near the point of intersection of the descriptor values for example defect 1 556, then the redetected defect can be classified as defect class 1 or is associated with defect diagnosis 1. Similarly if the point of intersection is closest to that of example defect 2 558 then the redetected defect can be categorized as belonging to a defect class 2. The system can select five descriptors whose ranges of values are most unique for each class of defect. The automatic separation of defect example records into classes of defects—referred to as "unsupervised learning"—can also be achieved by this method so that an operator is presented with several images of an automatically selected defect class for naming only if desired, otherwise defects are grouped by arbitrarily assigned class numbers.

Figure 37A:
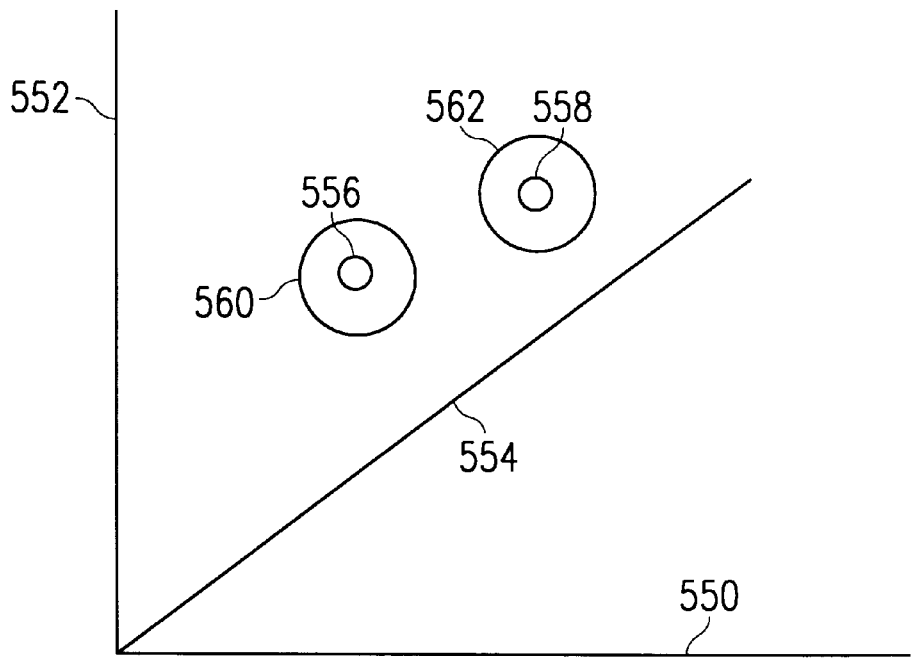
FIG. 37a illustrates a map in feature space of two defects with weights illustrated as a spherical confidence level and FIG. 37b illustrates an observed defect mapped within the confidence level of defect type 1.

It is recognized that not all defects will fit exactly within the narrow dot of the defects listed, and therefore there would be a confidence level which would represented by the circle around the dot as shown in FIG. 37*a*. Because this is a three dimensional rendering, they represent a sphere and not a circle as shown. The default value for confidence level is typically 60%. In one embodiment, changing this confidence level can be done by changing parameters contained in the ".ini" or initialization file. As the size of the confidence level sphere increases, the confidence level coefficient decrease. This means more marginal defects can be classified, but confusion can be caused by overlapping confidence levels. This problem can be overcome by application of valued "weights" to the descriptors.

Figure 37B:
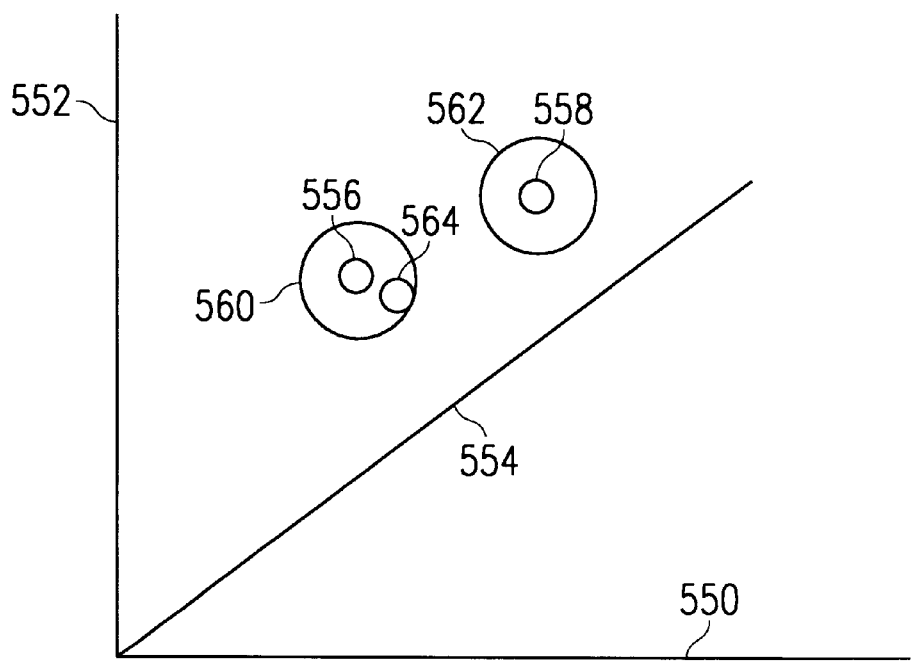

Weights are used when two or more classifications become confused with one another. For each defect attribute, there is an associated descriptor weight which indicates the significance of a particular descriptor to the classification of a type of defect. Initially the default weight for each attribute is set to 100. When default weights are applied to a rule, the confidence level that is used to determine whether an observed defect belongs to that type of defect can be represented by a sphere as shown in FIG. 37*a*. FIG. 37*b* illustrates an observed defect mapped within the confidence level of a defect 1 type 564. Weights can be set between zero and 1,000. A new set of weights can be stored, for example, in the ".ini" configuration file as shown below.

| [Weights] | [Weights] |
|---|---|
| Index_val = 01 100 | Index_val = 01 200 |
| [Weights] | [Weights] |
| Index_val = 02 100 | Index_val = 02 500 |
| .... | .... |
| [Weights] | [Weights] |
| Index_val = 029 100 | Index_val = 29 0 |
| a. Default weights | b. Adjusted weights |

Figure 38A:
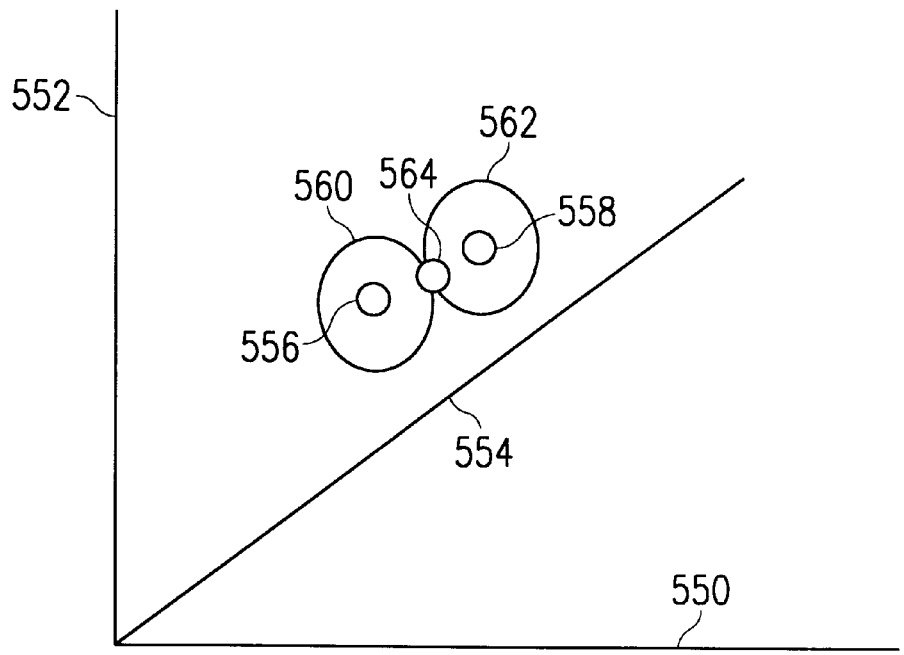
FIG. 38a illustrates defect classes whose descriptors' confidence levels overlap and FIG. 38b illustrates a method of differentiation between defect classes using varied weights.
Figure 38B:
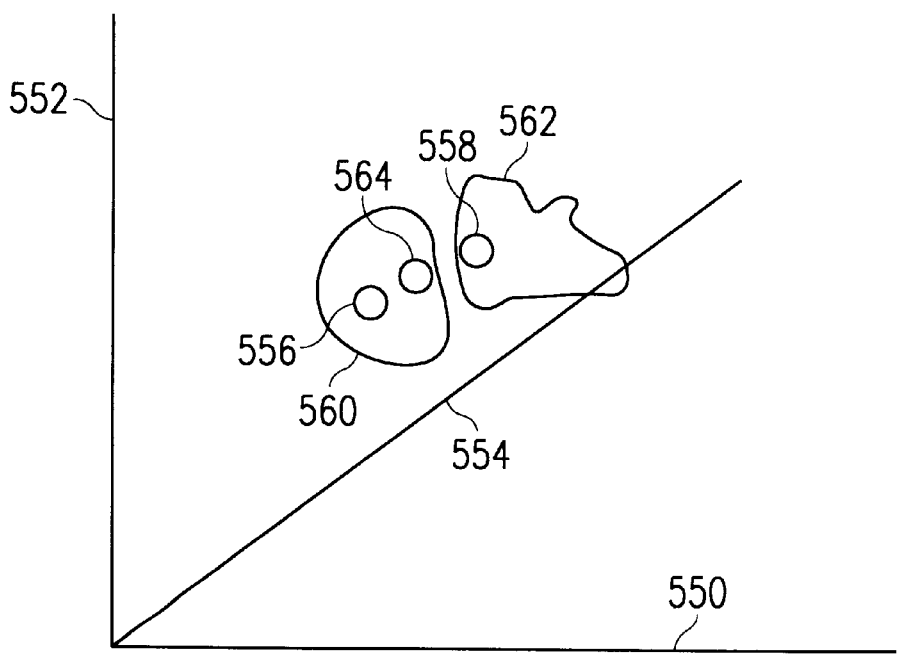

As shown in FIG. 38*b*, the effect of altered weights is to produce an irregularly shaped area which allows the system to differentiate the example defects of one class from those of another class. For example, in FIG. 38*a* the intersection of the descriptor values derived from an image of a defect is represented by a large solid dot 564 that is on the overlapping area between the intersection of the descriptor values 550 and 562 of the image defect type 1 (556) and that of the defect type 2 (558). By defining these classes in irregular three dimensional shapes produced by application of varied weights, as represented in FIG. 38*b*, clear distinctions can be made between what might appear to be overlapping classes when the same descriptors are evenly weighted.

When the values of image descriptors of different defect classes are very similar, classification accuracy problems can occur. In order to resolve confusion between two defect classes, "a secondary validation table" can be used. The secondary validation table contains entries for two similar classes and a list of those attributes that can be used to distinguish between them, derived from analysis and comparison of the descriptor values for each example of the similar classes that are stored in the knowledgebase. The details of how to identify confusing classes and how to identify discriminating descriptors is provided by the knowledgebase analyzer 48 (FIG. 2) as described below.

For each defect, the ADC system performs the three steps: a) defect detection, precise location and delineation; b) descriptor generation, and c) either learn a rule or classification. In this system according to an aspect of the present invention, it can also store and index an image of the defect for future reference. The system loads the image, locates its defect, selects a name of the defect with matching features, and provides and calculates the degree of certainty. For example, a pattern type defect detaches with a 98 degree of certainty would be called Patt 98. Therefore, the name Metal_1_Extra_Patt might be chosen in the case where the defect is caused by extra metal deposited on the wafer causing a pattern type error. Also recorded would be the degree of certainty of the match, in this case 98 percent.

The steps in the classification process can be summarized as follows: a) convert the defect image into a set of high level descriptors (descriptor generation); b) compare the defect images descriptors with those found in each rule in the knowledgebase; c) identify the rule which is most similar to the observed set of values of defect image descriptors; d) determine if the similarity value is above the confidence level threshold; and e) select the identifier of the most similar rule. In accordance with the teachings herein, a mini-knowledgebase for each device and each layer may be created to achieve a better accuracy by narrowing and focusing the scope of the system's classification effort.

Figure 39:
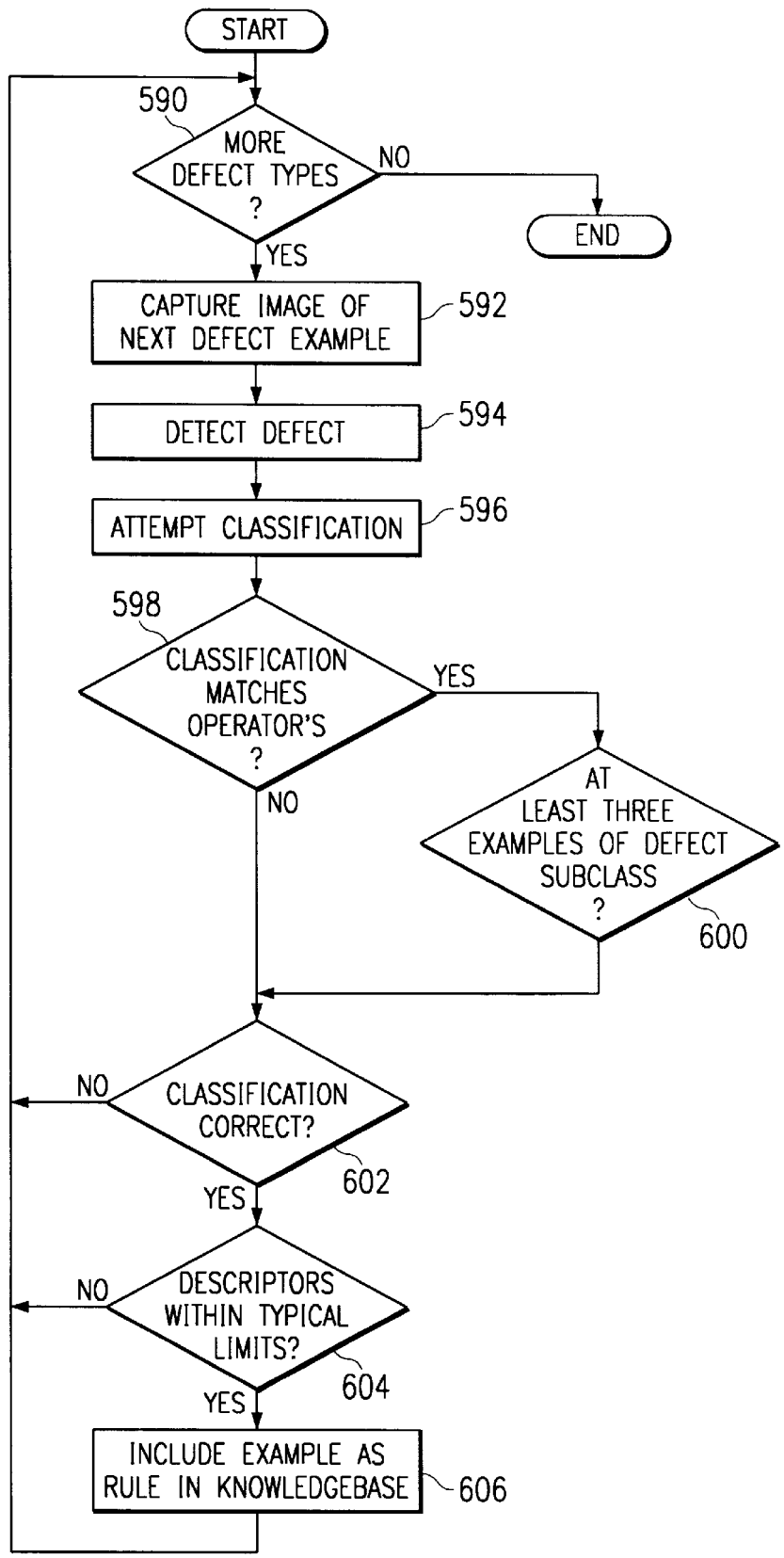
FIG. 39 is a flowchart of defect knowledgebase construction.
Figure 40:
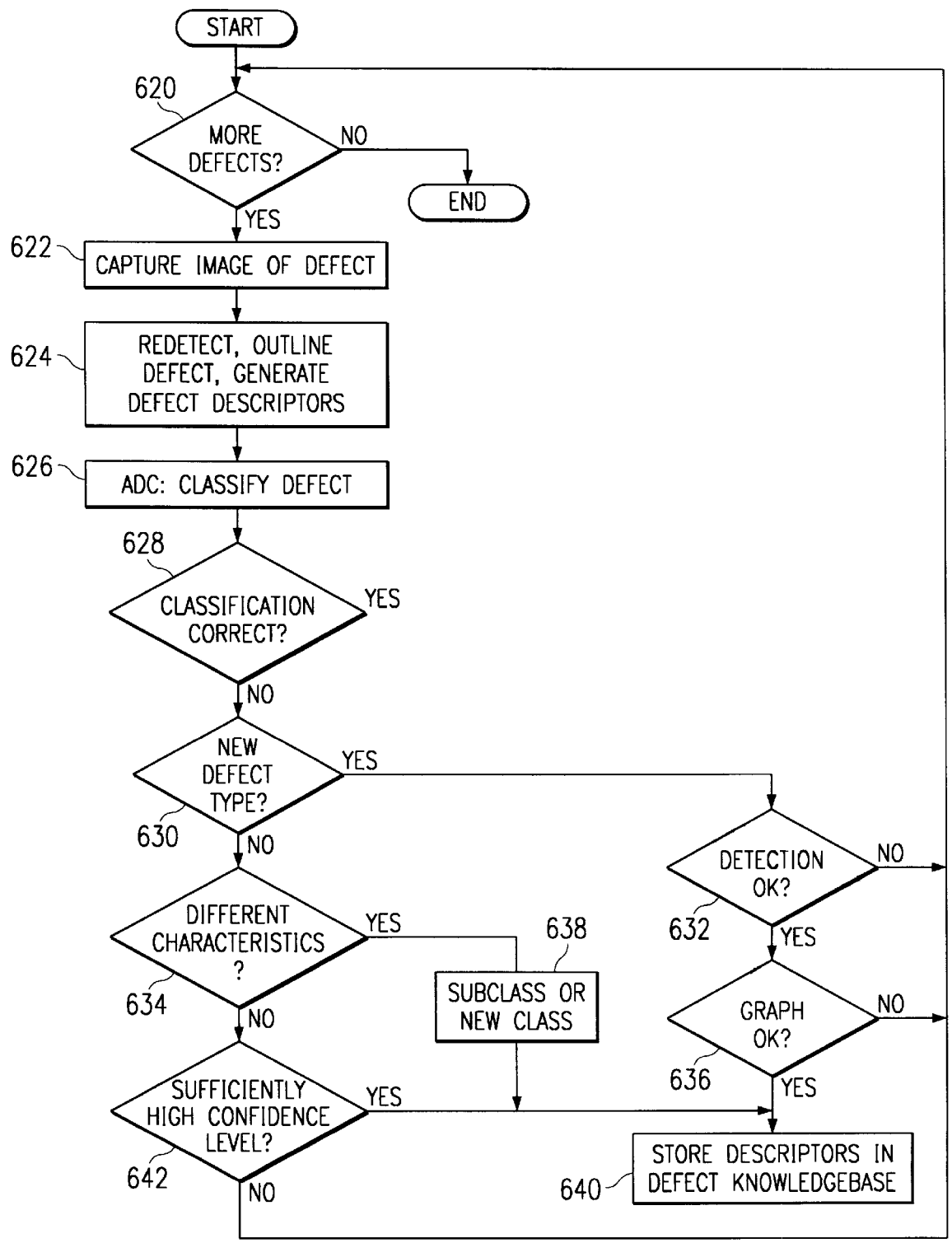
FIG. 40 is a flowchart of knowledgebase editing.

An initial defect knowledgebase with rules that describe general types of typical defects such as "particle" can be provided to avoid the need for experts to create these rules for each mini-knowledgebase. The flow chart of FIG. 39 gives the details of the steps involved. Referring to FIG. 39, the system determines if there are more defect types to be added or stored in the defect knowledgebase 50 (FIG. 2) at step 590. If so the system captures the image (step 592) of the next defect sample and then redetects the defect (594) using one of the methods referenced above. In this case, for example, the first method is tried and tested against the degree of certainty. If below a threshold value, the second method is tried. This then continues to the third method and other methods until a set threshold degree of certainty is met. The defect is then classified in step 596. The system asks the operator if the classification is correct (step 598); if correct and if at least three examples are taken (step 600), no more examples need to be added at the initial set up. If three have not been taken, the system asks if the classification is correct (step 602); if so and if a typical one, the system records the set of defect descriptors along with the classification as a rule in the defect knowledgebase 50 (step 606). Also, if a defect has been correctly detected and outlined but wrongly classified, that defect—with the corrected classification— may be entered into the knowledgebase if it is a typical defect of that class.

Correct classification of defects by the ADC system is dependent on the contents of the defect knowledgebase 50, which represents an expert's knowledge about defects. Not all experts consistently classify defects. When a defect is correctly detected, but the classification is wrong, the knowledgebase should be amended to provide a better set of examples. When a new type of defect is encountered, sufficient examples (usually three) are added to the knowledgebase. Several defect knowledgebases 50 can be constructed and maintained for the same set of production wafers in order to accommodate different inspection objectives that require different sets of defect classifications for the same defects. The easily accessible and flexible architecture of the defect knowledgebase 50 allows for quick changes, fine tuning, regular maintenance, and optimization of the performance of the defect knowledgebase 50 that are desirable under production conditions due to changes in wafer processes, the need to provide more specific or more general classifications, changes in defect characteristics and frequency, and the emergence of new defects. This maintenance can be carried out by an operator or automatically using the knowledgebase analyzer 48 (FIG. 2).

Knowledgebase Analyzer. The performance of the defect knowledgebase 50 can be improved by (i) editing its contents (adding, deleting or modifying rules); (ii) setting new weights for descriptors; and (iii) providing mean and standard deviations for each descriptor within a class. These sources of improvement are discussed in more detail below.

Editing the Knowledgebase. The defect knowledgebase 50 automatically created by the ADC system is a text file which can be edited using any standard text editor. As shown in the flowchart in FIG. 40, rules which reflect a particular type of defect well and are usually used correctly in the classification process are retained in the knowledgebase, while rules that are frequenly associated with misclassification are deleted. The defect classification computer 46 (FIG. 2), after capturing an image of a defect (FIG. 40, step 622), redetecting and classifying it (steps 624, 626), determines whether the classification is correct (step 626). If the classification is incorrect, the defect classification computer 46 determines if it is a new defect type (step 630). If so and if detection was successful (step 632), it then checks the defect class descriptors graph (e.g., FIG. 42) to determine whether its descriptor values correspond sufficiently to the parameter set derived from the example defect images selected by an expert for the same class (step 636), and if so the defect record including the descriptor values are stored with its classification in the defect knowledge-base 50 (step 640). If the defect is not a new type, the defect classification computer 46 determine whether the set of descriptor values of the new example defect are markedly different from those for that classification and other sets of descriptor values in the database (step 634), when the confidence level is high (step 317). Finally, the new rule is assigned to a subclass or new class (step 638) and stored in the database (step 640).

In higher debug modes, ADC can display the information regarding the rules by which the defect has been classified. This information includes the rule number, its defect class, and similarity to the observed defect for the most similar two rules. The displayed message may be as follows:

max_s=87 (cls 7 i=5)

sec_s=64 (cls 4 i=11)

This display message indicates that the defect class 7 has been selected with certainty level 87% using rule 5. It also shows that the second most similar class is 4, selected using rule 11 with a certainty level 64%. It is then possible to find the rule that is most frequently associated with misclassification and delete it. For example, if the rule causes other types of defects to be classified as class 7 most of the time, it should be deleted from the knowledgebase.

Changing default weights. The default descriptor weight is at 100. Descriptor weights can be changed whenever some descriptors are found to be better discriminators for proper classification of defects. Increasing the weights for certain attributes usually means that these attributes are better discriminants than others. Similarly, the descriptors that have less importance for defect classification can be set to smaller weights.

The rules kept in the knowledgebase do not have any weights. Descriptor weights can be stored separately in an initiation or ".ini" file. Alternatively, an operator could adjust weights "on the fly" at a work station. The descriptor weights are applied by ADC during execution of the program, and affect the certainty level of the classification. In this way, descriptor weights may be changed at any time without the necessity of modifying the rules in the knowledgebase.

For example, if color is an important factor in classifying a type of defect, classification accuracy can be improved by increasing the relative importance of color attributes 22 and 23 from the default value of 100 to 300 in the configuration file.

Automated knowledgebase analysis. When a human operator is trained to classify defects, (s)he actually learns from examples of each defect class. But the operator does not use the example itself to classify a new defect; in fact, the operator extracts some information about each class using those examples. Even though it is not possible to know how many "descriptors" an inspector actually uses to classify a defect, current research indicates that the information representing each class in the human operator's mind is not specific points for each descriptor but rather ranges of those descriptors. For example, when all defects from a particular class are blue, the degree of blue is still relative from one defect to another and even from one person's vision to that of another. Therefore, if the color blue is the only descriptor used to identify a particular class, for example, "phosphate blue dot", it is more likely that a defect will be classified as "phosphate blue dot" when the value of its color descriptor falls within a certain blue range.

Figure 42A:
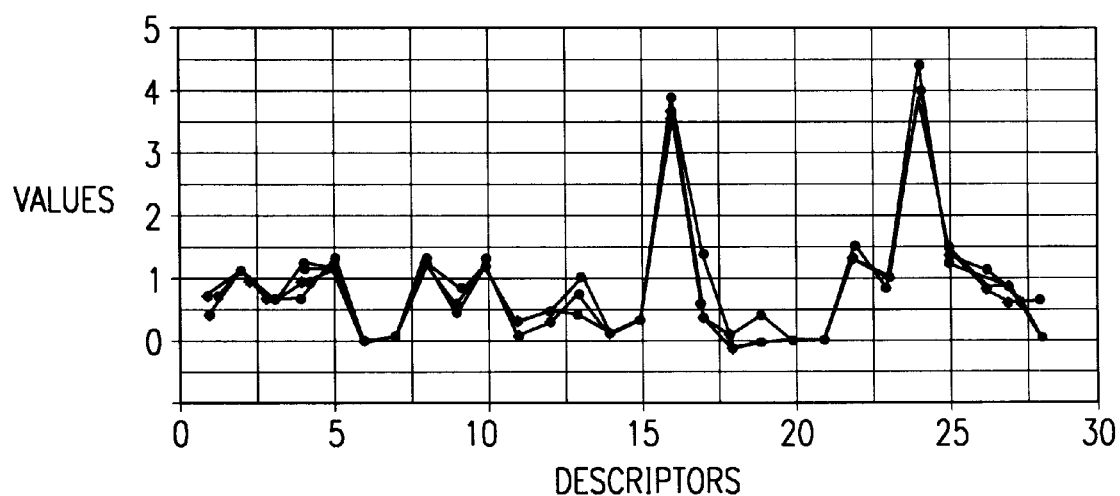
FIG. 42a illustrates a graph of defect knowledgebase examples of one class of defects whose images have been selected by an expert operator and FIG. 42b illustrates a graph of defect knowledgebase of a class of defects whose images have been selected by one unfamiliar with that class of defects.
Figure 42B:
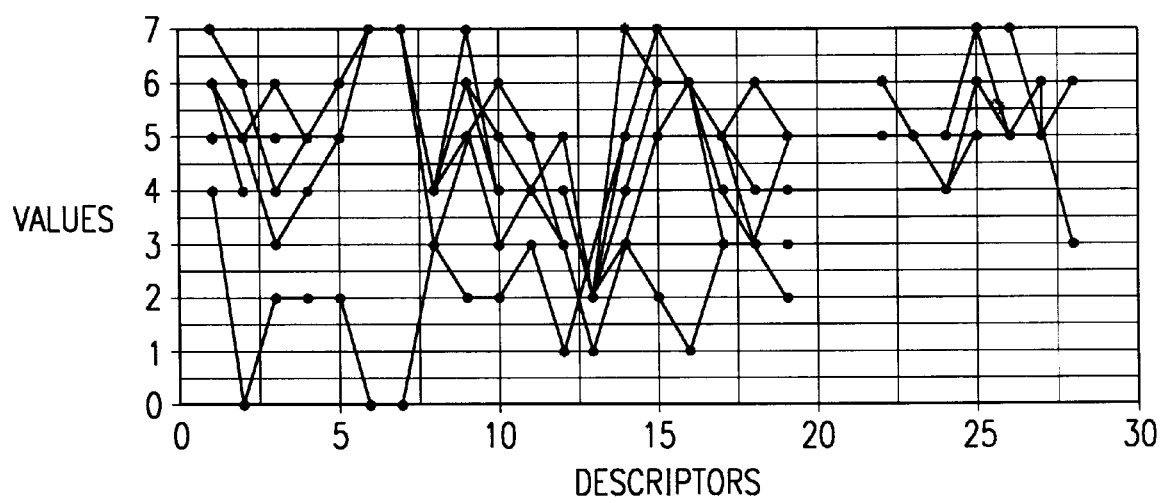

The ADC system is designed to simulate the performance of the human operator. Each rule in the knowledgebase contains examples from several defect classes. A defect class is represented by selected examples from that particular class. Because descriptor values for a class of defects may vary within a range depending on the characteristics of the defect, the system provides information about the range of descriptor values within a class. For each class, some sets of descriptor values may have a very narrow range while for some other sets of descriptor values the range will be much larger. Usually descriptors with narrow value ranges are better discriminants. Even though some descriptor values for one example may be the same as those for examples of another defect class, the ranges of descriptor values will usually differ from one defect class to another. For this reason, a composite view of the defect's visual characteristics can be employed to verify the result. As shown in FIG. 42, the descriptor values of defect images selected by an expert as good examples of defect class 48 are very close to one another, while those selected by a novice as examples of the same class diverge so widely that none of the descriptors is an adequate discriminant. This allows the operator to determine, from a graphical representation of the descriptor values of the examples of a class of defect, whether the set of descriptor records of the defect images selected for that class contain sufficient knowledge for the system to be able to produce correct classifications.

The contribution of each descriptor to the similarity between a defect and a given knowledgebase rule is a function of the Euclidean distance between the defect's individual descriptors and means of the descriptor values within the rule's class. The statistical distance between the defect descriptor value and the overall mean of that descriptor may be found according to the following:

$$D[i]=(O[i]-\mu[k][i])/\sigma[k][i]$$

where:

D[i]: Distance

O[i]: Value of defect's descriptor i $\mu[k][i]$: Mean value of descriptor i for class k $\sigma[k][i]$: Standard deviation of descriptor I for class k.

The relationship between the contribution to certainty and statistical distance is not linear.

The similarity of a defect to a given rule can be defined as;

$$\text{Adjusted\_Similarity}[i][j]=S(O_i, R_j)+\Sigma \acute{A} D_{ij}[k]$$

where

"i" represents the observed defect,

"j" represents a rule from a knowledgebase,

"k" is an index for descriptors,

"O" is the set of descriptors for observed defect,

"R" is the set of descriptors for a rule from the knowledgebase,

"$S(O_i, R_j)$" is the similarity function,

"$D_{ij}[k]$" is the statistical distance between the mean of descriptor k for class j and the defect i's respective descriptor value, and $\acute{A}$ is;

$$0.05*\sigma \text{ if } \sigma \geq 2$$

$$0.02*\sigma \text{ if } 1 \leq \sigma < 2$$

$$0.01*(1-\sigma) \text{ if } 0 \leq \sigma < 1$$

A file containing the mean and standard deviation for each descriptor within a class may be calculated and stored in an ASCII file; its existence triggers the defect classification computer 46 to use its descriptor value range information to classify defects.

Because any data set used to produce means and standard deviations is a subset of all possible defects, any actual defect descriptor value is not likely to be exactly the same as the mean for that descriptor in a knowledgebase rule; for those descriptors with a zero (0) standard deviation, a minimum vanance of 0.01 is used. It is not necessary for the system to use means and standard deviations of descriptors for every class in the knowledgebase; when there is no entry for a certain class for which a rule exists in the knowledgebase, the defect classification computer 46 derives a similarity coefficient solely from the Euclidean distance of defect image descriptor values in n-dimensional feature space as described above.

Indexing and retrieving defect information and images. Because visual information about semiconductor defects is vast, multidimensional, and, in many cases, globally distnbuted, the method of storing and retrieving information and images about defects from the defect knowledge-base 50 and the defect image file 54 is a significant factor in providing rapid access and retrieval. To define fields, or attributes in a database, operating system subdirectories may be created, for example: c:\lot.__\wafer.__\layer.__\class.__\coordinates. Thus a file located in the subdirectory c:\1248\23\source__drain\nit__in\14.08 would contain details of defects for lot 1248, wafer 23, the source drain layer, defect class "nit-in", at position x=+14:y=+8; that is in the 14th to the right, 8th up from the center. From only this information, without retrieving a single defect record, it is possible to produce the defect histograms and wafer maps that are used for analysis by semiconductor manufacturers. Because this information available in the subdirectory names, it can be rapidly accessed by use of operating system commands to produce a list of relevant index information for any of these levels. New indexes, local indexes, and special purpose indexes can easily be created and, because they are very compact, can be transmitted quickly, shared, and merged with other indexes and information—such as compressed defect images—quickly throughout a global enterprise network.

Figure 41A:
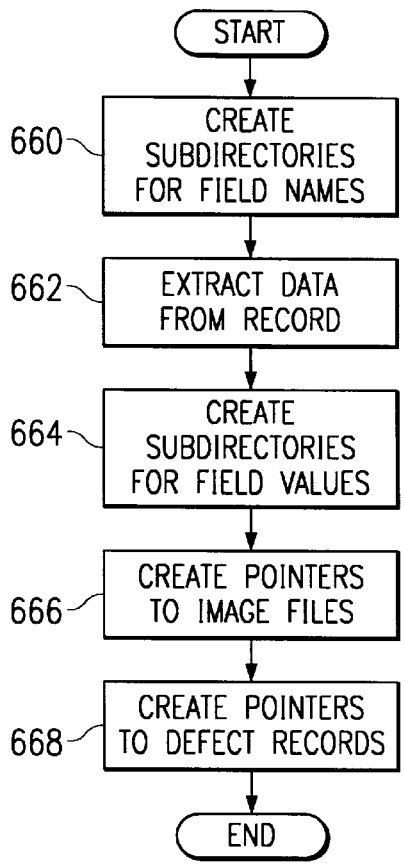
FIG. 41a is a flow chart of the creation of subdirectories for index.

Following the flowchart in FIG. 41, an embodiment of the invention can be implemented as follows:

To store data as shown in FIG. 41a, first create files with a $ extension containing the field names for subdirectories (step 660):

Field names for the stem record in "defects.$":
1:lot_no
2:wafer_no
3:layer_no
4:det_no
5:die_xy
6:mpos_xy
7:class
8:cap_date Field names for segment records ($1=first segment, $2=second segment, etc.):

"defects.$1"
1:def_id
2:def_size
3:def_coir
4:edg_shrp
5:txtr_var
6:edg_smth
7: . . .

"defects.$2"
1:def_id
2: . . . additional descriptor fields

Separating the defect record into segments keeps the directory contents below the maximum limit for file names, and allows searches on specific descriptors without having to load and examine entire defect records.

Next, extract data from the record (step 662):
File name: 144362 (Lot No.).07(Wafer No.)—this number is laser scribed on the wafer Record contents: mtl2-44 (Layer), 121 (detected anomaly number), +16 −5 (die number), 84.108 (xy position on die), 4 (Defect class), 48 (Defect Size), 11 (Color), 137 (Edge sharpness), 54 (Texture variety), 81 (Edge Smoothness)

And create subdirectories for field values (step 664):
Directly copy stem record fields:
md\144362\07\mtl2-44\43\16.−05†84.108\4\19960406

Store in data directory dictionary files for data strings or values represented by a code:
"\144362\07\layer.dioly . . .
2: mtl1 . . .
. . .
6:mtl2-44
. . .

(Names of reworked layers are preceded by a $)
"\144362\07\06\defclass.dic"
1: particle large metal
2: particle med metal
3: particle small metal
4: scratch
5: metal missing
6: . . .

Encode defect identifier: lot, wafer no., layer no., detected anomaly no., using directory character set (This is done both to save space as well as for security reasons). The code divides all the subdirectory information into two digit groupings and replaces these numbers with equivalent characters that can be used as a subdirectory name in a particular operating system. For example: 0–9,A–Z,-!@#$%^&{}~-" can replace numbers 0–49 while numbers after 50 start over at 0 again with a _ in front of the character (i.e., 50 is _0). Therefore: \144362\07\06\121 is encoded thus:

14=E, 43=´, 62=50 shift(_) and 12, or _C, 07=7, 06=6, 12=C, 1=1 or \E^_C76.C1

Create encoded defect descriptor segment records with the following fields:

\def_id\def_size\def_colr\edg_shrp\txtr_var\edg_smth\ . . .

so that 48 (Defect Size), 11 (Color), 137 Edge sharpness), 54 (Texture variety), 81 (Edge Smoothness), . . .

is encoded as:

\E^_C76.C1\48\11\137\54\81\ . . .

Finally, create pointers to image files (step 666):
In the following defect subdirectory record:
\lot_no\wafer_no\layer-no\det_no\ . . . \
\144362\07\06\121\ . . . store a file "images" containing the names of the image files for that defect:
\144362\07\06\121\ . . . \E^_C76.C1.img
1: volume address of image file:
header, e.g. uuuu@aaaaa.bbbb.ccc (network) or c:(local drive)
or 1F2E379A225 (disk or cdrom volume number) main directory, e.g. \defects
2: imagefilename(s): E^_C76.C1G
(Last character is image type: 10X=A, . . . 150X= G, . . . SEM=S)

And create pointers to defect records (step 668):
The imagefilename itself can be decoded to give the lot number, wafer number, layer number, and defect number, e.g.:
E^_C76.C1G is decoded as Lot Number 144362, Wafer Number 07, Layer 06, Defect Number 121.

In the "comments" section of each image file, this information can be inserted:
"Lot No. 144362, Wafer No. 07, layer No. 06, Defect No. 121" along with the date the image was captured.

This produces the following linked-list data structure:
Defect stem record (field names are in file with extension *.$):
Lot no.
Wafer no.

Layer no.
Detected anomalies
Anomaly number
Die xy
Defect position xy, in microns
Defect class
Date classified
Pointer(s) to image file(s)
Defect segment records (1.n) (field names are in files with extensions *.$1, *.$2 etc.)
  Defect identifier (encoded from Lot no, Wafer no, Layer no.,
  Detected anomaly no.)
  Defect descriptor(s) (1.n in groups of 8), e.g.
  Descriptor (1) size
  Descriptor (2) color
  Descriptor (3) edge sharpness
  Descriptor (4) texture variation
  Descriptor (5) edge smoothness
  Descriptor (6) . . .
  Defect image files:
    (File name uses defect identifier from segment records)
    (Comments field contains Lot No., Wafer No., Layer No., Detected Anomaly No., date of capture)
    Bitmap of image To produce the index as shown in the flowchart of FIG. 41*b*, first create an ascii tree index and number the lines(steps 680 and 682):

tree c:\defects>treefile\a
  find "-" treefile>numffile which produces (to which the directory stub c:\defects is added):

Then produce a linked list and write it to an index file (steps 684 and 686) that is stored in the first directory (in this case c:\defects); it can be copied for used elsewhere on a network or onto any file medium:

The format of each line is: line number, pointer to previous line in linked list, field number, data:

| | | |
|---|---|---|
| [002]3A6A-1BE7 | | Volume identifier |
| [003][001]1:C:[D]EFECTS | | Directory address |
| [004][002]2:144362 | | Lot number |
| [005][004]3:07 | | Wafer number |
| [006][005]4:06 | | Layer number |
| [007][006]5:121 | | Detected anomaly number |
| [008][007]6:16.-05 | | Die xy position (from center of wafer) |
| [009][008]7:84.108 | | Xy position on die in microns |
| [010][009]8:4 | | Defect classification |
| [011][010]9:19960406 | | Date of classification |
| [012][005]4:05 (Pointer to Wafer No.07) | | Layer number, same lot and wafer |
| [013][012]5:43 | | Detected anomaly number |
| [014][013]6:16.-05 | | Die xy position |
| [015][014]7:84.108 | | Xy position on die in microns |
| [016][015]8:11 | | Defect classification |
| [017][016]9:19960327 | | Date of classification |
| [018][005]4:04 (Pointer to Wafer No.07) | | Layer number, same lot and wafer |
| [019][018]5:97 | | Detected anomaly number |
| [020][019]6:16.05 | | Die xy position |
| [021][020]7:84.108 | | Xy position on die in microns |
| [022][021]8:3 | | Defect classification |
| [023][022]9:19960322 | | Date of classification |
| [024][003]2:145221 (Pointer to main directory) | | New Lot number |
| [025][024]3:05 | | Wafer number |

-continued

| | |
|---|---|
| [026][025]4:06 | Layer number |
| [027][026]5:86 | Detected anomaly number |
| [028][027]6:03.11 | Die xy position |
| [029][028]7:111.98 | Xy position on die in microns |
| [030][029]8:4 | Defect classification |
| [031][030]9:19960408 | Date of classification |

Figure 41C:
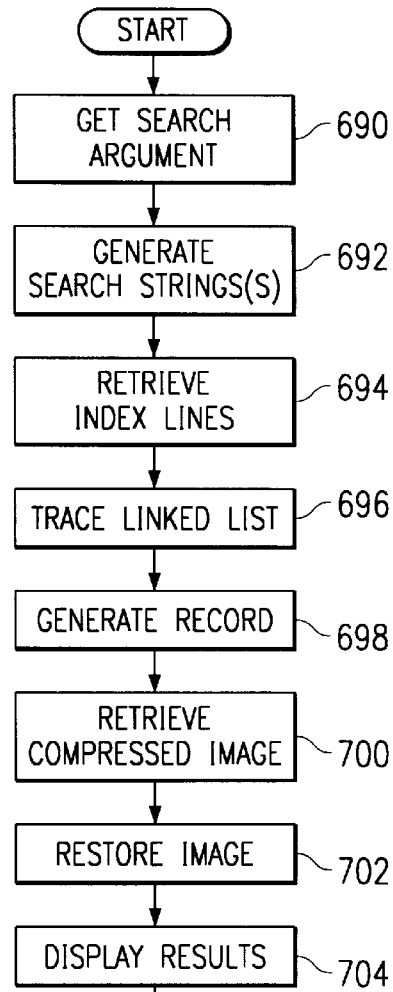
FIG. 41c is a flowchart of retrieval of data and image file addresses from indexes.
Figure 41B:
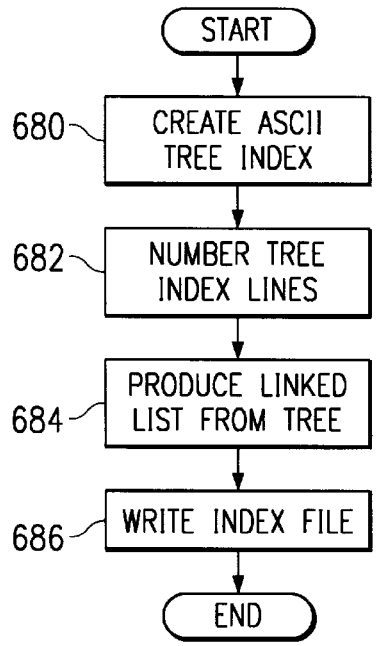
FIG. 41b is a flowchart of creation of indexes from subdirectories.

In order to retrieve data and images from the index, as shown in FIG. 41*c*, first obtain the search argument from the user interface, e.g. all defects on Layer number 6 of Lot number 144362 Wafer Number 7, search for the following strings (step 690): "2:" (Lot number), "3:" (Wafer number), and "4:" (Layer number). This gives the range of line numbers within which all the detected anomalies can be found:

| | |
|---|---|
| [004][002]2: 144362 | Lot number |
| [005][004]3:07 | Wafer number |
| [006][005]4:06 | Layer number |
| [012][005]4:05 (Pointer to Wafer No.07) | Layer number same lot and wafer |
| [018][005]4:04 (Pointer to Wafer No.07) | Layer number same lot and wafer |
| [024][003]2:145221 (Pointer to directory; new lot) | New Lot number |

Search is thus limited to lines 4–23
Retrieval of lines 4–23 on field Deducted Anomaly provides locations of all the defects on layer 6:

| | |
|---|---|
| [004][002]2:144362 | Lot number |
| [005][004]3:07 | Wafer number |
| [006][005]4:06 | Layer number |
| [007][006]5:121 | Detected anomaly number |
| [008][007]6:16.-05 | Die xy position (from wafer center) |
| [009][008]7:84.108 | Xy position on die in microns |
| [010][009]8:4 | Defect classification |
| [011][010]9:19960406 | Date of classification |
| [012][005]4:05 (Pointer to Wafer No.07) | Layer number, same lot and wafer |
| [013][012]5:43 | Detected anomaly number |
| [014][013]6:16.-05 | Die xy position |
| [015][014]7:84.108 | Xy position on die in microns |
| [016][015]8:11 | Defect classification |
| [017][016]9:19960327 | Date of classification |
| [018][005]4:04 (Pointer to Wafer No.07) | Layer number, same lot and wafer |
| [019][018]5:97 | Detected anomaly number |
| [020][019]6:16.-05 | Die xy position |
| [021][020]7:84.108 | Xy position on die in microns |
| [022][021]8:3 | Defect classification |
| [023][022]9:19960322 | Date of classification |

From this data, a wafer map that graphically represents the locations of the defects on layer 6 of Wafer 07 in Lot 144362 is produced, as in FIG. 41*c*. The defect can be directly selected through the user interface and its image retrieved, restored and displayed in seconds; a file containing the location(s) of the image file(s) for that defect is found in the final subdirectory:

\144362\07\06\121\*\*\*\*\images
d:\def_imgs\E^_C76.C1G (e.g stored on writable CD-ROM)

For "electronic peelback", involving retrieval of images of defects at the same location on previous layers, obtain the images files for all previous layers for the wafer:

C: DIR \144362\07\06\*\16.-05\84.108\*\*\*.img
\144362\07\05\*\16.-05\84.108\ \*.img
\144362\07\04\*\16.-05\84.108\ \*.img The same technique can be used on the segment record subdirectories, giving the lot, wafer, layer, and detected anomaly numbers; the xy positions are obtained from the stem record so that the relevant image files can be retrieved.

While the above method of indexing and managing a knowledge base has been discussed in terms of a knowledge base used to catalog wafer and wafer defects, the use of an operating systems subdirectory and tree commands can be used to organize many deferent types of images and information. For example, military surveillance photographs may be stored with subdirectories referring to mission numbers as opposed to a wafer's lot number.

VII. CONCLUSION

Although the present invention and its advantages have been described in detail, it should be understood that various changes, substitutions and alterations can be made herein without departing from the spirit and scope of the invention as defined by the appended claims.

What is claimed is:

1. A system for detecting anomalies on a semiconductor wafer, the system comprising:

a moveable stage for holding and positioning the semiconductor wafer;

a camera for capturing an image of the semiconductor wafer;

a digitizer coupled to the camera for producing a digital-pixel-based representation of the image;

a computer having a processor and memory, the computer coupled to the digitizer for receiving the digital-pixel-based representation from the digitizer and coupled to the stage for selectively moving the stage to align the wafer; and the computer is programmed to be operable to:
symbolically decompose the digital-pixel-based representation of an image to create a primitive-based representation of the image,
the computer further operable to develop a histogram of angles and lengths of geometric objects within the image and compare the histogram to a reference histogram of a reference image to determine rotational shift of the image.

2. The system of claim 1, wherein the computer is operable to analyze the primitive-based representation of the image to detect and locate any anomalies by analyzing the primitive-based representation of the image for irregular breaks in lines or irregular angles.

3. The system of claim 1, wherein the computer is operable to analyze the primitive-based representation of the image to detect and locate any anomalies by dividing the primitive-based representation of the image into segments, comparing segments to locate repetitive patterns, and then deleting the repetitive patterns from each segment.

4. The system of claim 1, wherein the computer is operable to analyze the primitive-based representation of the image to detect and locate any anomalies by comparing the primitive-based representation of the image with a stored, predetermined reference image.

5. The system of claim 1, wherein the computer is operable to analyze the primitive-based representation of the image to detect and locate any anomalies by subtracting a stored, predetermined reference image from the primitive-based representation of the image or subtracting a second captured reference image.

6. The system of claim 1, wherein the camera is a line-scan camera.

7. The system of claim 1, wherein the camera is a wide-scan camera.

8. A system for detecting anomalies on a manufactured device, the system comprising:

a moveable stage for holding and positioning the device;

a camera for capturing an image of the device on the stage;

a digitizer coupled to the camera for producing a digital-pixel-based representation of the image;

a computer having a processor and memory, the computer coupled to the digitizer for receiving the digital-pixel-based representation from the digitizer and coupled to the stage for selectively moving the stage to align the device; and the computer is programmed to be operable to:
symbolically decompose a digital-pixel-based representation of the image to create a primitive-based representation of the image;
analyze the primitive-based representation of the image to detect and locate any anomalies; and
the computer further to develop a histogram of angles and lengths of objects within the image and compare the histogram to a reference histogram of a reference image to determine the rotational shift of the image.

9. The system of claim 8, wherein in the device is a populated printed circuit board, and wherein the computer is operable to analyze the primitive-based representation of the image to detect and locate any anomalies by comparing the primitive-based representation of the image with a stored, predetermined reference image of a properly populated printed circuit board.

10. A method for detecting anomalies on a manufactured device, the system comprising:

placing the manufactured device on a moveable stage;

capturing and preparing a digital-pixel-based representation of the image;

symbolically decomposing the digital-pixel-based representation of an image to create a primitive-based representation of the image;

analyzing the primitive-based representation of the image to detect and locate any anomalies; and wherein the step of decomposing the digital-pixel-based representation of an image includes aligning geometric objects in the pixel-based representation of the image with respect to rotation by developing a histogram of angles and lengths and matching them with a reference histogram of a reference image to determine a rotational shift.

11. The method of claim 10, wherein the step of analyzing the primitive-based representation of the image to detect and locate any anomalies includes analyzing the primitive-based representation of the image for irregular breaks in lines or irregular angles.

12. The method of claim 10, wherein the step of analyzing the primitive-based representation of the image to detect and locate any anomalies includes dividing the primitive-based representation of the image into segments, comparing segments to locate repetitive patterns, and then deleting the repetitive patterns from each segment.

13. The method of claim 10, wherein the step of analyzing the primitive-based representation of the image to detect and locate any anomalies includes comparing the primitive-based representation of the image with a stored, predetermined reference image.

14. The method of claim 10, wherein the step of analyzing the primitive-based representation of the image to detect and locate any anomalies includes subtracting a stored, predetermined reference image from the primitive-based representation of the image or subtracting a second captured reference image.

* * * * *

UNITED STATES PATENT AND TRADEMARK OFFICE
CERTIFICATE OF CORRECTION

| | |
|---|---|
| PATENT NO. | : 6,091,846 |
| DATED | : July 18, 2000 |
| INVENTOR(S) | : YouLing Lin et al. |

It is certified that error appears in the above-identified patent and that said Letters Patent is hereby corrected as shown below:

Title page,
Item [60], Related U.S. Application Data -- Provisional Application No. 60/018,815 May 31, 1996. --

Signed and Sealed this

Eleventh Day of December, 2001

Attest:

NICHOLAS P. GODICI
Attesting Officer  Acting Director of the United States Patent and Trademark Office